United States Patent
Newman et al.

(10) Patent No.: US 9,365,905 B2
(45) Date of Patent: Jun. 14, 2016

(54) PROCESSES FOR MAKING LACTOSE UTILIZING PRE-CLASSIFICATION TECHNIQUES AND PHARMACEUTICAL FORMULATIONS FORMED THEREFROM

(75) Inventors: Stephen Newman, Ware (GB); Rudolf Johannes Damhuis, Borculo (NL)

(73) Assignees: DMV-FONTERRA EXCIPIENTS TECHNOLOGY GMBH, Goch (DE); GLAXO GROUP LIMITED, Brentford, Middlesex (GB)

( * ) Notice: Subject to any disclaimer, the term of this patent is extended or adjusted under 35 U.S.C. 154(b) by 1082 days.

(21) Appl. No.: 11/815,890

(22) PCT Filed: Feb. 6, 2006

(86) PCT No.: PCT/US2006/004032
§ 371 (c)(1),
(2), (4) Date: Aug. 9, 2007

(87) PCT Pub. No.: WO2006/086270
PCT Pub. Date: Aug. 17, 2006

(65) Prior Publication Data
US 2009/0047351 A1    Feb. 19, 2009

Related U.S. Application Data

(60) Provisional application No. 60/651,755, filed on Feb. 10, 2005.

(51) Int. Cl.
| | | |
|---|---|---|
| *A61K 9/14* | (2006.01) | |
| *A61K 31/135* | (2006.01) | |
| *A61K 31/56* | (2006.01) | |
| *C13K 5/00* | (2006.01) | |
| *A61K 9/00* | (2006.01) | |
| *A61K 31/7016* | (2006.01) | |
| *A61K 31/715* | (2006.01) | |
| *C07H 3/00* | (2006.01) | |

(52) U.S. Cl.
CPC ............... *C13K 5/00* (2013.01); *A61K 9/0075* (2013.01); *A61K 31/7016* (2013.01); *A61K 31/715* (2013.01); *C07H 3/00* (2013.01); *A61K 9/145* (2013.01)

(58) Field of Classification Search
CPC ... A61K 9/0075; A61K 31/715; A61K 9/145; C13K 5/00; C07H 3/00
See application file for complete search history.

(56) References Cited

U.S. PATENT DOCUMENTS

| | | | |
|---|---|---|---|
| 2,856,318 A | 10/1958 | Peebles | |
| 3,344,030 A | 9/1967 | Stevens et al. | |
| 3,634,582 A * | 1/1972 | Hartley et al. | 424/489 |
| 3,728,445 A | 4/1973 | Bardani | |
| 4,099,983 A | 7/1978 | Wittenberg | |
| 4,404,038 A | 9/1983 | Credoz et al. | |
| 4,778,054 A | 10/1988 | Newell et al. | |
| 4,811,731 A | 3/1989 | Newell et al. | |
| 5,035,237 A | 7/1991 | Newell et al. | |
| 5,254,330 A * | 10/1993 | Ganderton et al. | 424/46 |
| 5,478,578 A * | 12/1995 | Arnold et al. | 424/499 |
| 5,590,645 A | 1/1997 | Davies et al. | |
| 5,860,419 A | 1/1999 | Davies et al. | |
| 5,873,360 A | 2/1999 | Davies et al. | |
| 6,030,604 A | 2/2000 | Trofast | |
| 6,032,666 A | 3/2000 | Davies et al. | |
| 6,129,905 A | 10/2000 | Cutie | |
| 6,143,277 A | 11/2000 | Ashurst et al. | |
| 6,153,224 A * | 11/2000 | Staniforth | 424/490 |
| 6,170,717 B1 | 1/2001 | Di Giovanni et al. | |
| 6,221,338 B1 * | 4/2001 | Staniforth | 424/45 |
| 6,253,762 B1 | 7/2001 | Britto | |
| 6,315,173 B1 | 11/2001 | Di Giovanni et al. | |
| 6,318,603 B1 | 11/2001 | Burt | |
| 6,321,747 B1 | 11/2001 | Dmitrovic et al. | |
| 6,360,739 B1 | 3/2002 | Rand et al. | |
| 6,378,519 B1 | 4/2002 | Davies et al. | |

(Continued)

FOREIGN PATENT DOCUMENTS

| | | |
|---|---|---|
| BE | 718846 | 1/1969 |
| BE | 872319 | 5/1979 |

(Continued)

OTHER PUBLICATIONS

Zeng, Xian, The influence of Lactose carrier on the content of homogeneity and dispersibility of beclomethasone from dry powder aerosol, International Journal of Pharmaceutics 197 (2000) 41-52.*

Riepma, et al., "Consolidation and compaction of powder mixtures: II. Binary mixtures of different particle size fractions of a-lactose monohydrate" International Journal of Pharmaceutics, vol. 76, pp. 9-15 (1991).

Riepma, et al., "The effect of dry granulation on the consolidation and compaction of crystalline lactose" International Journal of Pharmaceutics, vol. 97, pp. 29-38 (1993).

Rowley, "Quantifying electrostatic interactions in pharmaceutical solid systems" International Journal of Pharmaceutics, vol. 227, pp. 47-55 (2001).

Sebhatu, et al., "Relationships between the effective interparticulate contact area and the tensile strength of tablets of amorphous and crystalline lactose of varying particle size" European Journal of Pharmaceutical Sciences, vol. 8, pp. 235-242 (1999).

(Continued)

*Primary Examiner* — Suzanne Ziska
*Assistant Examiner* — Thurman Wheeler
(74) *Attorney, Agent, or Firm* — Robert J. Smith

(57) ABSTRACT

A process for forming lactose suitable for use in a pharmaceutical formulation comprises providing a plurality of lactose particles containing no more than 10% w/w of lactose particles having a volume average particle size of about 70 microns or less; milling the plurality of lactose particles to yield a plurality of milled lactose particles with an average particle size, (D50), ranging from about 50 microns to about 100 microns; and classifying the plurality of milled lactose particles into at least two fractions comprising a fine fraction and a coarse fraction wherein the fine fraction has an average particle size, (D50), ranging from about 3 microns to about 50 microns, and the coarse fraction has an average particle size, (D50), ranging from about 40 microns to about 250 microns.

15 Claims, 4 Drawing Sheets

(56) References Cited

U.S. PATENT DOCUMENTS

| | | | |
|---|---|---|---|
| 6,390,291 | B1 | 5/2002 | Garrill et al. |
| 6,431,168 | B1 | 8/2002 | Rand et al. |
| 6,511,653 | B1 | 1/2003 | Britto et al. |
| 6,532,955 | B1 | 3/2003 | Ashurst et al. |
| 6,536,427 | B2 | 3/2003 | Davies et al. |
| 6,546,928 | B1 | 4/2003 | Ashurst et al. |
| 6,623,760 | B1 | 9/2003 | Yang et al. |
| 2001/0051187 | A1 | 12/2001 | Yang |
| 2002/0053344 | A1* | 5/2002 | Davies et al. ............ 128/203.15 |
| 2003/0157184 | A1 | 8/2003 | Yang |
| 2004/0037784 | A1 | 2/2004 | Armour et al. |
| 2004/0109828 | A1 | 6/2004 | Yang |
| 2004/0258626 | A1* | 12/2004 | Zeng .............................. 424/46 |

FOREIGN PATENT DOCUMENTS

| | | |
|---|---|---|
| DE | 246121 A1 | 5/1987 |
| DE | 19962926 A1 | 6/2001 |
| DE | 4140689 B4 | 11/2007 |
| EP | 069715 A1 | 1/1983 |
| EP | 52541 B1 | 2/1985 |
| EP | 239172 B1 | 2/1993 |
| EP | 311977 B1 | 12/1993 |
| EP | 611589 B1 | 8/1997 |
| GB | 1381872 | 1/1975 |
| GB | 2064336 | 6/1981 |
| GB | 2129691 A | 5/1984 |
| GB | 2169265 A | 7/1986 |
| GB | 2178965 A | 2/1987 |
| GB | 2240337 A | 7/1991 |
| GB | 2242134 A | 9/1991 |
| JP | 55019237 | 2/1980 |
| JP | 55071498 | 5/1980 |
| JP | 2001072586 | 3/2001 |
| JP | 2001151673 | 6/2001 |
| JP | 2003313118 | 11/2003 |
| NL | 7908599 | 6/1980 |
| RU | 1787413 | 1/1993 |
| RU | 1796844 | 2/1993 |
| SU | 1105506 | 7/1984 |
| SU | 1208078 | 1/1986 |
| SU | 1227670 | 4/1986 |
| SU | 1286631 | 1/1987 |
| SU | 1296581 | 3/1987 |
| SU | 1337026 | 9/1987 |
| WO | 9511666 A1 | 5/1995 |
| WO | 9524889 A1 | 9/1995 |
| WO | 9623485 A1 | 8/1996 |
| WO | 9826827 A1 | 6/1998 |
| WO | 9948475 A1 | 9/1999 |
| WO | 0033789 A2 | 6/2000 |
| WO | 0038811 A1 | 7/2000 |
| WO | 0044352 A1 | 8/2000 |
| WO | 0053158 A1 | 9/2000 |
| WO | 0105429 A2 | 1/2001 |
| WO | 0132125 A2 | 5/2001 |
| WO | 0145677 A1 | 6/2001 |
| WO | 0160341 A1 | 8/2001 |
| WO | 0176560 A1 | 10/2001 |
| WO | 0178693 A2 | 10/2001 |
| WO | 0178694 A2 | 10/2001 |
| WO | 0178695 A2 | 10/2001 |
| WO | 0189491 A1 | 11/2001 |
| WO | 0189492 A1 | 11/2001 |
| WO | 0200197 A1 | 1/2002 |
| WO | 0228368 A1 | 4/2002 |
| WO | 0230389 A1 | 4/2002 |
| WO | 0230390 A1 | 4/2002 |
| WO | 0230394 A2 | 4/2002 |
| WO | 0250089 A1 | 6/2002 |
| WO | 02080884 A2 | 10/2002 |
| WO | 03024396 A2 | 3/2003 |
| WO | 03077886 A1 | 9/2003 |
| WO | 03088943 A1 | 10/2003 |
| WO | 03088944 A1 | 10/2003 |
| WO | 03090786 A1 | 11/2003 |
| WO | 2004052334 A2 | 6/2004 |

OTHER PUBLICATIONS

Sebhatu, et al., "The effect of moisture content on the compression and bond-formation properties of amorphous lactose particles" International Journal of Pharmaceutics, vol. 146, pp. 101-114 (1997).

Shah, et al., "High Energy Ordered Mixture for Improving the Dissolution Rate of Sparingly Soluble Compounds" Drug Development and Industrial Pharmacy, vol. 20 (5), pp. 873-888 (1994).

Shekunov, et al., "Aerosolisation behaviour of micronised and supercritically-processed powders" Aerosol Science, vol. 34, pp. 553-568 (2003).

Srichana, et al., "On the relationship between drug and carrier deposition from dry powder inhalers in vitro" International Journal of Pharmaceutics, vol. 167, pp. 13-23 (1998).

Steckel, et al., "In vitro evaluation of dry powder inhalers II: influence of carrier particle size and concentration on in vitro deposition" International Journal of Pharmaceutics, vol. 154, pp. 31-37 (1997).

Steckel, et al., "Functionality testing of inhalation grade lactose" European Journal of Pharmaceutics and Biopharmaceutics, vol. 57, pp. 495-505 (2004).

Stubberud, et al., "The use of gravimetry for the study of the effect of additives on the moisture-induced recrystallisation of amorphous lactose" International Journal of Pharmaceutics, vol. 163, pp. 145-156 (1998).

Takano, et al., "Binderless granulation of pharmaceutical fine powders with coarse lactose for dry powder inhalation" Powder Technology, vol. 131, pp. 129-138 (2003).

Takano, et al., "Binderless granulation of pharmaceutical lactose powders" Powder Technology, vol. 122, pp. 212-221 (2002).

Takano, et al., "Fluidized bed binderless granulation of hydrophobic drugs with fine lactose powder" Advanced Powder Takano, vol. 14(3), pp. 369-381 (2003).

te Wierik, et al., "Formulation of Lactose for Inhaled Delivery Systems" Pharmaceutical Technology Europe, pp. 1-5 (2002).

Tee, et al., "The use of different sugars as fine and coarse carriers for aerosolised salbutamol sulphate" International Journal of Pharmaceutics, vol. 208, pp. 111-123 (2000).

Thwaites, et al., "An Investigation of the Effect of High Speed Mixing on the Mechanical and Physical Properties of Direct Compression Lactose" Drug Development and Industrial Pharmacy, vol. 17(4), pp. 503-517 (1991).

Nakate, et al., "Formulation development of inhalation powders for FK888 with carrier lactose using Spinhaler and its absorption in healthy volunteers" Journal of Controlled Release, vol. 97, pp. 19-29 (2004).

Valle-Vega, et al., "Variability of Growth of Lactose Crystals Under Commercial Treatment" J. Dairy Sci., vol. 60, pp. 1544-1549 (1977).

van den Dries, et al.., "Relationship between inhomogeneity phenomena and granule growth mechanisms in a high-shear mixer" International Journal of Pharmaceutics, vol. 247, pp. 167-177 (2002).

Vanbever, et al., Formulation and Physical Characterization of Large Porous Particles for Inhalation, Pharmaceutical Research, vol. 16(11), pp. 1735-1742 (1999).

Vanderbist, et al., "Optimization of a Dry Powder Inhaler Formulation of Nacystelyn, a New Mucoactive Agent" J. Pharm. Pharmacol., vol. 51, pp. 1229-1234 (1999).

Vatsaraj, et al., "Optimization of the Operating Conditions of a Lab Scale Aljet Mill Using Lactose and Sucrose: A Technical Note" AAPS PharmSciTech, vol. 4(2), Article 27, pp. 1-6 (2003).

Vojnovic, et al., "Experimental Design for a Granulation Process with "A Priori" Criterias" Drug Development and Industrial Pharmacy, vol. 21 (7), pp. 823-831 (1995).

Vromans, et al., "Studies on Tableting Properties of Lactose; The Effect of Initial Particle Size on Binding Properties and Dehydration Characteristics of a-Lactose Monohydrate" Drug Development and Industrial Pharmacy, vol. 12 (11-13), pp. 1715-1730 (1986).

Vromans, et al., "Studies of tableting properties of lactose. IX. The relationship between particle structure and compactibility of crystalline lactose" International Journal of Pharmaceutics, vol. 39, pp. 207-212, (1987).

(56) References Cited

OTHER PUBLICATIONS

Vromans, et al., "Studies on tableting properties of lactose. VII. The effect of variations in primary particle size and percentage of amorphous lactose in spray dried lactose products" International Journal of Pharmaceutics, vol. 35, pp. 29-37 (1987).

Vromans, et al., "Studies on tableting properties of lactose. VIII. The effect of variations in primary particle size, percentage of amorphous lactose and addition of a disintegrant on the disintegration of spray-dried lactose tablets" International JOunral of Pharmaceutics, vol. 39, pp. 201-206 (1987).

Whiteman, et al., "Variations in Lactose NF from Two Different Sources and Their Influence on Tablet Properties" Drug Development and Industrial Pharmacy, vol. 16(11), pp. 1815-1827 (1990).

Zeng, et al., "The role of fine particle lactose on the dispersion and deaggregation of salbutamol sulphate in an air stream in vitro" International Journal of Pharmaceutics, vol. 176, pp. 99-110 (1998).

Zeng, et al., "Crystallization of Lactose from Carbopol Gels" Pharmaceutical Research, vol. 17(7), pp. 879-886 (2000).

Zeng, et al., "The influence of lactose carrier on the content homogeneity and dispersibility of beclomethasone dipropionate from dry powder aerosols" International Journal of Pharmaceutics, vol. 197, pp. 41-52 (2000).

Zeng, et al.,. "The use of lactose recrystallised from carbopol gels as a carrier for aerosolised salbutamol sulphate" European Journal of Pharmaceutics and Biopharmaceutics, vol. 51, pp. 55-62 (2001).

Zeng, et al., "Effects of particle size and adding sequence of fine lactose on the deposition of salbutamol sulphate from a dry powder formulation" International Journal of Pharmaceutics, vol. 182, pp. 133-144 (1999).

Zeng, et al., "Lactose as a Carrier in Dry Powder Formulations: The Influence of Surface Characteristics on Drug Delivery" Journal of Pharmaceutical Sciences, vol. 90(9), pp. 1424-1434 (2001).

Zeng, et al., "The Effects of Carrier Size and Morphology on the Dispersion of Salbutamol Sulphate after Aerosolization at Different Flow Rates" J. Pharm. Pharmacol., vol. 52, pp. 1211-1221 (2000).

Zeng, et al., "The influence of carrier morphology on drug delivery by dry powder inhalers" International Journal of Pharmaceutics, vol. 200, pp. 93-106 (2000).

Zeng, et al., "The Influence of Crystallization Conditions on the Morphology of Lactose Intended for Use as a Carrier for Dry Powder Aerosols" J. Pharm. Pharmacol., vol. 52, pp. 633-643 (2000).

Zuurman,e t al., "The relationship between bulk density and compactibility of lactose granulations" International Journal of Pharmaceutics, vol. 102, pp. 1-9 (1994).

Zeng, X.M., et al; The role of fine particle lactose on the dispersion and deaggregation of salbutamol sulphate in an air stream in vitro; International Journal of Pharmaceutics; 1998; 176; 99-110; Elsevier.

Zeng, X.M., et al; The influence of lactose carrier on the content homogeneity and dispersibility of beclomethasone dipropionate from dry powder aerosols; International Journal of Pharmaceutics; 2000; 197; 41-52; Elsevier.

Bauer-Brandl, et al. "Evaluation of a Conical Mill for Screening of Direct Compression Formulations" Drug Development and Industrial Pharmacy, vol. 22(5), pp. 417-430 (1996).

Bennett, et al., "Modification of Electrostatic Charge on Inhaled Carrier Lactose Particles by Addition of Fine Particles" Drug Development and Industrial Pharmacy, vol. 25(1), pp. 99-103 (1999).

Bolhuis, et al., "Evaluation of Anhydrous a-Lactose, A New Excipient in Direct Compression" Drug Development and Industrial Pharmacy, vol. 11(8), pp. 1657-1681 (1985).

Bolhuis, et al., "Tableting Properties of Experimental and Commercially Available Lactose Granulations for Direct Compression" Drug Development and Industrial Pharmacy, vol. 21(18), pp. 2057-2071 (1995).

Briggner, et al., "The use of isothermal microcalorimetry in the study of changes in crystallinity induced during the processing of powders" International Journal of Pharmaceutics, vol. 105, pp. 125-135 (1994).

Cal, et al., "Comparison of a spray-dried a-lactose monohydrate with a fully hydrated roller-dried B-lactose." International Journal of Pharmaceutics, vol. 136, pp. 13-21 (1996).

Cal, et al., "Effects of hydration on the properties of a roller-dried B-lactose for direct compression." International Journal of Pharmaceutics, vol. 129, pp. 253-261 (1996).

Chan, et al., "Ultrafine Grinding Using a Fluidized Bed Opposed Jet Mill: Effects of Feed Load and Rotational Speed of Classifier Wheel on Particle Shape" Drug Development and Industrial Pharmacy, vol. 28(8), pp. 939-947 (2002).

Chan, et al., "Immobilization of Fine Particles on Lactose Carrier by Precision Coating and Its Effect on the Performance of Dry Powder Formulations" Journal of Pharmaceutical Sciences, vol. 92(5), pp. 975-984 (2003).

Chavan, et al., "Effect of Rise in Simulated Inspiratory Flow Rate and Carrier Particle Size on Powder Emptying from Dry Powder Inhalers" AAPS Pharmsci, vol. 2(2), article 10 (2000).

Chen, et al., "Energy-based Analysis of Milling a-lactose Monohydrate" Journal of Pharmaceutical Sciences, vol. 93 (4), pp. 886-895 (2004).

Chidavaenzi, et al., "The use of thermal techniques to assess the impact of feed concentration on the amorphous content and polymorphic forms present in spray dried lactose." International Journal of Pharmaceutics, vol. 159, pp. 67-74 (1997).

Clarke, et al., "The formulation of Powder Inhalation Systems Containing a High Mass of Nedocromil Sodium Trihydrate" Journal of Pharmaceutical Sciences, vol. 90(2), pp. 213-223 (2001).

Podzeck, "Adhesion measurements to aid the formulation of dry powder inhalations" Current Topics in Colloid & Interface Science, vol. 5, pp. 221-235 (2002).

De Matas, et al., "The Effects of Particle Size and Sample Weight on the Dehydration of Lactose Monohydrate" Poster Session p. 3. 060.

Feeley, et al., "Processing effects on the surface properties of a-lactose monohydrate assessed by inverse gas chromatography (IGC)" Journal of Materials Science, vol. 37, pp. 217-222 (2002).

Fielden, et al., "The influence of lactose particle size on spheronization of extrudate processed by a ram extruder" International Journal of Pharmaceutics, vol. 81, pp. 205-224 (1992).

Garnier, et al., "Influence of supersaturation and structurally related additives on the crystal growth of a-lactose monohydrate" Journal of Crystal Growth, vol. 234, pp. 207-219 (2002).

Harjunen, et al., "Lactose modifications enhance its drug performance in the novel multiple dose Taifun DPI" European Journal of Pharmaceutical Sciences, vol. 16, pp. 313-321 (2002).

Hassanpour, et al., "Distinct element analysis of the effect of temperature on the bulk crushing of a-lactose monohydrate" Advanced Powder Technol., vol. 14(4), pp. 427-434 (2003).

Iida, et al., "Evaluation of Flow Properties of Dry Powder Inhalation of Salbutamol Sulfate with Lactose Carrier" Chem. Pharm. Bull., vol. 49(10), pp. 1326-1330 (2001).

Iida, et al., "Preparation of Dry Powder Inhalation by Surface Treatment of Lactose Carrier Particles" Chem. Pharm. Bull., vol. 51(1), pp. 1-5 (2003).

Ikegami, et al., "A new spherically agglomerated drug composite system with lactose for dry powder inhalation" Advanced Powder Technology, vol. 14(2), pp. 215-229 (2003).

Islam, et al., "Lactose Surface Modification by Decantation: Are Drug-Fine Lactose Ratios the Key to Better Dispersion of Salmeterol Xinafoate from Lactose-Interactive Mixtures?" Pharmaceutical Research, vol. 21(3), pp. 492-499 (2004).

Juppo, et al., "Determination of size distribution of lactose, glucose and mannitol granules by sieve analysis and laser diffractometry" International Journal of Pharmaceutics, vol. 88, pp. 141-149 (1992).

Larhrib, et al., "Characterisation and deposition studies of engineered lactose crystals with potential for use as a carrier for aerosolised salbutamol sulfate from dry powder inhalers" European Journal of Pharmaceutical Sciences, vol. 19, pp. 211-221 (2003).

Larhrib, et al., "The influence of carrier and drug morphology on drug delivery from dry powder formulations" International Journal of Pharmaceutics, vol. 257, pp. 283-296 (2003).

Larhrib, et al., "The use of different grades of lactose as a carrier for aerosolised salbutamol sulphate" International Journal of Pharmaceutics, vol. 191, pp. 1-14 (1999).

Lee, et al., "Use of a Fluidized Bed Hammer Mill for Size Reduction and Classification: Effects of Process Variables and Starting Materi-

(56) References Cited

OTHER PUBLICATIONS als on the Particle Size Distribution of Milled Lactose Batches" Pharmaceutical Development and Technology, vol. 8(4), pp. 431-442 (2003).

Lerk, "Consolidation and Compaction of Lactose" Drug Development and Industrial Pharmacy, vol. 19(17&18), pp. 2359-2398 (1993).

Leuenberger, et al., "Relation between crushing strength and internal specific surface area of lactose compacts" International Journal of Pharmaceutics, vol. 52, pp. 91-100 (1989).

Longuemard, et al., "Ground and native crystals: comparison of compression capacity and dissolution rate" International Journal of Pharmaceutics, vol. 170, pp. 51-61 (1998).

Louey, et al., "Particle Interactions Involved in Aerosol Dispersion of Ternary Interactive Mixtures" Pharmaceutical Research, vol. 19(10), pp. 1524-1531 (2002).

Lowe, et al., "A Mathematical Model for Lactose Dissolution, Part II. Dissolution Below the Alpha Lactose Solubility Limit" Journal of Food Engineering, vol. 38, pp. 15-25 (1998).

Lucas, et al., "Protein Deposition from Dry Powder Inhalers: Fine Particle Multiplets as Performance Modifiers" Pharmaceutical Research, vol. 15(4), pp. 562-569 (1998).

Mackaplow, et al., "Effect of primary particle size on granule growth and endpoint determination in high-shear wet granulation" Powder Technology, vol. 108, pp. 32-45 (2000).

Mackin, et al., "Quantification of low levels (<10%) of amorphous content in micronised active batches using dynamic vapour sorption and isothermal microcalorimetry." International Journal of Pharmaceutics, vol. 231, pp. 227-236 (2002).

Modler, et al., "Influence of pH, Casein, and Whey Protein Denaturation on the Composition, Crystal Size, and Yield of Lactose from Condensed Whey" J. Dairy Sci, vol. 69, pp. 684-697 (1986).

Murakami, et al "Correlation between loose density and compactibility of granules prepared by various granulation methods" International Journal of Pharmaceutics, vol. 216, pp. 159-164 (2001).

Newell, et al., "The Use of Inverse Phase Gas Chromatography to Measure the Surface Energy of Crystalline, Amorphous, and Recently Milled Lactose" Pharmaceutical Research, vol. 18(5), pp. 662-666 (2001).

Newell, et al., "The use of inverse phase gas chromatography to study the change of surface energy of amorphous lactose as a function of relative humidity and the processes of collapse and crystallisation" International Journal of Pharmaceutics, vol. 217, pp. 45-56 (2001).

Ohkuma, et al., "Development of Air Separator for Pharmaceutical Powder Products" J. Soc. Powder Technol., vol. 39, pp. 864-869 (2002).

Osewa, et al., "Effect of Sieve Size for Wet and Dry Screening on the Physical Properties of Lactose Granules and Their Corresponding Tablets" Drug Development and Industrial Pharmacy, vol. 9(1&2), pp. 179-201 (1983).

Palakodaty, et al., "Supercritical Fluid Processing of materials from Aqueous Solutions: The Application of SEDS to Lactose as a Model Substance" Pharmaceutical Research, vol. 15(12), pp. 1835-1843 (1998).

Gericke, et al., PharmaZeutische Industrie, vol. 65(6), pp. 619-623 (2003).

Podczeck, "The Influence of Particle Size Distribution and Surface Roughness of Carrier Particles on the in vitro Properties of Dry Powder Inhalations" Aerosol Science and Technology, vol. 31, pp. 301-321 (1999).

Podczeck, "The relationship between physical properties of lactose monohydrate and the aerodynamic behaviour of adhered drug particles" International Journal of Pharmaceutics, vol. 160, pp. 119-130 (1998).

Raghavan, et al, "The Bulk Crystallization of a-lactose Monohydrate from Aqueous Solution" Journal of Pharmaceutical Sciences, Vo. 90(7), pp. 823-832 (2001).

Riepma, et al., "Consolidation and compaction of powder mixtures: III. Binary mixtures of different particle size fractions of different types of crystalline lactose" International Journal of Pharmaceutics, vol. 85, pp. 121-128 (1992).

Riepma, et al., "Consolidation and compaction of powder mixtures. I. Binary mixtures of same particle size fractions of different types of crystalline lactose" International Journal of Pharmaceutics, vol. 66, pp. 47-52 (1990).

Domo Closer to you. Lactopress—pharmaceutical lactose for direct compression tabletting. Lactochem—pharmaceutical lactose for wet granulation, capsules and sachets. Jan. 30, 2007.

Lactochem—Pharmaceutical lactose for wet granulation, capsules and sachets. Pre-2005.

Steckel, et al. "Effect of milling and sieving on functionality of dry powder inhalation products" 2006; Int. J. Pharm; vol. 309; pp. 51-59.

Pilcer, et al. "Lactose characteristics and the generation of the aerosol." 2012; Adv. Drug Del.Revs.; vol. 64; pp. 233-256.

Ho, et al. "Influence of fines on the surface energy heterogeneity of lactose for pulmonary drug delivery." 2010; Int. J. Pharm.; vol. 388; pp. 88-94.

MacGregor, et al.; "A preliminary study of size reduction of powders in a single-vessel pharmaceutical processor." Poceedings of the Institution of Mechanical Engineers Part B—Journal of Engineering Manufacture; 2000; pp. 251-253; 214(3).

Mikkonen, et al.; "Effect of nanofiltration on lactose crystallisation." Milchwissenschaft; 2001; pp. 307-310; 56(6).

Morita, et al; "Physiochemical properties of crystalline lactose. II> Effect of crystallinity on mechanical and structural properties." Chem. Pharm. Bull.; 1984; pp. 4076-4083; 32(10).

Naini, et al.; "Physiochemical Stability of Crystalline Sugars and Their Spray-Dried Forms-Dependence upon Relative Humidity and Suitability for Use in Powder Inhalers." Drug Development & Industrial Pharmacy; 1998; pp. 895-909; 24 (10).

Otsuka, et al.; "Isomerization of lactose in solid-state by mechanical stress during grinding." Journal of Pharmacy Pharmacology; 1991; pp. 148-153; 43(3).

Otsuka, et al.; "Effect of humidity on solid-state isomerization of various kinds of lactose during grinding." Journal of Pharmacy & Pharmacology; 1993; pp. 2-5; 45(1).

Perevoznikov, et al.; "Installation for fine milling of lactose crystals." Vsesoyuznyi Nauchno-issledovatel'skii Institut Maslodel'noi Syrodel'noi Promyshlennosti; 1975; pp. 66-69, 78; 20 (Abstract Only).

Podczeck, F.; "Adhesion forces in interactive powder mixtures of a micronized drug and carrier particles of various particle size distributions." Journal of Adhesion Science & Technology; 1998; pp. 1323-1339; 12(12).

Riepma, et al.; "Consolidation and Compaction of Powder Mixtures I. Binary Mixtures of Same Particle Size Fractions of Different Types of Crystalline Lactose." Int. J. Pharm.; 1990; pp. 47-52; 66(1-3).

Riepma, et al.; "Consolidation and Compaction of Powder Mixtures II. Binary Mixtures of Different Particle Size Fractions of Alpha Lactose Monohydrate." Int. J. Pharm.; 1991; pp. 9-16; 76(1-2).

Ritala, et al.; "The effect of binder solution quantity and lactose particle size on granule properties." Acta Pharmaceutica Nordica; 1991; pp. 229-234; 3(4).

Ritala, et al.; "Effect of Lactose Grade and the Amount of Binder in Granules on the Tablet Properties." Acta Pharm Fenn.; 1991; pp. 281-288; 100(4).

Sakr, et al.; "Effect of granule size and compression." Manuf. Chem. Aerosol News ; 1973; pp. 29-33; 44(Feb).

Schaefer, et al.; "Melt pelletization in a high shear mixer. III. Effects of lactose quality." Acta Pharmaceutica Nordica; 1992; pp. 245-252; 4(4).

Shi, et al.; "Crystallization kinetics of alpha-lactose monohydrate in a continuous cooling crystallizer." Journal of Food Science; 1990; pp. 817-820; 55(3).

Spring ;" Segregation of granules during tableting." Journal of Pharmacy & Pharmacology; 1977; pp. 513-514; 29 (Aug).

Staniforth ; "Performance-Modifying Influences in Dry Powder Inhalation Systems." Aerosol Science & Technology; 1995; pp. 346-353; 22(4).

(56) References Cited

OTHER PUBLICATIONS

Steiner, et al.; "Effects of milling on granulation particle size distribution." Journal of Pharmaceutical Sciences; 1974; pp. 1395-1398; 63(Sep).
Tapper, et al.; "The granulation of some lactose qualities with different particle size distributions in a domestic-type mixer." Acta Pharm. Suec.; 1986; pp. 47-56; 23(1).
Tatsumi, et al.; "Influence of load on particle size distribution of lactose fluidized powder (Japanese)." Yakuzaigaku, Faculty of Pharmaceutical Sciences; 2000; pp. 88-100; 60(1) (English Translation).
Topal, et al.; "Lactose crystallization in the presence of phosphatide concentrates (Russian)." Pishchevaya Teknologiya; 1997; pp. 58-59; (1) (Abstract Only).
Valle-Vega, et al.; "Measurement of lactose crystal growth by image analyzer." Journal of Food Science; 1977; pp. 1069-1072; 42(4).
Van Kreveld ; "Growth rates of lactose crystals in solutions of stable anhydrous a-lactose." Ned. Melk-Zuiveltijdschr.; 1969; pp. 258-275; 23(4).
Vojnovic, et al.; "Experimental design for a granulation process with a priori criterias." Drug Development & Industrial Pharmacy; 1995; pp. 823-831; 21(7).
Vromans, et al.; "Studies on tableting properties of lactose. Part 2. Consolidation and compaction of different types of crystalline lactose." Pharm. Weekbl., Sci. Ed.; 1985; pp. 186-193; 7(5).
Vromans, et al.; "Studies on tableting properties of lactose. Part 1. Effect of initial particle size on binding properties and dehydration characteristics of lactose." Acta Pharmaceutica Suecica; 1985; pp. 163-172; 22(3).
Weyhers, et al.; "Analysis of particle size distribution of micronized lactose by laser diffractometry." Pharmazeutische Industrie; 1996; pp. 354-357; 58(4).
Weyhers, et al.; "Analysis of particle size distribution of micronized lactose by laser diffractometry." Drugs Made in Germany; 1997; pp. 66-69; 40(2).
Zatloukal, Z.; "Evaluation of bulk properties of mixtures of size fractions of lactose. Czech." Ceska a Slovenska Farmacie; 1995; pp. 313-316; 44(6) (Abstract Only).
Zeng, et al.; "Effects of surface smoothness of lactose on the delivery of salbutamol sulphate from dry powder Inhalers." Pharm. Res.; 1997; pp. S136-S137; 14(11, Suppl).
Alpar, et al.; "Compression properties of lactose." J. of Pharmacy & Pharmacology; 1970; pp. 1S-7S; 22 (Dec Suppl).
Barrau, et al.; "Interest of the relation wetting/particle size yield in extrusion/spheronization. Application to four varieties of lactose (French)." Pharmaceutica Acta Helvetiae; 1992; pp. 124-128; 67(4) (Abstract Only).
Bernabe, et al.; "Compression Ability Improvement of Lactose by Recrystallization—Influence of Lactose Phosphate Content." Farmaco; 1995; pp. 801-809; 50(11).
Bernabe, et al.; "An attempt at explaining the variability of the compression capacity of lactose." Pharmaceutical Technology; 1997; pp. 66-78; 21(5).
Bernabe, et al.; "Attempt at explaining the variability of the compression capacity of lactose." Pharmaceutical Technology International; 1997; pp. 42, 44, 46-48, 50; 9(Jan).
Bos ; "Backgrounds of technologies used for the production of lactose." Bulletin of the International Dairy Federation; 1987; pp. 99-102; 212 (Abstract Only).
Carter, et al.; "Triboelectrification of fractionated crystalline and spray-dried lactose." Pharmacy & Pharmacology aommunications; 1998; pp. 111-115; 4(Feb).
Cartilier, et al.; "Effect of particle morphology on the flow and packing properties of lactose." S.T.P. Pharma Sciences; 1993; pp. 213-220; 3(3).
Cartilier, et al.; "The Effect of Particle Morphology on Flow and Packing Properties of Lactose." Pharm. Res.; 1988' pp. S231; 5(10 Suppl).
Clarke, et al.; "The effects of ternary components on the performance of nedocromil sodium in dry powder blends for Inhalation." Pharm. Res.; 1997; pp. S130-131; 14(11, Suppl.).

Clyne, et al.; "Lactose. The influence of particle size and structure on drug delivery." Royal Society of Chemistry Special Publication; 1996; pp. 97-104; 178.
Darcy, et al.; "Crystallization of bulk samples of partially amorphous spray-dried lactose." Pharmaceutical Development and Technology; 1998; pp. 503-507; 314.
Deboer, et al.; "Studies on tableting properties of lactose. Part 3. Consolidation behavior of sieve fractions of crystalline alpha-lactose monohydrate." Pharmaceutisch Weekblad—Scientific Edition; 1986; pp. 145-150; 8(Apr 25).
Di Martino, et al.; "The batch-to-batch non-reproducibility of the compression ability of lactose. Reasons and detection." S.T.P. Pharma Sciences; 1993; pp. 436-441; 3(6).
Eilbeck, et al.; "Effect of materials of construction of pharmaceutical processing equipment and drug delivery devices on the triboelectrification of size fractionated lactose." Pharmacy & Pharmacology Communications; 1999; pp. 129-433; 5(Jul.).
Eilbeck, et al.; "Effect of contamination of pharmaceutical equipment on powder triboelectrification." International Journal of Pharmaceutics; 2000; pp. 7-11; 195(Feb 15).
Embleton, et al.; "Development and in-vitro testing of PassCal dry powder formulations for the pulmonary delivery of Insulin." Pharm. Res.; 1997; pp. S138-S139; 14(11, Suppl).
Fell, et al.; "The tensile strength of lactose tablets." J. Pharm. Pharmcol.; 1968; pp. 657-659; 20(8).
Fell, et al.; "Assessment of compression characteristics of powders." J. of Pharmaceutical Sciences; 1971; pp. 1428-1429; 60(Sep).
Fell, et al.; "Effect of particle size and speed of compaction on density changes in tablets of crystalline and sprayiried lactose." J. Pharm. Sci.; 1971; pp. 1866-1869; 60(12).
Fell ; "Influence of fines on the flow and compaction properties of lactose." J. Pharm. Pharmacology; 1973; p. 109; 25 (Suppl).
Fell ; "Flow and compaction properties of lactose." Pharmaceutisch Weekblad ; 1976; pp. 681-685; 111 (Jul 9).
Fielden ; "Effect of lactose particle size on the extrusion properties of microcrystalline cellulose-lactose mixtures." J. of Pharmacy & Pharmacology; 1989; pp. 217-221; 41 (Apr.).
Frake, et al.; "Near-infrared mass median particle size determination of lactose monohydrate, evaluating several chemometric approaches." GlaxoWellcome Research and Development; 1998; pp. 2043-2046; 123(10).
Gnezdilova, et al.; "Kinetics of a-lactose crystals growth from supersaturated solutions (Russian)." Pishchevaya Tekhnologiya; 1999; pp. 65-67; (2-3) (Abstract Only).
Gohel, et al.; "Preparation of directly compressible lactose and optimization of characteristics affecting direct compression." Indian Drugs; 1997; pp. 322-326; 34(6).
Gold, et al.; "Powder flow studies. III. Factors affecting the flow of lactose granules." J. Pharm. Sci.; 1968; pp. 667-684; 57(4).
Griffiths, et al.; "Preliminary investigation of lactose crystallization using the population balance technique." AIChE Symp. Ser.; 1982; pp. 118-128; 78(218).
Harris, et al.; "Effects of stressing a-lactose monohydrate on surface and particulate properties." Congr. Int. Technol. Pharm.; 1983; pp. 21-27; vol. 1 (Abstract Only).
Heng, et al.; "Ultrafine grinding using a fluidized bed opposed jet mill: effects of process parameters on the size distribution of milled particles." S.T.P. Pharma Sciences; 2000; pp. 445-451; 10(6).
Heng, et al.; "Quantification of the surface morphologies of lactose carriers and their effect on the in vitro deposition of salbutamol sulphate." Chemical & Pharmaceutical Bulletin; 2000; pp. 393-398; 48(3).
Hickey, et al.; "Flow Properties of Selected Pharmaceutical Powders from a Vibrating Spatula." Particle & Particle Systems Characterization; 1994; pp. 457-462; 11(6).
Hindle, et al.; "Size distribution control of raw materials for dry-powder inhalers using the aerosizer with the aero-disperser" Pharmaceutical Technology; 1995; pp. 64,66,68,70,72,74,76,78; 19(Jun).
Hrestak, et al.; "Investigation of the behavior of two lactose types in wet granulation process." Famracevtski Vestnik (Ljubljana); 1997; pp. 402-403; 48.

(56) References Cited

OTHER PUBLICATIONS

Huettenrauch, et al.; Molecular Galenics. Part 4: mechanochemical alteration of the crystallinity degree of lactose in the milling process (German); Pharmazie; 1976; pp. 329-330; 31(5) (Abstract Only).

Hunter, et al.; "Effect of particle size on the granulation of lactose by massing and screening." J. of Pharmacy & Pharmacology; 1972; pp. 17P -24P; 24 (Dec Suppl).

Huttenrauch, et al.; "Influence of lattice defects on the course and rate of drying of particulate solids. Part 45. Molecular pharmaceutics." International Journal of Pharmaceutical Technology & Product Manufacture; 1981; pp. 35-37; 2(Apr).

Iida, et al.; "Effect of separation characteristics between salbutamol sulfate (SS) particles and model carrier excipients on dry powder for inhalation." Yakugaku Zasshi. Journal of the Pharmaceutical Society of Japan; 1999; pp. 752-762; 119(10).

Inghelbrecht, et al.; "Roller compaction of different types of lactose." International Journal of Pharmaceutics; 1998; pp. 135-144; 166(May 18).

Juslin, et al." Effect of fluidized bed granulation on the crystal properties of lactose, glucose and mannitol." S.T.P. Pharma Sciences; 1996; pp. 173-178; 6(3).

Kassem, et al.; "Effect of granule size on physical standards of tablets." Manuf. Chem. Aerosol News; 1972; pp. 24-27; 43(Aug).

Kata ; "Shear cell investigation of powder mixtures containing micronized drugs." Acta Pharm. Technol.; 1979; pp. 203-216; 25(3) (Abstract Only).

Kay, et al.; "Design of a fluid energy single vessel powder processor for pharmaceutical use." International Journal of Pharmaceutics; 1999; pp. 243-254; 181(2).

Keller, et al.; "Lactose crystallization and manufacturing processes." In 'Proceedings, 1982 Whey Products Conference held at Schaumburg, Illinois; 1983; pp. 103-115 (Abstract Only).

Kristensen ; "Studies on flow properties of powders. VI. Some physical properties of crystalline and spray dried lactose." Dansk Tidsskrift for Farmaci; 1971; pp. 114-124; 45(Apr).

Krycer, et al.; "Detection of mechanical activation during the milling of lactose monohydrate." Int'l Journal of Pharmaceutical; 1981; pp. 55-56; 2(2) (Abstract Only).

Lallukka, et al ; "Particle size measurement of lactose powder with an electrical sensing zone method (Coulter Principle)." Meijeritieteellinen Aikakauskirja; 1986; pp. 63-73; 44(2).

Lerk, et al.; "The effect of mechanical treatment on the properties of lactose as observed by differential scanning calorimetry." Neth. Milk Dairy J.; 1980; pp. 69-73; 34(1).

Liang, et al.; "Growth Rate Dispersion Effects on Lactose Crystal Size Distributions from a Continuous Cooling Crystallizer." Journal of Food Science; 1991; pp. 848-854; 56(4).

Lucas, et al.; "Protein deposition from dry powder inhalers: effect of performance modifiers." Pharm. Res.; 1997; pp. S130; 14(11, Suppl).

Bos; "Backgrounds of technologies used for the production of lactose." Bulletin of the International Dairy Federation; 1987; pp. 99-102; 212.

Keller, et al.; "Lactose crystallization and manufacturing processes." In 'Proceedings, 1982 Whey Products Conference held at Schaumburg, Illinois; 1983; pp. 103-115.

Krycer, et al.; "Detection of mechanical activation during the milling of lactose monohydrate." Int'l Journal of Pharmaceutical; 1981; pp. 55-56; 2(2).

Harris, et al.; "Effects of stressing a-lactose monohydrate on surface and particulate properties." Congr. Int. Technol. Pharm. 3rd.; 1983; pp. 21-27; vol. 1.

* cited by examiner

PROCESSES FOR MAKING LACTOSE UTILIZING PRE-CLASSIFICATION TECHNIQUES AND PHARMACEUTICAL FORMULATIONS FORMED THEREFROM

CROSS-REFERENCE TO RELATED APPLICATIONS

This application is filed pursuant to 35 USC 371 as a United States National Phase Application of International Patent Application Serial No. PCT/US2006/004032 filed on Feb. 6, 2006, which claims priority from 60/651,755 filed on Feb. 10, 2005 in the United States.

FIELD OF THE INVENTION

The invention generally relates to processes for making lactose and pharmaceutical formulations formed therefrom.

BACKGROUND OF THE INVENTION

In the field of inhalation therapy, it is generally desirable to employ therapeutic molecules having a particle size (i.e., diameter) in the range of 1 to 10 μm. Carrier molecules or excipients, such as lactose, for inhaled therapeutic preparations also include significantly larger diameter particles (e.g., 100 to 150 μm) that typically do not penetrate into the upper respiratory tract to the same degree as the active ingredient. In general, it is preferable to use a smaller particle size for the lactose or a lactose blend having a defined ratio of coarse and fine lactose.

The lactose particle size and distribution will also, in many instances, significantly influence pharmaceutical and biological properties, such as, for example, bioavailablity. For example, it is well known that coarse lactose in crystalline form has a fair flow rate and good physical stability whereas fine lactose powder, such as that produced by conventional fine grinding or milling, generally lacks good flow properties. Lactose prepared by conventional spray drying either lacks desired flow properties or contains too many large sized lactose crystals.

It is well known that one particular drawback associated with conventional means of producing pharmaceutical grade lactose relates to undesirable variations in particle size, morphology and distribution. Such production methods are particularly problematic in that they often lead to excessive and undesirable variations in the fine particle mass ("FPMass") of pharmaceutical formulations employing such lactose. FPMass is the weight of medicament within a given dose that reaches the desired size airways to be effective. For example, a desired size may be defined as approximately 1 micron to 10 microns as measured by laser scattering techniques.

Lactose morphology is believed to be another important parameter to control, and it is believed that the degree of surface roughness can influence the interaction between the lactose particle and excipient and as such is now often measured as part of the lactose selection criteria. See e.g., Pharmaceutical Technology Europe April 2004, page 23.

It is possible that two lactose particles may be measured as having the same particle size, but if one is smooth, eg unmilled crystalline lactose, and the other is a rougher-surfaced milled crystal, that these could associate to a different extent with the active and thus impact upon either the initial FPMass performance or the through life stability performance of the product.

SUMMARY OF THE INVENTION

The present invention attempts to address the above problems associated with conventional processes of producing lactose, and provides a process of producing lactose possessing reduced levels of variation for both particle size distribution and particle morphology.

In one aspect, the invention provides a process for forming lactose suitable for use in a pharmaceutical formulation and having a predetermined particle size distribution. The process comprises providing a plurality of lactose particles containing no more than 10% w/w of lactose particles having a volume average particle size of about 70 microns or less; milling the plurality of lactose particles to yield a plurality of milled lactose particles with an average particle size, (D50), ranging from about 50 microns to about 100 microns; and then classifying the plurality of milled lactose particles into at least two fractions comprising a fine fraction and a coarse fraction wherein the fine fraction has an average particle size, (D50), ranging from about 3 microns to about 50 microns, and the coarse fraction has an average particle size, (D50), ranging from about 40 microns to about 250 microns. In one embodiment, appropriate amounts of coarse and fine fractions may be combined with at least one medicament to form a pharmaceutical formulation.

These and other aspects are encompassed by the present invention.

DETAILED DESCRIPTION OF THE INVENTION

Figure 1:
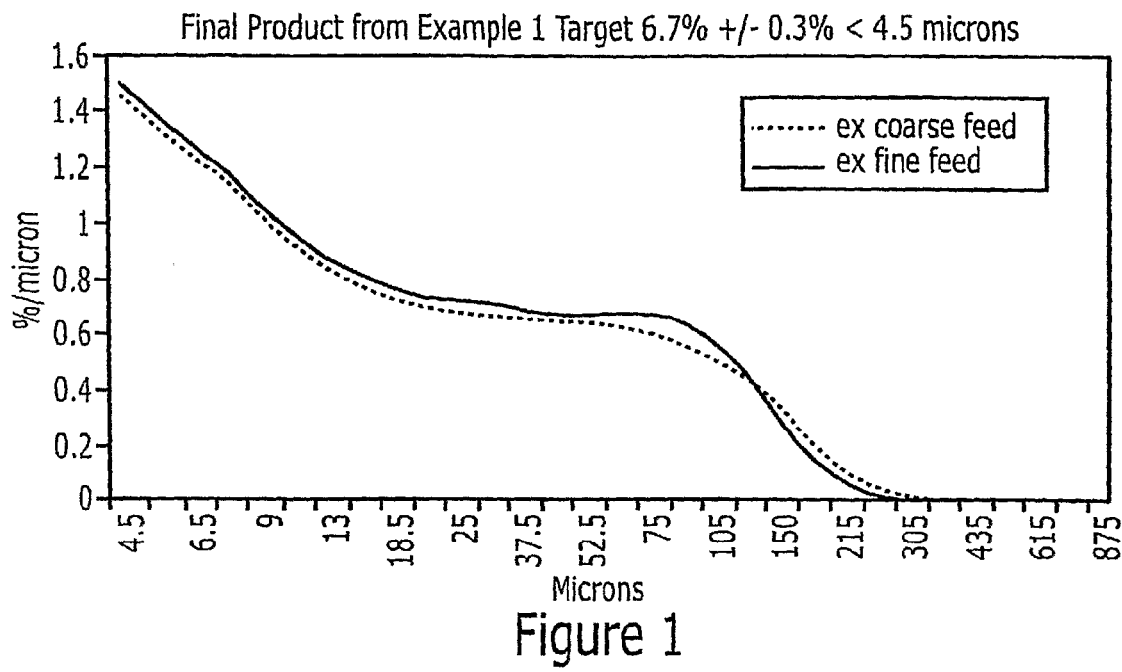
FIG. 1 illustrates a particle size profile for lactose formed in accordance with Example 1.

The invention will now be described with respect to the embodiments set forth herein. It should be appreciated that these embodiments are set forth to illustrate the invention, and that the invention is not limited to these embodiments.

All publications, patents, and patent applications cited herein, whether supra or infra, are hereby incorporated herein by reference in their entirety to the same extent as if each individual publication, patent, or patent application was specifically and individually indicated to be incorporated by reference.

It must be noted that, as used in the specification and appended claims, the singular forms "a", "an", "one" and "the" may include plural references unless the content clearly dictates otherwise.

As used herein, the term "D50" is defined as the size in microns above or below which 50 percent of the particles reside on a volume basis.

The process for forming lactose in accordance with the present invention may encompass various embodiments. For example, in one embodiment, the step of milling the plurality of lactose particles to yield a plurality of lactose particles may encompass obtaining those particles with an average particle size (D50) ranging from about 50, 55, 60, 65, 70 or 75 microns to about 70, 75, 80, 85, 90, 95 or 100 microns. In one embodiment, for example, the step of classifying the plurality of milled lactose particles into at least two fractions may result in a fine fraction having an average particle size (D50) ranging from about 3, 10, 15, 20, 25, 30 or 35 microns to about 30, 35, 40, 45 or 50 microns as well as a coarse fraction having an average particle size (D50) ranging from about 40, 75, 100, 125 or 150 microns to about 100, 125, 150, 175, 200, 225 or 250 microns, as measured by Malvern particle sizing.

In accordance with the present invention, the term "lactose" as used herein is to be broadly construed. As an example, lactose is intended to encompass physical, crystalline, amorphous and polymorphic forms of lactose, including, but not limited to, the stereoisomers α-lactose monohydrate and β-anhydrous lactose, as well as α-anhydrous lactose. Combinations of the above may be used.

Lactose (i.e., milk sugar) is preferably obtained from cheese whey, which can be manufactured in different forms depending on the process employed. As used herein, the term "particle" is to be broadly interpreted to encompass those of various shapes, sizes, and/or textures which can include those that may have varying degrees of irregularities, disuniformities, etc. or which may possess regular and/or uniform properties.

The plurality of lactose particles used in the process of the present invention may be acquired in various manners. In one embodiment, the plurality of lactose particles is present in the form of crystalline or unmilled lactose. In one embodiment, the initial step of providing lactose particles containing no more than 10% w/w of lactose particles having a volume average particle size of about 70 microns or less, comprises obtaining the plurality of lactose particles from a crystallization process. One example of a suitable crystallization process that may be employed is set forth in copending U.S. Application entitled "Process for Crystallizing Lactose Particles for Use in Pharmaceutical Formulations", Ser. No. 60/651,754 filed concurrently herewith. It should be understood that other processes may also be employed.

In another embodiment, the initial step of providing a plurality of lactose particles containing no more than 10% w/w of lactose particles having a volume average particle size of about 70 microns or less, comprises obtaining the plurality of lactose particles by sieving a source of lactose to produce the plurality of lactose particles. Typical examples of commercially available sieving apparatus are made available by Russell Finex of Charlotte, N.C. and Alpine Sieves of Augsburg, Germany.

In another embodiment, the plurality of lactose particles containing no more than 10% w/w of lactose particles having a volume average particle size of about 70 microns or less may be obtained by classifying a source of lactose into two fractions comprising the plurality of lactose particles containing no more than 10% w/w of lactose particles having a volume average particle size of about 70 microns or less and a remaining fine fraction. One example of a commercially preferred classifier made commercially available by Hosakawa of Cheshire, United Kingdom. The remaining fine fraction of lactose is lactose that is unmilled or crystalline. Optionally, prior to classifying, the particles may be subjected to sieving.

Figure 5:
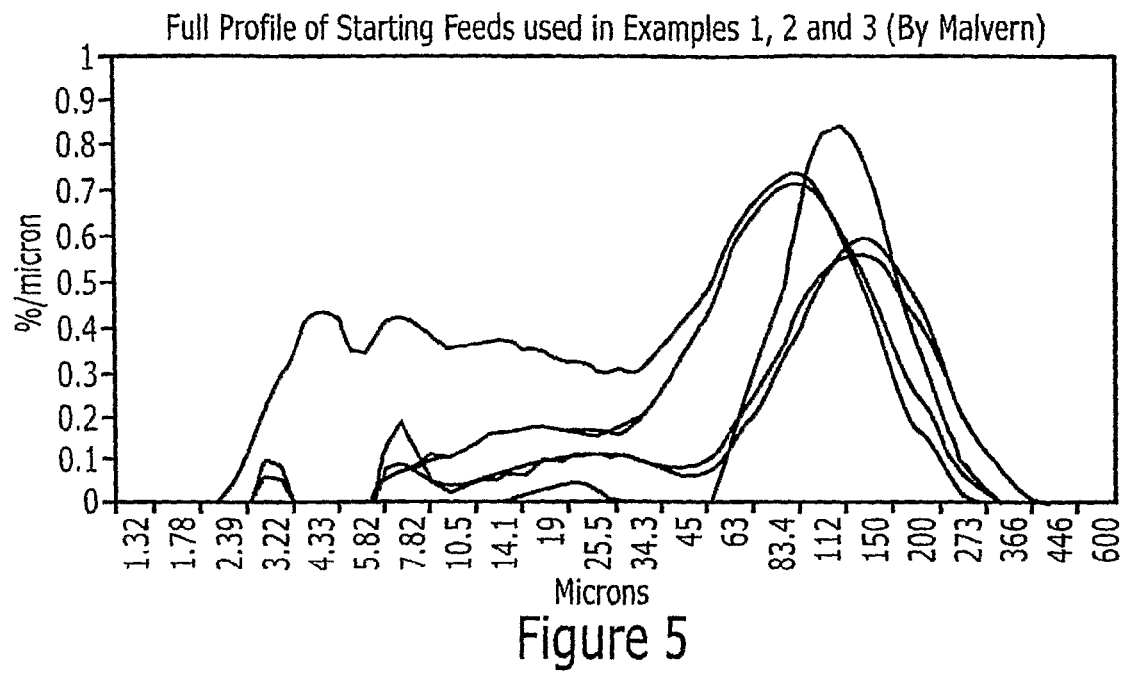
FIG. 5 illustrates the particles size distribution of the initial crystalline A feed lactose used in Examples 1, 2 and 3. This shows the varying amounts of lactose in the less than 60 micron region.
Figure 6:
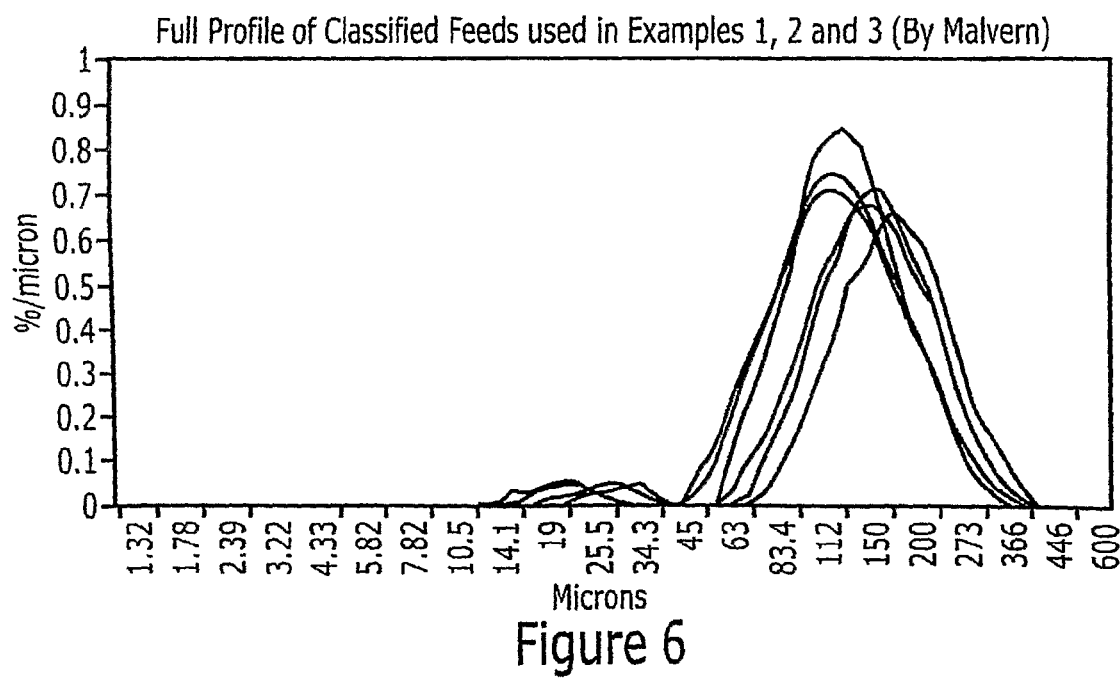
FIG. 6 illustrates the particles size distribution of the crystalline A feed lactose after it has been classified to remove the majority of the smaller crystalline lactose particles.

FIG. 5 illustrates the full particle size profile of the initial feed batches before the smaller crystals have been removed by classification. FIG. 6 illustrates the full particle size profile after the smaller crystals have been removed via a classification process. This results in a much more uniform feed material being presented to the mill.

The Span is often a parameter used to describe the narrowness/broadness of a distribution of particles. The Span is given by the following formulation:

(D90−D10)/D50=Span

The term "D90" is defined as the size in microns below which 90 percent of the particles reside on a volume basis.

The term "D10" is defined as the size in microns below which 10 percent of the particles reside on a volume basis.

Figure 7:
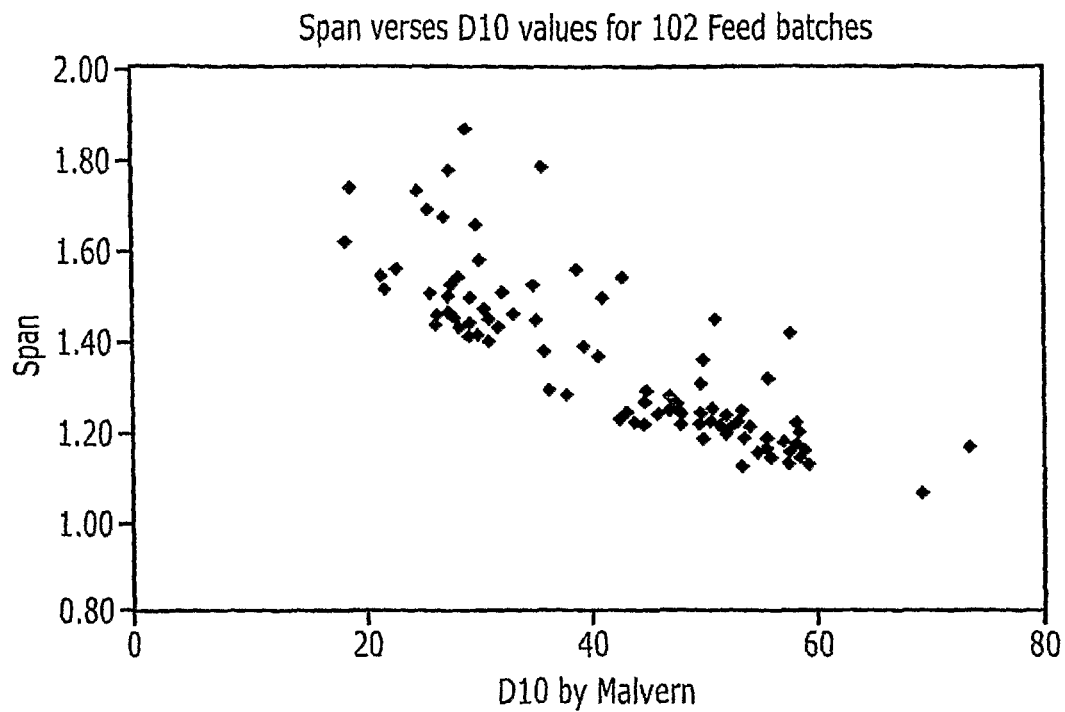
FIG. 7 illustrates the correlation between D10 and the Span of Feed Lactose Batches.

Although not intending to be bound by theory, for particles with similar D50's the smaller the Span, the tighter are the distribution of particles. In general, feed lactose batches with small Span values would be better input materials to the mill as this would indicate a narrower particle size distribution. It can be seen from FIG. 7 that the higher the D10 values are for typical crystalline A Feed lactose batches, the smaller the Span values. The following Tables 1-2 illustrate that tighter particle size distributions are obtained after the classification of the crystalline A Feed lactose, and hence produce a preferred input into the mill

TABLE 1

Malvern Data Prior to classification

|  | D10 | D50 | D90 | Span |
|---|---|---|---|---|
| Example 1 Fine feed | 57 | 123 | 208 | 1.23 |
| Example 1 coarse feed | 86 | 176 | 284 | 1.13 |
| Example 2 Fine feed | 53 | 114 | 208 | 1.36 |
| Example 2 coarse feed | 84 | 162 | 270 | 1.15 |
| Example 3 Fine feed | 53 | 114 | 207 | 1.35 |
| Example 3 coarse feed | 81 | 161 | 274 | 1.20 |

TABLE 2

Malvern Data after classification

|  | D10 | D50 | D90 | Span |
|---|---|---|---|---|
| Example 1 Fine feed | 88 | 141 | 219 | 0.93 |
| Example 1 coarse feed | 116 | 186 | 284 | 0.90 |
| Example 2 Fine feed | 79 | 140 | 236 | 1.12 |
| Example 2 coarse feed | 107 | 171 | 263 | 0.91 |
| Example 3 Fine feed | 81 | 139 | 230 | 1.07 |
| Example 3 coarse feed | 104 | 171 | 270 | 0.97 |

The step of milling the plurality of lactose particles to yield a plurality of milled lactose particles may be carried out using known techniques. As an example, in one embodiment, milling may be performed using an impact mill (e.g., air classifier mill, (ACM)) whereby size reduction of pharmaceutical grade lactose is a combination of milling and classification. In one embodiment, milling is conducted using a standard air classifier mill fitted with mill rotor and grinding pins, classifier wheel and grinding track. One example of a commercially preferred mill is the MikroPul ACM made commercially available by Hosakawa.

The process described herein is suitable for providing lactose for use in a wide range of inhalation applications, encompassing those that require very fine lactose to those requiring much coarser lactose. Such that in one embodiment the coarse fraction alone may be suitable for pharmaceutical applications and at the other extreme the fine fraction alone may be suitable for pharmaceutical applications. Required FPMass performance from inhalation devices, including, in one embodiment and without limitation Advair, can be targeted by the combination of appropriate amounts of the coarse and fine fractions. This can cover the complete range from 100 percent coarse fraction+0 percent fine fraction to 100 percent fine fraction+0 percent coarse fraction. The exact proportions that are required will depend on the particle size profile of each of the coarse and fine fractions themselves.

As an example, the above combining step may be achieved by blending, although other procedures may be employed. A typical blender used would be of the orbital screw type such as the Vrieco-Nauta Conical Blender made commercially available by Hosakawa.

In another aspect, the invention may encompass pharmaceutical formulations formed according to various processes set forth herein.

Medicaments, for the purposes of the invention, include a variety of pharmaceutically active ingredients, such as, for example, those which are useful in inhalation therapy. In general, the term "medicament" is to be broadly construed and include, without limitation, actives, drugs and bioactive agents, as well as biopharmaceuticals. Various embodiments may include medicament present in micronized form. Appropriate medicaments may thus be selected from, for example, analgesics, (e.g., codeine, dihydromorphine, ergotamine, fentanyl or morphine); anginal preparations, (e.g., diltiazem); antiallergics, e.g., cromoglicate, ketotifen or nedocromil); antiinfectives (e.g., cephalosporins, penicillins, streptomycin, sulphonamides, tetracyclines and pentamidine); antihistamines, (e.g., methapyrilene); anti-inflammatories, (e.g., beclometasone dipropionate, fluticasone propionate, flunisolide, budesonide, rofleponide, mometasone furoate, ciclesonide, triamcinolone acetonide, 6α, 9α-difluoro-11β-hydroxy-16α-methyl-3-oxo-17α-propionyloxy-androsta-1, 4-diene-17β-carbothioic acid S-(2-oxo-tetrahydro-furan-3-yl) ester), (6α, 11β, 16α, 17β)-6,9-difluoro-17-{[(fluoromethyl)thio]carbonyl}-11-hydroxy-16-methyl-3-oxoandrosta-1,4-dien-17-yl 2-furoate, and (6α, 11β, 16α, 17α)-6,9-difluoro-17-{[(fluoromethyl)thio]carbonyl}-11-hydroxy-16-methyl-3-oxoandrosta-1,4-dien-17-yl 4-methyl-1,3-thiazole-5-carboxylate); antitussives, (e.g., noscapine); bronchodilators, e.g., albuterol (e.g. as sulphate), salmeterol (e.g. as xinafoate), ephedrine, adrenaline, fenoterol (e.g as hydrobromide), formoterol (e.g., as fumarate), isoprenaline, metaproterenol, phenylephrine, phenylpropanolamine, pirbuterol (e.g., as acetate), reproterol (e.g., as hydrochloride), rimiterol, terbutaline (e.g., as sulphate), isoetharine, tulobuterol,4-hydroxy-7-[2-[2-[[3-(2-(henylethoxy)propyl]sulfonyl]ethyl]-amino]ethyl-2(3H)-benzothiazolone), 3-(4-{[6-({(2R)-2-hydroxy-2-[4-hydroxy-3-(hydroxymethyl)phenyl]ethyl}amino)hexyl]oxy}butyl)benzenesulfonamide, 3-(3-{[7-({(2R)-2-hydroxy-2-[4-hydroxy-3-(hydroxymethyl)phenyl]ethyl}amino)heptyl]oxy}propyl)benzenesulfonamide, 4-{(1R)-2-[(6-{2-[(2,6-dichlorobenzyl)oxy]ethoxy}hexyl)amino]-1-hydroxyethyl}-2-(hydroxymethyl)phenol, 2-hydroxy-5-((1R)-1-hydroxy-2-{[2-(4-{[(2R)-2-hydroxy-2-phenylethyl]amino}phenyl)ethyl]amino}ethyl)phenylformamide, 8-hydroxy-5-{(1R)-1-hydroxy-2-[(2-{4-[(6-methoxy-1,1'-biphenyl-3-yl)amino]phenyl}ethyl)amino]ethyl}quinolin-2(1H)-one, 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one; diuretics, (e.g., amiloride, anticholinergics, e.g., ipratropium (e.g., as bromide), tiotropium, atropine or oxitropium); hormones, (e.g., cortisone, hydrocortisone or prednisolone); xanthines, (e.g., aminophylline, choline theophyllinate, lysine theophyllinate or theophylline); therapeutic proteins and peptides, (e.g., insulin). It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament. It will be further clear to a person skilled in the art that where appropriate, the medicaments may be used in the form of a pure isomer, for example, R-salbutamol or RR-formoterol.

Particular medicaments for administration using pharmaceutical formulations in accordance with the invention include anti-allergics, bronchodilators, beta agonists (e.g., long-acting beta agonists), and anti-inflammatory steroids of use in the treatment of respiratory conditions as defined herein by inhalation therapy, for example cromoglicate (e.g. as the sodium salt), salbutamol (e.g. as the free base or the sulphate salt), salmeterol (e.g. as the xinafoate salt), bitolterol, formoterol (e.g. as the fumarate salt), terbutaline (e.g. as the sulphate salt), reproterol (e.g. as the hydrochloride salt), a beclometasone ester (e.g. the dipropionate), a fluticasone ester (e.g. the propionate), a mometasone ester (e.g., the furoate), budesonide, dexamethasone, flunisolide, triamcinolone, tripredane, (22R)-6α,9α-difluoro-11β,21-dihydroxy-16α, 17α-propylmethylenedioxy-4-pregnen-3,20-dione. Medicaments useful in erectile dysfunction treatment (e.g., PDE-V inhibitors such as vardenafil hydrochloride, along with alprostadil and sildenafil citrate) may also be employed. It should be understood that the medicaments that may be used in conjunction with the inhaler are not limited to those described herein.

Salmeterol, especially salmeterol xinafoate, salbutamol, fluticasone propionate, beclomethasone dipropionate and physiologically acceptable salts and solvates thereof may be employed.

It will be appreciated by those skilled in the art that the formulations according to the invention may, if desired, contain a combination of two or more medicaments. Formulations containing two active ingredients are known for the treatment and/or prophylaxis of respiratory disorders such as asthma and COPD, and may include, for example, formoterol (e.g. as the fumarate) and budesonide, salmeterol (e.g. as the xinafoate salt) and fluticasone (e.g. as the propionate ester), salbutamol (e.g. as free base or sulphate salt) and beclometasone (as the dipropionate ester).

In one embodiment, a particular combination that may be employed is a combination of a beta agonist (e.g., a long-acting beta agonist) and an anti-inflammatory steroid. One embodiment encompasses a combination of fluticasone propionate and salmeterol, or a salt thereof (particularly the xinafoate salt). The ratio of salmeterol to fluticasone propionate in the formulations according to the present invention is preferably within the range 4:1 to 1:20. The two drugs may be administered in various manners, simultaneously, sequentially, or separately, in the same or different ratios. In various embodiments, each metered dose or actuation of the inhaler will typically contain from 25 μg to 100 μg of salmeterol and from 25 μg to 500 μg of fluticasone propionate. The pharmaceutical formulation may be administered as a formulation according to various occurrences per day. In one embodiment, the pharmaceutical formulation is administered twice daily.

Embodiments of specific medicament combinations that may be used in various pharmaceutical formulations are as follows:

1) fluticasone propionate 100 μg/salmeterol xinafoate 72.5 μg (equivalent to salmeterol base 50 μg)

2) fluticasone propionate 250 μg/salmeterol xinafoate 72.5 μg (equivalent to salmeterol base 50 μg)

3) fluticasone propionate 500 μg/salmeterol xinafoate 72.5 μg (equivalent to salmeterol base 50 μg)

In various embodiments, the pharmaceutical formulations may be present in the form of various inhalable formulations. In one embodiment, the pharmaceutical formulation is present in the form of a dry powder formulation, the formulation of such may be carried out according to known techniques. The invention also encompasses inhalation devices including inhalable formulations. Dry powder formulations for topical delivery to the lung by inhalation may, for example, be presented in capsules and cartridges of for example gelatine, or blisters of for example laminated aluminum foil, for use in an inhaler or insufflator. Powder blend formulations generally contain a powder mix for inhalation of the compound of the invention and a suitable powder base which includes lactose and, optionally, at least one additional excipient (e.g., carrier, diluent, etc.). In various embodiments, each capsule or cartridge may generally contain between 20 μg and 10 mg of the at least one medicament. In one embodiment, the formulation may be formed into particles comprising at least one medicament, and excipient material(s), such as by co-precipitation or coating. When employed as a dry powder, packaging of the formulation may be suitable for unit dose or multi-dose delivery. In the case of multi-dose delivery, the formulation can be pre-metered (e.g., as in Diskus®, see GB 2242134/U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g. as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet hermetically but peelably sealed thereto to define a plurality of containers, each container having therein an inhalable formulation containing the at least one medicament, the lactose, optionally with other excipients. Preferably, the strip is sufficiently flexible to be wound into a roll. The lid sheet and base sheet will preferably have leading end portions which are not sealed to one another and at least one of the leading end portions is constructed to be attached to a winding means. Also, preferably the hermetic seal between the base and lid sheets extends over their whole width. The lid sheet may preferably be peeled from the base sheet in a longitudinal direction from a first end of the base sheet.

In one embodiment, the formulations may be employed in or as suspensions or as aerosols delivered from pressurised packs, with the use of a suitable propellant, e.g. dichlorodifluoromethane, trichlorofluoromethane, dichlorotetrafluoroethane, 1,1,1,2,3,3,3-heptafluoropropane, 1,1,1,2-tetrafluoroethane, carbon dioxide or other suitable gas. Such formulations may be delivered via a pressurized inhaler, e.g., a Metered Dose Inhaler (MDI). Exemplary MDIs typically include canisters suitable for delivering the pharmaceutical formulations. Canisters generally comprise a container capable of withstanding the vapour pressure of the propellant used such as a plastic or plastic-coated glass bottle or preferably a metal can, for example an aluminum can which may optionally be anodised, lacquer-coated and/or plastic-coated, which container is closed with a metering valve. Aluminum cans which have their inner surfaces coated with a fluorocarbon polymer are particularly preferred. Such polymers can be made of multiples of the following monomeric units: tetrafluoroethylene (PTFE), fluorinated ethylene propylene (FEP), perfluoroalkoxyalkane (PFA), ethylene tetrafluoroethylene (EFTE), vinyldienefluoride (PVDF), and chlorinated ethylene tetrafluoroethylene. Embodiments of coatings used on all or part of the internal surfaces of an MDI are set forth in U.S. Pat. Nos. 6,143,277; 6,511,653; 6,253,762; 6,532,955; and 6,546,928.

MDIs may also include metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK356) and 3M-Neotechnic Ltd, UK (e.g. Spraymiser™). Embodiments of metering valves are set forth in U.S. Pat. Nos. 6,170,717; 6,315,173; and 6,318,603.

In various embodiments, the MDIs may also be used in conjunction with other structures such as, without limitation, overwrap packages for storing and containing the MDIs, including those described in U.S. Pat. No. 6,390,291, as well as dose counter units such as, but not limited to, those described in U.S. Pat. Nos. 6,360,739 and 6,431,168.

In addition to the above, the pharmaceutical formulations can be employed in capsules, sachets, tablet buccals, lozenges, papers, or other container. Moreover, the formulations can be in the form of tablets, pills, powders, elixirs, suspensions, emulsions, solutions, syrups, capsules (such as, for example, soft and hard gelatin capsules), suppositories, sterile injectable solutions, and sterile packaged powders. Excipients, carriers, diluents, and the like may be optionally employed.

The pharmaceutical formulation formed by the processes of the invention may be used in the treatment of a number of respiratory disorders, which encompasses, for example, maintenance treatment and/or prophylaxis. Such respiratory conditions include, without limitation, diseases and conditions associated with reversible airways obstruction such as asthma, chronic obstructive pulmonary diseases (COPD) (e.g. chronic and wheezy bronchitis, emphysema), respiratory tract infection and upper respiratory tract disease (e.g. rhinitis, such as allergic and seasonal rhinitis). Such treatment is carried out by delivering medicament to a mammal. Accordingly, and in view of the above, in another aspect, the invention provides a method for the treatment of a respiratory disorder comprising the step of administering a pharmaceutically effective amount of a pharmaceutical formulation to a mammal such as, for example, a human. For the purposes of the invention, the term "pharmaceutically effective amount" is to be broadly interpreted and encompass the treatment of the disorder. In one embodiment, the administration is carried out via an inhalation device described herein. In one embodiment, the administration is carried out by nasal or oral inhalation.

The invention offers potential advantages relative to the prior art. As one example, the invention allows for improved control of particle size distribution of the lactose formed by this process, i.e., a more consistent particle size distribution and/or a more consistent surface morphology of the lactose is capable of being achieved from lactose feeds independent of the particle size distribution of the lactose feed. In particular, the lactose formed by the process of the invention is capable of exhibiting a more continuous particle size distribution, i.e., very little or no gap in the particle size distribution in contrast to the distribution set forth in X. M. Zeng et al., *International Journal of Pharmaceutics*, 176 (1998) 99-110.

The present invention is highly advantageous. In one embodiment, for example, the classification cut-point can be chosen so that the coarse fraction is suitable for use in a pharmaceutical formulation without fine fraction. In one embodiment, at least a portion of the fine fraction (ranging from 0, 5, 10, 15, 20, 25, 30, 35, 40, or 45 to 55, 60, 65, 70, 75, 80, 85, 90, 95 or 100 percent by weight) may be combined (e.g., blended) with at least a portion of the coarse fraction (ranging from 0, 5, 10, 15, 20, 25, 30, 35, 40, or 45 to 55, 60, 65, 70, 75, 80, 85, 90, 95 or 100 percent by weight) such that the resulting lactose composition is suitable for use in a pharmaceutical formulation. In one embodiment, the fine fraction may be used in a pharmaceutical formulation without any coarse fraction. With respect to the above embodiments, it is preferred that lactose be employed with sufficient fine material so as to be capable of meeting the FPMass requirements, typically 20 percent to 30 percent (weight basis) of the medicament content achieved by utilising lactose that comprises 2 percent to 10 percent (volume basis) particles less than 4.5 microns as measured by Sympatec.

In view of the above, in one embodiment, the invention may further comprise combining at least one medicament with a lactose composition to form a pharmaceutical formulation. The lactose composition in such an embodiment may comprise from 0, 5, 10, 15, 20, 25, 30, 35, 40, or 45 to 55, 60, 65, 70, 75, 80, 85, 90, 95 or 100 percent by weight of the coarse fraction and from 0, 5, 10, 15, 20, 25, 30, 35, 40, or 45 to 55, 60, 65, 70, 75, 80, 85, 90, 95 or 100 percent by weight of the fine fraction. Moreover, in one embodiment, the invention may further comprise combining at least a portion of the coarse fraction with at least a portion of the fine fraction to form a lactose composition; and thereafter combining the lactose composition with at least one medicament to form a pharmaceutical formulation. Alternatively, in one embodiment, the invention may encompass simultaneously combining: (i) from 0, 5, 10, 15, 20, 25, 30, 35, 40, or 45 to 55, 60, 65, 70, 75, 80, 85, 90, 95 or 100 percent by weight of coarse fraction, (ii) from 0, 5, 10, 15, 20, 25, 30, 35, 40, or 45 to 55, 60, 65, 70, 75, 80, 85, 90, 95 or 100 percent by weight of fine fraction, and (iii) at least one medicament to form a pharmaceutical formulation.

As the large majority of the small particles have been produced by milling, they all typically possess a similar surface roughness. By comparison, if lactose batches are introduced into the mill that contain particles less than a volume average size of 70 microns, then these particles will essentially pass through the mill without the need to be reduced in size by the milling action. As a consequence, these particles will still exhibit a smoother crystalline surface, compared to milled lactose particles, which in turn may lead to different interactions with the active molecules.

Thus by substantially reducing or eliminating these small crystalline particles from the feed to the mill, not only can the milled particle size be controlled, but the particles will also exhibit a very much more uniform surface morphology.

Malvern Methodology

Malvern measurements as set forth herein are determined according to the following:

Equipment

Malvern Mastersizer, laser diffraction particle size analyser fitted with the 300 mm focal length lens.
MS15 stainless steel flow-through measurement cell, 2.2 mm path width (Malvern).
MSX1 small volume presentation unit (Malvern).
Viton tubing: 4.8 mm internal diameter, 1.6 mm wall thickness (Watson-Marlow).
Viton or Neoprene tubing: approximately 15 mm internal diameter, 2 mm wall thickness (Watson-Marlow).
Positive pressure or vacuum filtration equipment with 0.22 µm maximum aperture membrane filters type GV (Sartorius/Millipore).
Analytical balance (Mettler, electronic) minimum weighing capacity of 30 grams with an accuracy to 4 decimal places, Spatulas for sample transfer.
Solvent: HPLC grade iso-octane Test Method This section outlines the procedure for the measurement of one batch of lactose. For each batch, it is preferred that three representative samples be measured in duplicate.

Preparation of the Liquid Dispersant.

For the preparation of 2 liters of liquid dispersant, dissolve with ultrasonication 0.7 g of lecithin NF in 10 cm$^3$ of iso-octane to produce a dispersant concentrate.
Filter sufficient iso-octane using the vacuum filtration unit and a 0.22 µm filter disc. During this filtration add the dispersant concentrate to the solvent so that it too is filtered and mixed in. Store in a pre-cleaned Winchester solvent container (Liquid dispersant).
The filtered liquid dispersant should be stored in a solvent cupboard when not in use.
Liquid dispersant may be recycled by refiltering after analysis as from above and making up to volume with iso-octane Preparation of the Malvern Mastersizer Set up the following measurement parameters on the Malvern Mastersizer for the test sample:

| | |
|---|---|
| Model type: | Model independent |
| Presentation code: | 0503 |
| Focal length: | 300 mm |
| Beam active length: | 2.2 mm |
| Gain: | Low |
| Trigger: | Internal |
| Kill data low: | 0 |
| Kill data high: | 0 |
| Shape correction: | Off |
| Density: | 1.00 |
| Autorun number: | 0 |
| Obscuration range: | Between 0.18 and 0.22 |
| Sweeps for measure: | 1000 |
| Sweeps for inspect: | 50 |

Set up the MSX1 small volume presentation unit ensuring that the total length Viton tubing from the presentation unit to the flow through cell does not exceed 30 cm. Attach one end of suitably sized (int. dia. approx. 15 mm) Viton or Neoprene tubing (waste tubing) to the waste drain and place the other end into a red non-chlorinated waste solvent container placed on the floor.
Flush the presentation unit and the cell through with the liquid dispersant and drain.
Refill with the iso-octane/lecithin dispersant and align the laser beam using a stirrer speed of 11 o'clock (1500±100 rpm). The laser intensity should be in the "good" region.
Once the laser is aligned, it is preferred that the stirrer speed should not be altered.

Sample Measurement

Add the powder sample to a presentation unit using a spatula to obtain an obscuration value within the range 0.18 to 0.22.
Allow 60 seconds to allow the dispersion to equilibrate and the obscuration value to stabilise.

Measure the particle size distribution. Repeat measurement as deemed appropriate.

Sympatec Methodology

The following teachings may be employed to arrive at the Sympatec measurements described herein:

Instrumental Parameters

| Parameter | Typical |
|---|---|
| Measuring Range | R5: 0.5/4.5→875 μm |
| Trigger Conditions | 10 s, 100 ms, 0.2% ch12 |
| Time Base | 100 ms |
| Reference measurement | 10 s, Single |
| Focus Prior to first measurement | No |
| Start | 0 s after channel 12 ≥ 0.2% |
| Valid | Always |
| Stop | 5 s after channel 12 ≤ 0.2% |
| Or After | 30 s real time |
| Dispersing Device | RODOS |
| VIBRI Chute | Standard chute |
| Gap Width | 2 mm |
| Pressure | Nominal 1.5 Bar (1.3-1.7 Bar acceptable) |
| Depression | Maximise (see LSOP/WARE/092/03 section 5.2.9). |
| Feed Rate | 85% |
| Sample Weight | 2 g ± 1 g |

The Sympatec HELOS is provided with the RODOS dry powder dispersion unit and the VIBRI vibratory feeder.

In these measurements, software is used in conjunction with the measurement equipment.

For the RODOS dispersing system, the primary pressure of the injector should be adjusted using the pressure control dial. The primary pressure should be within the range 1.3-1.7 bar although a pressure of 1.5 bar should be aimed for at each run. The injector depression should be optimised using the adjustment ring. The direction in which the adjuster ring is turned (clockwise or anti clockwise), has no adverse effect on the depression obtained. On instruments with a RODOS/M dispersing system, the primary pressure may be adjusted using a software algorithm. The injector depression should be maximised by clicking the "Auto-adjust depr" button. The instrument should not be used if the injector depression is less than 55 mbar at 1.3-1.7 bar.

Analysis of Sample

Homogenize the sample by turning the pot slowly end-over-end at least ten times in one direction and ten times in the other direction prior to analysis. This is only necessary the first time a sample is taken from a pot.

Transfer 2±1 g of the lactose sample into the funnel attached to the VIBRI using a Kartell "spoon/flat" general purpose spatula (Fisher catalogue no SMJ-410-091M, volume approximately 1.8 cm$^3$).

A heaped spoonful of lactose powder has been demonstrated to present a sample in the range 2.0-3.0 g.

The invention will now be described with respect to the following examples. It should be appreciated that the examples are set forth for illustrative purposes only, and do not limit the scope of the invention as defined by the claims.

EXAMPLE 1

Lactose Processing

Two batches of coarse crystalline lactose A were selected. These differed from each other inasmuch that they exhibited different D50's. Batch 1 had a D50 of between 110-130 microns and Batch 2 had a D50 of between 160-180 microns, as measured by Malvern laser particle sizing techniques.

Each of these batches were then separated into a fine and coarse fraction using an air classifier. The cut point was nominally about 80 microns.

In each case the fine fraction was discarded and the coarse fractions were milled in an air classifier mill (ACM) so that the D50 of the milled product was nominally 60-70 microns.

The milled lactose batches were then classified at a cut point of nominally 25 microns to form a fine fraction and a coarse fraction.

Suitable proportions of the coarse and fine fraction from each milled batch were blended together so that the percentage of lactose <4.5 microns was:

(i) 6.7%+/−0.3%; ex batch 1
(ii) 5.0%+/−0.3%; ex batch 11
(iii) 3.3%+/−0.3%; ex batch 1
(iv) 6.7%+1-0.3%; ex batch 2
(v) 5.0%+/−0.3%; ex batch 2
(vi) 3.3%+/−0.3%; ex batch 2

The above teachings are exemplified by the following protocol:

The purpose of the following development protocol is to manufacture lactose batches having the same overall particle size distribution from different feed crystalline lactose A batches.

The feed, milling, classifying, and blending of lactose may be carried out using the following:

1) A pilot scale blender capable of blending 100 kg of material ("pilot scale blender")
2) A full scale classifier, e.g., a classifier that may be employed as a stand alone device suitable for full scale production ("full scale classifier")

The following experimental method may be employed:

1. Select 2 batches of crystalline lactose A that are different from each other in their percentage of lactose that is less than 80 microns. Crystalline Lactose A is employed as feed lactose and is made commercially available by Borculo Domo Ingredients of Borculo, Netherlands.

These are defined as batch 1, which has a D50 of between 120-130 microns and batch 2 that has a D50 of 170-180 microns. Batch 1 should have the percentage less than 15 microns greater than 3%, whereas batch 2 should have the percentage of lactose less than 15 microns as less than 1.5%.

2. Using the full scale classifier, separate each full batch as cleanly as possible into two fractions, one being <80 microns and the other being >80 microns. The same settings should be used for both batches and it is desirable that no changes are to be made to the settings during the classification.

3. Mill only the fraction of lactose that is >80 microns from both batches 1 and 2. Set the mill at nominally the same as used for commercial supply however, reduce the throughput rate of the lactose so that the milling and built in classifier can act more efficiently. Once set, discard any test millings and then mill each batch of lactose >80 microns at the same settings.

4. Using the full scale classifier, separate each milled batch as cleanly as possible into two fractions, one being nominally <25 microns and the other being nominally >25 microns. The same settings should be used for both batches and it is desirable no changes are to be made to the settings during the classification.

5. Recombination by blending: Using appropriate aliquots from each batch of the classified fractions, recombine the lactose in the pilot scale blender to give:

a—100 kgs of product which has the percentage of lactose <4.5 microns at 6.7%+/−0.3%—From feed batch 1 b—100 kgs of product which has the percentage of lactose <4.5 microns at 5.0%+/−0.3%—From feed batch 1 c—100 kgs of product which has the percentage of lactose <4.5 microns at 3.3%+/−0.3%—From feed batch 1

This may be repeated using lactose from the second feed batch. (d) should be as similar to (a) as possible.

d—100 kgs of product which has the percentage of lactose <4.5 microns at 6.7%+/−0.3%—From feed batch 2 e—100 kgs of product which has the percentage of lactose <4.5 microns at 5.0%+/−0.3%—From feed batch 2 f—100 kgs of product which has the percentage of lactose <4.5 microns at 3.3%+/−0.3%—From feed batch 2

6. Dispense lactose from blender into 20 kg tie sealed polyethylene bags, heat sealed in a foil laminate bag and pack inside a cardboard box. Pack at least 5 boxes from each batch.

EXAMPLE 2

Lactose Processing

Two batches of coarse crystalline lactose A were selected. These differed from each other inasmuch that they exhibited different D50's. Batch 1 had a D50 of between 110-130 microns and Batch 2 had a D50 of between 160-180 microns, as measured by Malvern laser particle sizing techniques.

Each of these batches were then separated into a fine and coarse fraction using an air classifier. The cut point was nominally about 80 microns.

In each case the fine fraction was discarded and the coarse fractions were milled in an air classifier mill (ACM) so that the D50 of the milled product was nominally 60-70 microns.

Both milled lactose batches were then put through a 150 micron sieve. This is an additional step compared to Example 1.

The milled lactose batches were then classified at a cut point of nominally 25 microns to form a fine fraction and a coarse fraction.

Suitable proportions of the coarse and fine fraction from each milled batch were blended together so that the percentage of lactose <4.5 microns was:
(i) 6.7%+/−0.3%; ex batch 1
(ii) 5.0%+/−0.3%; ex batch 1
(iii) 3.3%+/−0.3%; ex batch 1
(i) 6.7%+1-0.3%; ex batch 2
(ii) 5.0%+/−0.3%; ex batch 2
(iii) 3.3%+/−0.3%; ex batch 2

The unit operation of this protocol pertains to the process of classification of feed, milling, classifying, sieving, and blending of lactose.

The following equipment may be used:
pilot scale blender
full scale classifier

The purpose of this example is to manufacture lactose batches with the same overall particle size distribution from different feed batches. This work will use the Full Scale Classifier.

The above teachings are exemplified by the following protocol:

1. Select two batches of crystalline lactose A, batch 1 that has a D50 of 120-130 microns, and the percentage lactose less than 15 microns is greater than 3%, and batch 2 with an D50 of 170-180 microns and the percentage lactose less than 15 microns is less than 1.5%. For the purposes of this protocol however, the D50 range was altered such that the batch 1 D50 was from 110-130 microns and the batch 2 D50 was from 160-180 microns.

Treat each of these big bags in an identical fashion as described in stages 2 through to 5.

2. Using the full scale classifier, separate the whole batch as cleanly as possible into two fractions, one being <80 microns and the other being >80 microns. The same settings should be used as those used in Example 1 and it is desirable that no changes be made to the settings during the classification.

3. Mill the coarse fraction obtained from 2. Set the mill at nominally the same as used for typical lactose milling. Once the mill is set, discard any test millings and then mill the coarse fractions from the batch at the same settings.

4. Sieve the milled material through a 150-micron sieve.

5. Using the full scale classifier, separate each sieved milled batch as cleanly as possible into two fractions, one being nominally <25 microns and the other being nominally >25 microns. These settings should remain constant during the classification of the batch.

6. Recombination by blending: Using appropriate coarse and fine aliquots from batches 1 and 2 at the end of stage 5, recombine the lactose in the pilot scale blender to give:
a—100 kgs of product which has the percentage of lactose <4.5 microns at 6.7%+/−0.3%—(batch 1, Fine Feed)
b—100 kgs of product which has the percentage of lactose <4.5 microns at 6.7%+/−0.3%—(batch 2, Coarse Feed)

No Targets for the D50 are given for these recombinations, 60-90 microns would be ideal.

7. Dispense lactose from blender into 20 kg tie sealed polythene bags, heat sealed in a foil laminate bag and pack inside a cardboard box. Pack at least 5 boxes from each batch.

EXAMPLE 3

Lactose Processing

Two batches of coarse crystalline lactose A were selected. These differed from each other inasmuch that they exhibited different D50's. Batch 1 had a D50 of between 110-130 microns and Batch 2 had a D50 of between 160-180 microns, as measured by Malvern laser particle sizing techniques.

Each of these batches were then separated into a fine and coarse fraction using an air classifier. The cut point was nominally about 80 microns.

In each case the fine fraction was discarded and the coarse fractions were milled in an air classifier mill (ACM) so that the D50 of the milled product was nominally 60-70 microns.

The milled lactose batches were then classified at a cut point of nominally 25 microns to form a fine fraction and a coarse fraction.

Suitable proportions of the coarse and fine fraction from each milled batch were blended together so that the percentage of lactose <4.5 microns was:
(i) 6.3%+1-0.3%; ex batch 1
(ii) 6.0%+/−0.3%; ex batch 1
(iii) 5.5%+/−0.3%; ex batch 1
(i) 6.3%+/−0.3%; ex batch 2
(ii) 6.0%+/−0.3%; ex batch 2
(iii) 5.5%+/−0.3%; ex batch 2

The above teachings are exemplified by the following protocol:

The unit operation of this protocol pertains to the process of classification of feed, milling, classifying, sieving, and blending of lactose.

The purpose of the protocol set forth in this example is to manufacture lactose batches with the same overall particle size distribution from different feed batches. This work will use the full scale classifier.

The protocol is as follows:

1. Select two batches of crystalline lactose A, batch 1 that has a D50 of 120-130 microns, and the percentage lactose less than 15 microns is greater than 3%, and batch 2 with an D50 of 170-180 microns and the percentage lactose less than 15 microns is less than 1.5%. For the purposes of this protocol however, the D50 range was altered such that the batch 1 D50 was from 110-130 microns and the batch 2 D50 was from 160-180 microns.

Treat each of these big bags in an identical fashion as described in stages 2 through to 4.

2. Using the full scale classifier, separate the whole batch as cleanly as possible into two fractions, one being <80 microns and the other being >80 microns. The same settings should be used as those used in Example 2, these are shown in Table 3 below. It is preferable that no changes are to be made to the settings during the classification.

TABLE 3

| | Settings | Readings | Calculated |
|---|---|---|---|
| Classifierspeed | 4.1 Hz | 246 rpm | |
| Feedrate | 15 Hz | 12 Rpm | 250 Kg/hour |
| Transport air | 1500 Rpm 25 Hz | min 135 m3/h | |
| | | max 165 m3/h | |
| Washair | 1500 Rpm 25 Hz | min 390 m3/h | |
| | | max 450 m3/h | |

3. Using the full scale classifier with the settings in Table 4, separate each milled batch as cleanly as possible into two fractions, one being nominally <25 microns and the other being nominally >25 microns.

TABLE 4

| | Settings | Readings | Calculated |
|---|---|---|---|
| Classifierspeed | 10 Hz | 600 rpm | |
| Feedrate | 25 Hz | 20 Rpm | 410 KG/hour |
| Transport air | | min 175 m3/h | |
| | | max 235 m3/h | |
| Washair | | min 620 m3/h | |
| | | max 675 m3/h | |
| Airsystem | 2100 Rpm 35 Hz | | |

The above settings are capable of providing batches that are approximately 80% wt/wt coarse material and 20% wt/wt fine material.

4. Recombination by blending: Using appropriate coarse and fine aliquots from batches 1 and 2 at the end of stage 3, recombine the lactose in the pilot scale blender to give:

a—100 kgs of product which has the percentage of lactose <4.5 microns at 6.3%+/−0.3%—From feed batch 1 b—100 kgs of product which has the percentage of lactose <4.5 microns at 6.0%+1-0.3%—From feed batch 1 c—100 kgs of product which has the percentage of lactose <4.5 microns at 5.5%+/−0.3%—From feed batch 1

This to be repeated using lactose from the second feed batch.

d—100 kgs of product which has the percentage of lactose <4.5 microns at 6.3%+/−0.3%—From feed batch 2 e—100 kgs of product which has the percentage of lactose <4.5 microns at 6.0%+/−0.3%—From feed batch 2 f—100 kgs of product which has the percentage of lactose <4.5 microns at 5.5%+/−0.3%—From feed batch 2

Use the same amounts of fines and coarse in each pair of the combinations.

Ensure data on Malvern and Sympatec sheets agree with data in the table.

TABLE 5

Particle Size Data for Typical Lactose Production

| | Fine fraction | | | | | | Coarse fraction | |
|---|---|---|---|---|---|---|---|---|
| Batch number | D10 fine | D50 fine | D90 fine | 15 μm fine | D10 Coarse | D50 Coarse | D90 Coarse | % 15 μm coarse |
| Normal Production Data | | | | | | | | |
| 1 | 7.9 | 23 | 53 | 30.5 | 29 | 84 | 183 | 4.5 |
| 2 | 6.9 | 19 | 43 | 38.9 | 29 | 79 | 169 | 4.7 |
| 3 | 6.6 | 20 | 51 | 38.5 | 27 | 81 | 161 | 5.8 |
| 4 | 7.6 | 20 | 53 | 36.4 | 25 | 77 | 151 | 5.6 |
| 5 | 6.6 | 18 | 44 | 42.7 | 31 | 82 | 160 | 6.5 |
| 6 | 7.7 | 24 | 51 | 29.9 | 46 | 92 | 168 | 1 |
| 7 | 7.9 | 21 | 48 | 32.5 | 45 | 92 | 169 | 1 |
| 8 | 8.2 | 24 | 52 | 28 | 40 | 79 | 143 | 1.5 |
| 9 | 8.3 | 25 | 57 | 27.3 | 46 | 93 | 167 | 1.3 |
| 10 | 7.2 | 20 | 48 | 34.7 | 34 | 84 | 138 | 2.5 |
| 11 | 7.3 | 20 | 47 | 35.1 | 46 | 97 | 184 | 1 |
| 12 | 7 | 18 | 34 | 39.6 | 46 | 104 | 205 | 1 |
| 13 | 7.4 | 19 | 42 | 36.9 | 48 | 101 | 184 | 0.9 |
| 14 | 7.7 | 19 | 40 | 36.5 | 47 | 101 | 191 | 0.7 |
| 15 | 7.7 | 19 | 40 | 36.5 | 46 | 102 | 200 | 0.8 |
| 16 | 7.8 | 21 | 47 | 32.2 | 46 | 94 | 175 | 0.8 |
| 17 | 7.5 | 22 | 56 | 32.2 | 47 | 94 | 171 | 0.5 |
| 18 | 7.5 | 22 | 56 | 32.2 | 48 | 94 | 171 | 0.5 |
| 19 | 6.5 | 20 | 45 | 35 | 29 | 88 | 184 | 4.6 |
| 20 | 6.5 | 20 | 45 | 38.1 | 52 | 102 | 185 | 0.6 |
| 21 | 6.5 | 20 | 46 | 38.5 | 48 | 97 | 188 | 1 |
| 22 | 6.5 | 19 | 42 | 38.7 | 47 | 105 | 202 | 1.2 |
| 23 | 7.3 | 21 | 45 | 33.7 | 50 | 100 | 180 | 0.9 |
| 24 | 7.1 | 20 | 44 | 34.9 | 46 | 92 | 169 | 1.3 |
| 25 | 6.9 | 20 | 43 | 37.4 | 48 | 95 | 170 | 0.9 |
| 26 | 5.8 | 21 | 49 | 36.9 | 39 | 83 | 158 | 2.4 |
| 27 | 5.9 | 21 | 51 | 36.4 | 40 | 82 | 157 | 2.2 |

TABLE 5-continued

Particle Size Data for Typical Lactose Production

| Batch number | Fine fraction | | | | Coarse fraction | | | |
|---|---|---|---|---|---|---|---|---|
| | D10 fine | D50 fine | D90 fine | 15 μm fine | D10 Coarse | D50 Coarse | D90 Coarse | % 15 μm coarse |
| 28 | 5.7 | 20 | 45 | 38.9 | 43 | 91 | 174 | 1.97 |
| 29 | 6.9 | 23 | 54 | 32 | 34 | 92 | 185 | 3.2 |
| 30 | 6.9 | 23 | 54 | 32.3 | 33 | 91 | 184 | 3.8 |
| 31 | 6.1 | 22 | 50 | 35.19 | 51 | 99 | 181 | 0.75 |
| 32 | 6.4 | 22 | 49 | 34.7 | 50 | 97 | 180 | 0.9 |
| 33 | 6.9 | 24 | 58 | 31.37 | 50 | 95 | 176 | 0.91 |
| 34 | 6.9 | 18 | 36 | 40 | 46 | 100 | 198 | 0.2 |
| 35 | 6.5 | 18 | 40 | 40 | 42 | 84 | 158 | 1.1 |
| 36 | 6.3 | 18 | 44 | 40 | 40 | 81 | 154 | 1.5 |
| 37 | 6.8 | 19 | 43 | 39 | 43 | 84 | 158 | 1.1 |
| 38 | 6 | 18 | 42 | 42 | 40 | 81 | 155 | 1.4 |
| 39 | 6 | 18 | 41 | 42 | 42 | 88 | 168 | 1.5 |
| 40 | 7 | 19 | 43 | 38 | 44 | 93 | 182 | 0.8 |
| 41 | 6.7 | 19 | 42 | 39 | 44 | 94 | 184 | 0.8 |
| 42 | 6.2 | 18 | 40 | 43 | 42 | 90 | 180 | 1 |
| 43 | 6 | 17 | 40 | 43 | 41 | 85 | 168 | 1.3 |
| 44 | 6.4 | 18 | 40 | 41 | 42 | 85 | 165 | 1 |
| 45 | 6.9 | 17 | 37 | 42 | 40 | 82 | 161 | 1 |
| 46 | 6.9 | 18 | 40 | 41 | 40 | 82 | 162 | 0.9 |
| 47 | 6.6 | 17 | 40 | 42 | 38 | 87 | 177 | 1.2 |
| 48 | 6.8 | 18 | 45 | 40 | 38 | 85 | 173 | 1.2 |
| 49 | 6.4 | 17 | 37 | 45 | 41 | 86 | 170 | 1.2 |
| 50 | 6.1 | 15 | 33 | 48 | 41 | 92 | 187 | 1 |
| 51 | 6.6 | 17 | 37 | 44 | 41 | 87 | 167 | 1 |
| 52 | 5.8 | 15 | 33 | 52 | 33 | 86 | 170 | 2.3 |
| 53 | 6 | 14 | 32 | 52.3 | 34 | 85 | 167 | 2 |
| 54 | 6.8 | 16 | 38 | 45.8 | 38 | 92 | 173 | 1.4 |
| 55 | 6.6 | 14 | 26 | 57 | 34 | 80 | 156 | 2.3 |
| 56 | 6.8 | 15 | 29 | 51 | 30 | 74 | 147 | 2.8 |
| 57 | 6.3 | 15 | 31 | 51 | 39 | 90 | 170 | 1.6 |
| 58 | 6.6 | 18 | 53 | 43.6 | 40 | 91 | 174 | 1.7 |
| 59 | 7.5 | 20 | 44 | 35.2 | 40 | 88 | 168 | 2.4 |
| 60 | 7.8 | 23 | 51 | 30.3 | 45 | 92 | 166 | 1.7 |
| 61 | 7.5 | 22 | 48 | 33 | 43 | 87 | 158 | 1.8 |
| 62 | 7.4 | 22 | 50 | 32.5 | 44 | 89 | 164 | 1.5 |
| 63 | 7.6 | 22 | 49 | 32.6 | 47 | 97 | 184 | 1.4 |
| 64 | 7.7 | 24 | 53 | 29.6 | 47 | 96 | 186 | 1.1 |
| 65 | 7.5 | 23 | 52 | 31.3 | 45 | 93 | 181 | 1.2 |
| 66 | 7 | 21 | 49 | 34.8 | 46 | 94 | 179 | 1.3 |
| 67 | 6.8 | 20 | 48 | 36.2 | 46 | 96 | 178 | 1.5 |
| 68 | 7.3 | 20 | 44 | 35.8 | 48 | 98 | 178 | 1.3 |
| 69 | 7.1 | 19 | 44 | 37.2 | 48 | 97 | 172 | 1.6 |
| 70 | 6.9 | 20 | 48 | 35.9 | 49 | 98 | 175 | 1.3 |
| 71 | 6.5 | 20 | 45 | 37.9 | 47 | 96 | 173 | 1.5 |
| 72 | 6.6 | 20 | 48 | 36.5 | 47 | 95 | 172 | 1.3 |
| 73 | 6.5 | 21 | 52 | 36.1 | 47 | 95 | 171 | 1.3 |
| Mean | 6.9 | 19.6 | 44.8 | 38.0 | 42.0 | 90.6 | 172.5 | 1.7 |
| Std dev | 0.6 | 2.5 | 6.9 | 5.9 | 6.3 | 7.0 | 13.0 | 1.3 |
| % rsd | 8.9% | 12.7% | 15.4% | 15.6% | 15.0% | 7.8% | 7.5% | 75.3% |
| Pre-Classified Feed Data (Malvern) | | | | | | | | |
| EXAMPLE 1 (Fine) | 7 | 28 | 64 | 27.1 | 52 | 97 | 164 | 2.2 |
| EXAMPLE 1 (Coarse) | 7 | 26 | 55 | 28.8 | 48 | 101 | 189 | 2.5 |
| EXAMPLE 2 (Fine) | 7.3 | 26 | 59 | 28.5 | 49 | 88 | 153 | 1.5 |
| EXAMPLE 2 (Coarse) | 7 | 26 | 59 | 30 | 49 | 93 | 166 | 2 |
| EXAMPLE 3 (Fine) | 7.1 | 27 | 58 | 27.4 | 48 | 87 | 151 | 1.7 |
| EXAMPLE 3 (Coarse) | 7 | 26 | 56 | 29 | 50 | 91 | 157 | 1.6 |
| Mean of examples 1, 2 & 3 | 7.1 | 26.5 | 58.5 | 28.5 | 49.3 | 92.8 | 163.3 | 1.9 |
| Stdev of Examples 1, 2 & 3 | 0.1 | 0.8 | 3.1 | 1.1 | 1.5 | 5.4 | 13.9 | 0.4 |
| RSD of Examples 1, 2 & 3 | 1.7% | 3.2% | 5.4% | 3.8% | 3.1% | 5.8% | 8.5% | 20.2% |
| Mean of Examples 2 & 3 | 7.1 | 26.3 | 58.0 | 28.7 | 49.0 | 89.8 | 156.8 | 1.7 |
| Std Dev. Of Examples 2 & 3 | 0.1 | 0.5 | 1.4 | 1.1 | 0.8 | 2.8 | 6.7 | 0.2 |
| RSD of Examples 2 & 3 | 2.0% | 1.9% | 2.4% | 3.8% | 1.7% | 3.1% | 4.2% | 12.7% |

An important aspect of the parameters described within the protocols illustrated in Examples 1 through 3 is that all initial stages are the same, irrespective of the desired amount of fine lactose in the final product to be manufactured. The varying amounts of fine lactose that are desired are achieved by combining the appropriate proportions of the coarse and fines fractions and not to mill "harder" for the lactose batches that require more fine lactose in the final product. Tables 6 and 7 show the particle size for the feed Batch A crystal by both Malvern and Sympatec, that was used in these trials.

It can be seen from these three examples that all the initial stages are similar, if not identical. The only stage at which there is a change is at the blending stage, in which more fine lactose would be added to achieve the required targets at %<4.5 microns.

Tables 6 and 7 show the particle size data for the both coarse and fine feed crystal lactose used in Examples 1, 2 and 3. (Malvern and Sympatec)

TABLE 6

Particle size data of the feed lactose prior to classification - Malvern

| | Malvern Data | | | |
|---|---|---|---|---|
| Feed Batch | D10 | D50 | D90 | % < 15 microns |
| "Fine" Feed for Example 1 | 57 | 123 | 208 | 2 |
| "Coarse" Feed for Example 1 | 86 | 176 | 284 | 0.8 |
| "Fine" Feed for Example 2 | 53 | 114 | 208 | 1.14 |
| "Coarse" Feed for Example 2 | 84 | 162 | 270 | 0.7 |
| "Fine" Feed for Example 3 | 53 | 114 | 207 | 1.02 |
| "Coarse" Feed for Example 3 | 81 | 161 | 274 | 0.7 |

TABLE 7

Particle size data of the feed lactose prior to classification - Sympatec

| | Malvern Data | | | |
|---|---|---|---|---|
| Feed Batch | D10 | D50 | D90 | % < 4.5 microns |
| "Fine" Feed for Example 1 | 40 | 116 | 188 | 2 |
| "Coarse" Feed for Example 1- | 63 | 165 | 263 | 1.3 |
| "Fine" Feed for Example 2 | 39 | 103 | 180 | 1.3 |
| "Coarse" Feed for Example 2 | 68 | 150 | 239 | 1.0 |
| "Fine" Feed for Example 3 | 38 | 102 | 177 | 1.1 |
| "Coarse" Feed for Example 3 | 65 | 149 | 248 | 1.3 |

Discussion:

A range of feed lactose has been covered by choosing both coarse and fine feed lactose in each of these three examples. They contain varying amounts of lactose that would pass through the mill, essentially un-milled, and end up in packed product.

In each of the examples 1-3, the majority of these small particles are removed by a classification process so that the resultant feed material is much more uniform when presented to the mill. A target was to reduce the amount of lactose particles less than 70 microns to less than 10%. An alternative way of expressing this is that the D10 of the resulting lactose should be greater than 70 microns by Sympatec.

The results from the three examples are shown in Table 8.

TABLE 8

Coarse Fraction from the Crystalline Feed Lactose after initial classification step - Sympatec

| | Sympatec Data | | | |
|---|---|---|---|---|
| | D10 | D50 | D90 | % < 4.5 microns |
| "Fine" Feed for Example 1 after classification | 82 | 135 | 202 | 0.0 |
| "Coarse" Feed for Example 1 after classification | 107 | 177 | 259 | 0.0 |
| "Fine" Feed for Example 2- after classification | 66 | 125 | 202 | 0.6 |
| "Coarse" Feed for Example 2 after classification (Coarse) | 94 | 160 | 240 | 0.2 |
| "Fine" Feed for Example 3 after classification | 67 | 125 | 203 | 0.4 |
| "Coarse" Feed for Example 3 after classification | 92 | 158 | 245 | 0.2 |

It can be seen from Table 8 that there were two instances in which the target for removing the fine material less than 70 microns was not quite achieved, although the values of 66 and 67 microns are close enough that they are believed to not impact on the outcome of the experiments.

Milling of the Classified Feed

Each of the coarse fractions were then milled to reduce the D50 to between 60-70 microns by Malvern. The values from Example 1 indicated that slightly harder milling was required, so this was adjusted for Examples 2 and 3.

The results are shown in Table 9 (Malvern) and Table 10 (Sympatec).

TABLE 9

Milled "Coarse" fraction. Particle Size Data by Malvern.

| | Malvern Data | | | |
|---|---|---|---|---|
| | D10 | D50 | D90 | % < 15 microns |
| "Fine" Feed for Example 1 after milling coarse fraction) | 15 | 75 | 152 | 10.0 |
| "Coarse" Feed for Example 1 after milling coarse fraction) | 13 | 72 | 169 | 11.4 |
| "Fine" Feed for Example 2 after milling coarse fraction) | 15 | 70 | 141 | 9.9 |
| "Coarse" Feed for Example 2 after milling coarse fraction) | 13 | 66 | 145 | 11.5 |
| "Fine" Feed for Example 3 after milling coarse fraction) | 14 | 64 | 133 | 10.9 |
| "Coarse" Feed for Example 3 after milling coarse fraction) | 12 | 61 | 139 | 13.1 |

TABLE 10

Milled "Coarse" fraction. Particle Size Data by Sympatec

| | Sympatec Data | | | |
|---|---|---|---|---|
| | D10 | D50 | D90 | % < 4.5 microns |
| "Fine" Feed for Example 1 after milling coarse fraction) | 7.0 | 63 | 140 | 6.5 |
| "Coarse" Feed for Example 1 after milling coarse fraction) | 6.3 | 55 | 151 | 7.3 |
| "Fine" Feed for Example 2 after milling coarse fraction) | 7.5 | 59 | 127 | 6.3 |
| "Coarse" Feed for Example 2 after milling coarse fraction) | 6.1 | 54 | 132 | 7.7 |

TABLE 10-continued

Milled "Coarse" fraction. Particle Size Data by Sympatec

| | Sympatec Data | | | |
|---|---|---|---|---|
| | D10 | D50 | D90 | % < 4.5 microns |
| "Fine" Feed for Example 3 after milling coarse fraction) | 7.0 | 55 | 123 | 6.7 |
| "Coarse" Feed for Example 3 after milling coarse fraction) | 5.4 | 48 | 125 | 8.3 |

Classification of the Milled Lactose

The milled lactose was then separated into a coarse and fine fraction using the same classifier as was used to separate the fine lactose from the input feed lactose. The resultant particle size data are shown in Tables 11, 12, 13 and 14.

TABLE 11

Fine Fractions after Milling and Classification of the Coarse Crystalline Feed Fraction by Malvern

| | Malvern Data | | | |
|---|---|---|---|---|
| | D10 | D50 | D90 | % < 15 microns |
| "Fine" Feed for Example 1 Milled/Classified after classification | 7.0 | 28 | 64 | 27.1 |
| "Coarse" Feed for Example 1 Milled/Classified after classification | 7.0 | 26 | 55 | 28.8 |
| "Fine" Feed for Example 2 Milled/Classified after classification | 7.3 | 26 | 59 | 28.5 |
| "Coarse" Feed for Example 2 Milled/Classified after classification | 7.0 | 26 | 59 | 30.0 |
| "Fine" Feed for Example 3 Milled/Classified after classification | 7.1 | 27 | 58 | 27.4 |
| "Coarse" Feed for Example 3 Milled/Classified after classification | 7.0 | 26 | 56 | 29.0 |

TABLE 12

Coarse Fractions after Milling and Classification of the Coarse Crystalline Feed Fraction by Malvern

| | Malvern Data | | | |
|---|---|---|---|---|
| | D10 | D50 | D90 | % < 15 microns |
| "Fine" Feed for Example 1 Milled/Classified after classification | 52 | 97 | 164 | 2.2 |
| "Coarse" Feed for Example 1 Milled/Classified after classification | 48 | 101 | 189 | 2.5 |
| "Fine" Feed for Example 2 Milled/Classified after classification | 49 | 88 | 153 | 1.5 |
| "Coarse" Feed for Example 2 Milled/Classified after classification | 49 | 93 | 166 | 2.0 |
| "Fine" Feed for Example 3 Milled/Classified after classification | 48 | 87 | 151 | 1.7 |
| "Coarse" Feed for Example 3 Milled/Classified after classification | 50 | 91 | 157 | 1.6 |

TABLE 13

Fine Fractions after Milling and Classification of the Coarse Crystalline Feed Fraction by Sympatec

| | Sympatec Data | | | |
|---|---|---|---|---|
| | D10 | D50 | D90 | % < 15 microns |
| "Fine" Feed for Example 1 Milled/Classified after classification | 4.0 | 22 | 57 | 12.9 |
| "Coarse" Feed for Example 1 Milled/Classified after classification | 4.0 | 22 | 56 | 13.1 |
| "Fine" Feed for Example 2 Milled/Classified after classification | 3.4 | 21 | 52 | 13.9 |
| "Coarse" Feed for Example 2 Milled/Classified after classification | 3.0 | 20 | 51 | 15.1 |
| "Fine" Feed for Example 3 Milled/Classified after classification | 3.5 | 22 | 54 | 13.3 |
| "Coarse" Feed for Example 3 Milled/Classified after classification | 3.0 | 21 | 54 | 14.5 |

TABLE 14

Coarse Fractions after Milling and Classification of the Coarse Crystalline Feed Fraction by Sympatec

| | Sympatec Data | | | |
|---|---|---|---|---|
| | D10 | D50 | D90 | % < 15 microns |
| "Fine" Feed for Example 1 Milled/Classified after classification | 39 | 90 | 149 | 2.9 |
| "Coarse" Feed for Example 1 Milled/Classified after classification | 35 | 93 | 174 | 2.9 |
| "Fine" Feed for Example 2 Milled/Classified after classification | 40 | 83 | 141 | 2.0 |
| "Coarse" Feed for Example 2 Milled/Classified after classification | 39 | 88 | 150 | 2.5 |
| "Fine" Feed for Example 3 Milled/Classified after classification | 40 | 82 | 139 | 2.1 |
| "Coarse" Feed for Example 3 Milled/Classified after classification | 43 | 87 | 146 | 2.1 |

Recombination by Blending

The Examples 1-3 then call for appropriate portions of the fine and coarse fractions to be blended together so that the resultant blend contains the required amount of lactose that is less than 4.5 microns. This is in order to achieve the desired value for the FPMass performance for an inhalable formulation of salmeterol xinafoate and fluticasone propionate. These target values are listed in the Examples 1-3, and the results are shown in Tables 15-17.

TABLE 15

Particle Size Data for final packed product from Example 1-Sympatec

| | Sympatec Data | | | |
|---|---|---|---|---|
| | D10 | D50 | D90 | % < 4.5 microns |
| "Fine" Feed for Example 1 | | | | |
| Target - 3.3% +/− 0.3% | 28 | 89 | 150 | 3.4 |
| Target - 6.7% +/− 0.3%, | 7 | 62 | 139 | 6.7 |
| Target - 5.0% +/− 0.3% | 11 | 78 | 147 | 5.0 |
| "Coarse" Feed for Example 1 | | | | |
| Target - 6.7% +/− 0.3%, | 7.3 | 66 | 161 | 6.5 |
| Target - 5.0% +/− 0.3% | 10 | 79 | 167 | 5.2 |
| Target - 3.3% +/− 0.3% | 26 | 91 | 172 | 3.4 |

It can be seen from these Example 1 data that the Sympatec targets at %<4.5 microns were met in every case.

TABLE 16

Particle Size Data for final packed product from Example 2-Sympatec

| | Sympatec Data | | | |
|---|---|---|---|---|
| | D10 | D50 | D90 | % < 4.5 microns |
| "Fine" Feed for Example 2-216014 | | | | |
| Target - 6.7% +/- 0.3% | 7.2 | 57 | 125 | 6.6 |
| Target - 5.0% +/- 0.3%, | 10 | 67 | 131 | 5.1 |
| Target - 3.3% +/- 0.3% | 23 | 76 | 135 | 3.3 |
| "Coarse" Feed for Example 2-216017 | | | | |
| Target - 6.7% +/- 0.3%, | 7.4 | 59 | 134 | 6.4 |
| Target - 5.0% +/- 0.3% | 11 | 75 | 145 | 5.0 |
| Target - 3.3% +/- 0.3% | 24 | 83 | 148 | 3.3 |

It can be seen from the Example 2 particle size data that the Sympatec targets were met in every case.

TABLE 17

Particle Size Data for final packed product from Example 3-Sympatec

| | Sympatec Data | | | |
|---|---|---|---|---|
| | D10 | D50 | D90 | % < 4.5 microns |
| "Fine" Feed for Example 3 | | | | |
| Target - 6.3% +/- 0.3% | 9.0 | 63 | 129 | 5.5 |
| Target - 6.0% +/- 0.3% | 10.0 | 68 | 132 | 5.1 |
| Target - 5.5% +/- 0.3% | 11 | 70 | 133 | 4.7 |
| "Coarse" Feed for Example 3 | | | | |
| Target - 6.3 +/- 0.3% | 7.8 | 66 | 135 | 6.2 |
| Target - 6.0 +/- 0.3% | 7.9 | 69 | 137 | 6.1 |
| Target - 5.5 +/- 0.3% | 10.0 | 72 | 139 | 5.3 |

It can be seen from these Example 3 data that the Sympatec targets were met for the three batches stemming from the coarse feed but not for those made from the fine feed.

Averages and relative standard deviation values for the D10, D50, D90 and the %<15 microns for both the fine and coarse fractions for conventional production were evaluated, compared to the process of the invention. These are shown in Table 17. All values are Malvern data and the normal production is all batches of the same lactose product manufactured over an 18 month period.

TABLE 17

Assessment of Particle size consistency for Example 1, Example 2 and Example 3 data

| | d10 | d50 | d90 | % < 15 microns |
|---|---|---|---|---|
| Fine fraction after Classification - Malvern | | | | |
| Current Process approximately 18 months normal production (mean of 73 batches) | 6.9 | 19.6 | 44.8 | 38.0 |
| Example 1, 2 and 3 mean of 6 batches | 7.1 | 26.5 | 58.5 | 28.5 |
| RSD Current Process approximately 18 months normal production- (73 batches) | 8.9% | 12.7% | 15.4% | 15.6% |
| RSD Example 1, 2 and 3- (6 batches) | 1.7% | 3.2% | 5.4% | 3.8% |
| Coarse Fraction after Classification - Malvern | | | | |
| Current Process approximately 18 months normal production (mean of 73 batches) | 42.0 | 90.6 | 172.5 | 1.7 |
| Example 1, 2 and 3 mean of 6 batches | 49.3 | 92.8 | 163.3 | 1.9 |
| RSD Current Process approximately 18 months normal production- (73 batches) | 15.0% | 7.8% | 7.5% | 75.3% |
| RSD Example 1, 2 and 3- (6 batches) | 3.1% | 5.8% | 8.5% | 20.2% |

The results in Table 17 show that the particle size of the coarse and fine fractions are more consistent than that obtained during normal production, despite the fact that an adjustment was made to the milling settings between Example 1 and Examples 2 and 3. If Example 1 data is eliminated from the assessment then the variation in particle size is even less as shown in Table 18.

TABLE 18

Assessment of Example 2 and Example 3 data only-Malvern

| | d10 | D50 | D90 | % < 15 microns |
|---|---|---|---|---|
| Fine fraction after Classification - Malvern | | | | |
| Current Process approximately 18 months normal production (mean of 73 batches) | 6.9 | 19.6 | 44.8 | 38.0 |
| Example 2 and 3 mean of 4 batches | 7.1 | 26.3 | 58.0 | 28.7 |
| RSD Current Process approximately 18 months normal production- (73 batches) | 8.9% | 12.7% | 15.4% | 15.6% |

TABLE 18-continued

| Assessment of Example 2 and Example 3 data only-Malvern | | | | |
|---|---|---|---|---|
| | d10 | D50 | D90 | % < 15 microns |
| RSD EXAMPLE 2 and 3- (4 batches) | 2.0% | 1.9% | 2.4% | 3.8% |
| Coarse Fraction after Classification - Malvern | | | | |
| Current Process approximately 18 months normal production (mean of 73 batches) | 42.0 | 90.6 | 172.5 | 1.7 |
| Example 2 and 3 approximately 18 months normal production mean of 4 batches | 49.0 | 89.8 | 156.8 | 1.7 |
| RSD Current Process approximately 18 months normal production- (73 batches) | 15.0% | 7.8% | 7.5% | 75.3% |
| RSD Example 2 and 3- (4 batches) | 1.7% | 3.1% | 4.2% | 12.7% |

Particle Size Profiles for Example 1, Example 2 and Example 3

Figure 2:
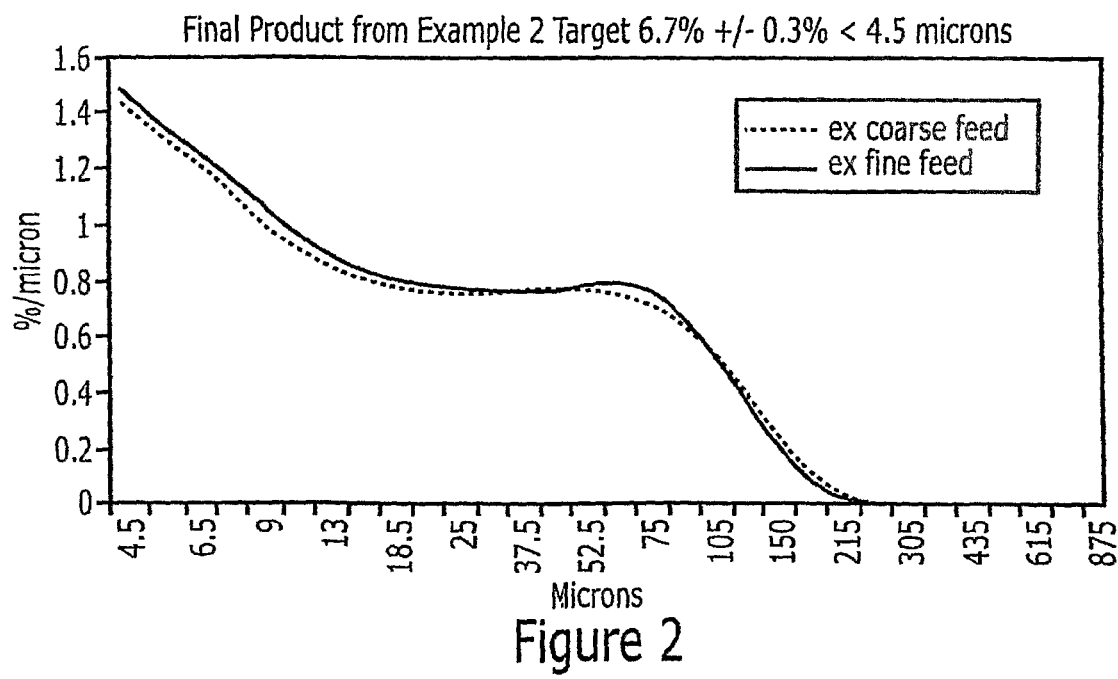
FIG. 2 illustrates a particle size profile for lactose formed in accordance with Example 2.
Figure 3:
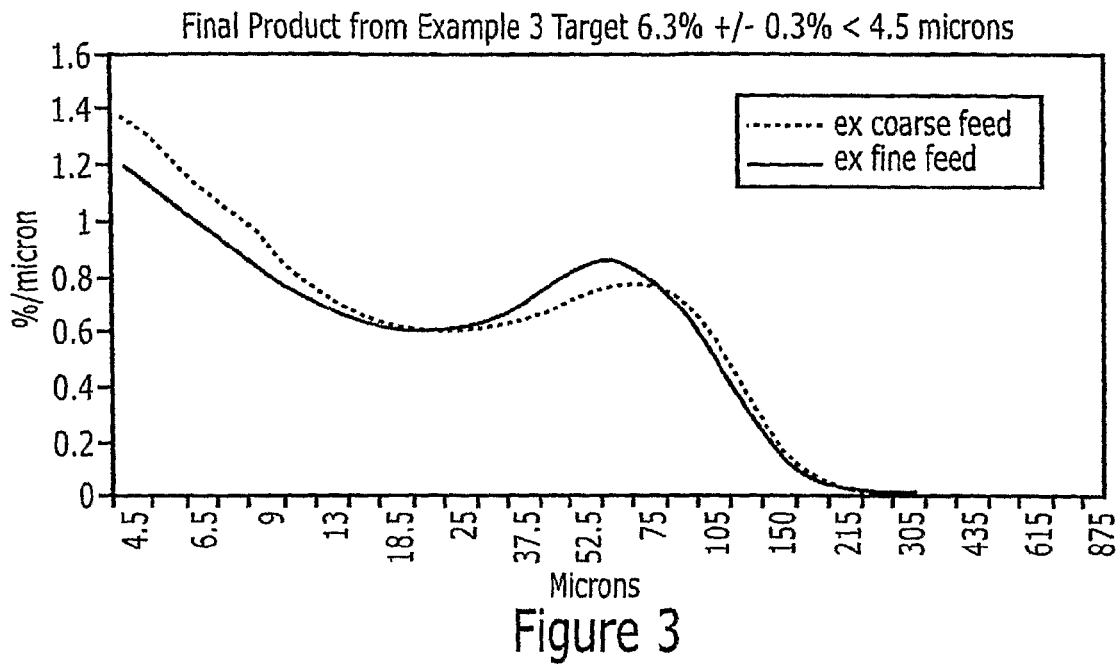
FIG. 3 illustrates a particle size profile for lactose formed in accordance with Example 3.

The full profiles for each of the three pairs of lactose made in Examples 1 and 3 are shown in FIGS. 1-3.

Figure 4:
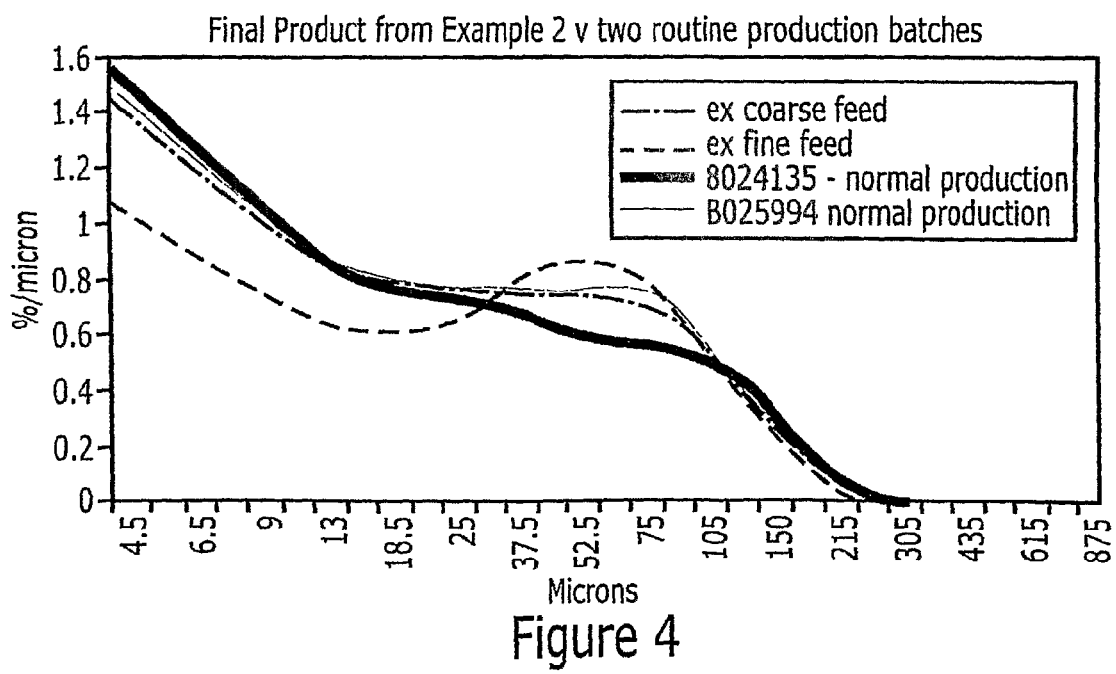
FIG. 4 illustrates a comparison of a particle size profile for lactose formed in accordance with Example 2 with two conventional production batches.

It can be seen that these three pairs of curves are reasonably similar, despite originating from a "coarse" and "fine" feed in each occasion. For a comparison FIG. 4 shows the data form Example 2 overlaid with two normal production batches of similar lactose. These show the extremes in differing profiles that can be obtained during normal production.

EXAMPLE 4

Lactose Production

The following example demonstrates the production of lactose suitable for use in inhalation formulations, which has been produced by a method that does not require the combination of any of the fine fraction to the coarse fraction.

The following experimental method may be employed:
1. Classify 2 tons of crystalline lactose A so that the majority of fine crystals <70 microns are removed into the fine fraction. The remaining coarse fraction must comply with the acceptance criteria shown in Table 19 below.

TABLE 19

| | Measurement are by Sympatec | | |
|---|---|---|---|
| | %<4.5 microns | D10 | D50 |
| Coarse Fraction | <0.2% | >70 microns | >130 microns |

3. Mill only the coarse fraction of lactose targeting 60 microns +/−3 microns for the D50 of the milled product.
4. Using pilot scale blender, separate 300 kgs of the milled batch into a fine and coarse fraction using the maximum classifier wheel speed and suitable air flow parameters to achieve the lowest micron cut point that can be achieved. This will leave a coarse fraction that contains as much fine lactose as possible. (Product A)
5. Repeat 4 on another 300 kg aliquot of the milled lactose, but reduce the speed of the classifier wheel and keep the air flow at the same settings. This will produce a somewhat coarser coarse fraction. (Product B)
6. Repeat 4 again on another 300 kg aliquot of the milled lactose, but reduce the speed of the classifier wheel further and keep the air flow at the same settings. This again will produce an even coarser coarse fraction. (Product C)
7. Do not add any of the fine fractions to the coarse fractions, but blend each of the coarse fractions to ensure homogeneity. Dispense the blended lactose into 20 kg tie sealed polyethylene bags, which are then heat sealed into a foil laminate bag.

Pack at least 7×20 kgs boxes of each batch, and record the particle size distribution by Sympatec on the final product.

TABLE 20

| Results of the Classified Feed Lactose - Coarse Fraction: | | | |
|---|---|---|---|
| Sample Number | %<4.5 microns | D10 | D50 |
| 1 | 0% | 92.03 | 155.96 |
| 2 | 0% | 93.87 | 159.5 |
| 3 | 0% | 90.75 | 156.24 |
| 4 | 0% | 93.28 | 158.26 |
| 5 | 0% | 92.53 | 157.05 |

It can be seen from the data in Table 20 that the readings comply with the specifications detailed in Table 19.

Results for the full particle size distribution of the final products A, B & C by Sympatec are in Table 21.

TABLE 21

| Sympatec High Size Microns | Product A | Product B | Product C |
|---|---|---|---|
| 4.50 | 4.26 | 4.01 | 3.91 |
| 5.50 | 5.30 | 4.94 | 4.80 |
| 6.50 | 6.33 | 5.86 | 5.65 |
| 7.50 | 7.36 | 6.76 | 6.48 |
| 9.00 | 8.89 | 8.10 | 7.71 |
| 11.00 | 10.92 | 9.88 | 9.33 |
| 13.00 | 12.94 | 11.68 | 10.98 |
| 15.50 | 15.47 | 13.99 | 13.11 |
| 18.50 | 18.49 | 16.83 | 15.79 |
| 21.50 | 21.47 | 19.75 | 18.59 |
| 25.00 | 24.91 | 23.19 | 21.94 |
| 30.00 | 29.69 | 28.07 | 26.79 |
| 37.50 | 36.54 | 35.18 | 33.96 |
| 45.00 | 43.05 | 41.93 | 40.85 |
| 52.50 | 49.24 | 48.34 | 47.43 |
| 62.50 | 57.02 | 56.34 | 55.64 |
| 75.00 | 65.83 | 65.35 | 64.89 |
| 90.00 | 74.83 | 74.48 | 74.26 |
| 105.00 | 81.95 | 81.64 | 81.60 |
| 125.00 | 88.81 | 88.49 | 88.60 |
| 150.00 | 94.13 | 93.77 | 93.97 |
| 180.00 | 97.47 | 97.08 | 97.30 |
| 215.00 | 99.14 | 98.78 | 98.96 |
| 255.00 | 99.77 | 99.54 | 99.65 |
| 305.00 | 100.00 | 99.87 | 99.93 |
| 365.00 | 100.00 | 100.00 | 99.98 |
| 435.00 | 100.00 | 100.00 | 100.00 |
| 515.00 | 100.00 | 100.00 | 100.00 |
| 615.00 | 100.00 | 100.00 | 100.00 |
| 735.00 | 100.00 | 100.00 | 100.00 |
| 875.00 | 100.00 | 100.00 | 100.00 |

Figure 8:
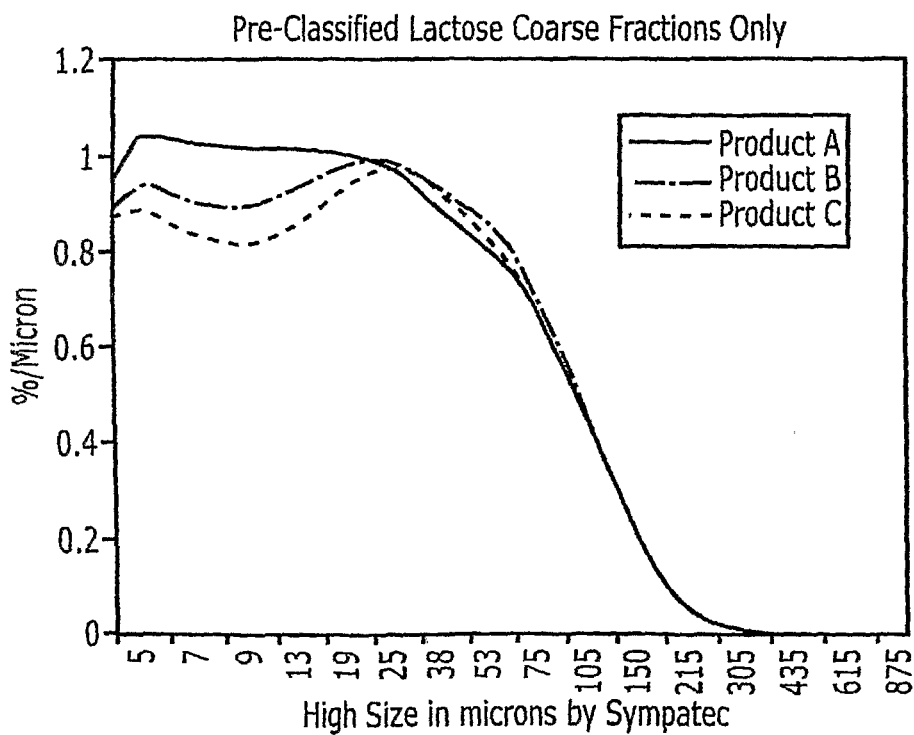
FIG. 8 illustrates the particle size distribution for pre-classified lactose, coarse fraction.

These data can also be presented graphically as shown in FIG. 8. It can be seen from FIG. 8 that the amount of lactose present in the region <25 microns high size is of the same order as that shown in FIG. 4 which is that of routine commercial batches used for inhalation grade lactose. Thus, these coarse fractions are believed to be capable of displaying suitable Fine Particle Mass (FPM) performance to make them useful as inhalation grade lactose.

Conclusions:

All of the trials, Example 1, Example 2 and Example 3 have been assessed for CI performance at release and upon accelerated ageing at 25 degrees Celsius, 75% relative humidity. The series of Tables 22A, 22B and 22C show the initial mean data that were obtained during the stability study for Fine Particle Mass (FPMass), Throat, Pre-separator and stage 0, (TP0) and Stages 3+4.

TABLE 22A i

Initial Mean Fine Particle Mass Data for 75 µg salmeterol xinafoate (equivalent to 50 µg salmeterol base) and 100 µg fluticasone propionate formulation using a conventional fine lactose

| DP Trial | Fine Particle Mass (FP) | Fine Particle Mass (SX) |
|---|---|---|
| Example 1 - (fine lactose) ex Coarse feed | 28.6 | 12.4 |
| Example 1 - (fine lactose) ex Fine feed | 31.8 | 13.9 |
| Example 2 - (fine lactose) ex Coarse feed | 26.3 | 12.9 |
| Example 2 - (fine lactose) ex Fine feed | 25.6 | 12.4 |
| Example 3 - (fine lactose) ex Coarse feed | 22.7 | 10.3 |
| Example 3 - (fine lactose) ex Fine feed | 21.3 | 10.4 |

TABLE 22A ii

Initial Mean TP0 Data for 50 µg salmeterol base/100 µg fluticasone propionate formulation sing a conventional fine lactose

| DP Trial | TP0 (FP) | TP0 (SX) |
|---|---|---|
| Example 1 - (fine lactose) ex Coarse feed | 64.4 | 32.9 |
| Example 1 - (fine lactose) ex Fine feed | 62.0 | 31.8 |
| Example 2 - (fine lactose) ex Coarse feed | 65.7 | 33.0 |
| Example 2 - (fine lactose) ex Fine feed | 65.9 | 32.8 |
| Example 3 - (fine lactose) ex Coarse feed | 68.8 | 34.4 |
| Example 3 - (fine lactose) ex Fine feed | 70.2 | 35.4 |

TABLE 22A iii

Initial Mean Stages 3 + 4 Data for 50 µg salmeterol base/100 µg fluticasone propionate formulation using conventional fine lactose

| DP Trial | 3 + 4 (FP) | 3 + 4 (SX) |
|---|---|---|
| Example 1 - fine lactose) ex Coarse feed | 15.8 | 7.0 |
| Example 1 - (fine lactose) ex Fine feed | 18.0 | 8.1 |
| Example 2 - (fine lactose) ex Coarse feed | 14.4 | 7.2 |
| Example 2 - (fine lactose) ex Fine feed | 13.9 | 6.9 |
| Example 3 - (fine lactose) ex Coarse feed | 11.9 | 5.4 |
| Example 3 - (fine lactose) ex Fine feed | 11.9 | 5.7 |

NB.
Specifications for Advair 50/100 are:
FP FPMass, 21-30;
SX FPMass, 9-13
FP Stages 3 + 4, 11-19;
SX Stages 3 + 4, 4-8
FP TP0, 55-80;
SX TP0, 28-42

TABLE 22B i

Initial Mean Fine Particle Mass Data for 50 µg salmeterol base/250 µg fluticasone propionate formulation using a conventional medium grade lactose

| DP Trial | Fine Particle Mass (FP) | Fine Particle Mass (SX) |
|---|---|---|
| Example 1 - (Medium Lactose) ex Coarse feed | 57.8 | 10.5 |
| Example 1 - (Medium Lactose) ex Fine feed | 55.7 | 10.4 |
| Example 3 - (Medium Lactose) ex Coarse feed | 68.8 | 13.3 |
| Example 3 - (Medium Lactose) ex Fine feed | 50.3 | 9.7 |

TABLE 22B ii

Initial Mean TP0 Data for 50 µg salmeterol base/250 µg fluticasone propionate formulation using a medium grade lactose

| DP Trial | TP0 (FP) | TP0 (SX) |
|---|---|---|
| Example 1 - (Medium Lactose) ex Coarse feed | 170.5 | 34.0 |
| Example 1 - (Medium Lactose) ex Fine feed | 174.8 | 35.2 |
| Example 3 - (Medium Lactose) ex Coarse feed | 154.7 | 32.1 |
| Example 3 - (Medium Lactose) ex Fine feed | 168.8 | 33.2 |

TABLE 22B iii

Initial Mean Stages 3 + 4 Data for 50 µg salmeterol base/250 µg fluticasone propionate formulation using a conventional medium grade lactose

| DP Trial | Stages 3 + 4 (FP) | Stages 3 + 4 (SX) |
|---|---|---|
| Example 1 - (Medium Lactose) ex Coarse feed | 32.7 | 6.0 |
| Example 1 - (Medium Lactose) ex Fine feed | 30.2 | 5.7 |
| Example 3 - (Medium Lactose) ex Coarse feed | 40.0 | 7.8 |
| Example 3 - (Medium Lactose) ex Fine feed | 27.2 | 5.2 |

NB.
Specifications for Advair 50/250 are:
FP FPMass, 51-75;
SX FP Mass, 9-13
FP Stages 3 + 4, 29-48;
SX Stages 3 + 4, 5-8
FP TP0, 140-200;
SX TP0, 28-42

TABLE 22C i

Initial Mean Fine Particle Mass Data for 50 μg salmeterol base/500 μg fluticasone propionate formulation using a conventional coarse grade lactose

| DP Trial | Fine Particle Mass (FP) | Fine Particle Mass (SX) |
| --- | --- | --- |
| Example 1 - (Coarse Lactose) ex Coarse feed | 74.9 | 7.1 |
| Example 1 - (Coarse Lactose) ex Fine feed | 85.0 | 7.9 |
| Example 3 - (Coarse Lactose) ex Coarse feed | 125.7 | 12.7 |
| Example 3 - (Coarse Lactose) ex Fine feed | 123.5 | 11.9 |

TABLE 22C ii

Initial Mean TPO Data for 50 μg salmeterol base/500 μg fluticasone propionate formulation using a conventional coarse grade lactose

| DP Trial | TPO (FP) | TPO (SX) |
| --- | --- | --- |
| Example 1 - (Coarse Lactose) ex Coarse feed | 399.2 | 39.3 |
| Example 1 - (Coarse Lactose) ex Fine feed | 392.1 | 38.8 |
| Example 3 - (Coarse Lactose) ex Coarse feed | 293.1 | 33.4 |
| Example 3 - (Coarse Lactose) ex Fine feed | 323.0 | 32.3 |

TABLE 22C iii

Initial Mean Stages 3 + 4 Data for 50 μg salmeterol base/500 μg fluticasone propionate formulation using a conventional coarse grade lactose

| DP Trial | Stages 3 + 4 (FP) | Stages 3 + 4 (SX) |
| --- | --- | --- |
| Example 1 - (Coarse Lactose) ex Coarse feed | 42.4 | 4.0 |
| Example 1 - (Coarse Lactose) ex Fine feed | 49.0 | 4.5 |
| Example 3 - (Coarse Lactose) ex Coarse feed | 74.2 | 7.5 |
| Example 3 - (Coarse Lactose) ex Fine feed | 78.5 | 7.6 |

NB.
Specifications for Advair 50/500 are:
FP FPMass, 106-150;
SX FPMass, 10-14.
FP Stages 3 + 4, 60-95;
SX Stages 3 + 4, 5-9.
FP TP0, 290-400;
SX TP0, 28-42.

Taking all of the factors into account, the data suggests that the pre-classification of the feed crystal to remove small lactose crystals below approximately 70 microns does not appear to significantly alter the performance ex device when compared to the normal method of lactose production. Additionally, and advantageously, the invention offers a process for forming lactose which provides improved control of particle size distribution relative to conventional processes.

EXAMPLE 5

Stability Tests

Stability data for various formulations each containing 100 μg fluticasone propionate and 50 μg salmeterol base along with lactose formed in accordance with the invention were evaluated under naked conditions at 25° C. and 75 percent Relative Humidity. As shown in Table 23, such data were evaluated at different time points. As shown, formulations made from the process according to the invention exhibit good stability characteristics.

TABLE 23

| Advair Strength | Experiment Number | Conditions: Temp/% RH | Time point (months) | SX Fine Particle Mass | FP Fine Particle Mass |
| --- | --- | --- | --- | --- | --- |
| 100/50 | 1 |  | initial | 12.38 | 28.55 |
| 100/50 | 1 | 25/75 | 0.5 | 12.53 | 27.74 |
| 100/50 | 1 | 25/75 | 1.0 | 12.87 | 28.72 |
| 100/50 | 1 | 25/75 | 1.5 | 12.22 | 27.34 |
| 100/50 | 1 | 25/75 | 2.0 | 12.05 | 27.61 |
| 100/50 | 1 | 25/75 | 3.0 | 11.45 | 25.77 |
| 100/50 | 1 |  | initial | 13.87 | 31.81 |
| 100/50 | 1 | 25/75 | 0.5 | 13.14 | 30.60 |
| 100/50 | 1 | 25/75 | 1.0 | 12.97 | 29.29 |
| 100/50 | 1 | 25/75 | 1.5 | 13.11 | 29.61 |
| 100/50 | 1 | 25/75 | 2.0 | 13.23 | 30.77 |
| 100/50 | 1 | 25/75 | 3.0 | 12.29 | 27.83 |
| 100/50 | 2 |  | initial | 12.42 | 25.60 |
| 100/50 | 2 | 25/75 | 2.0 | 11.59 | 24.64 |
| 100/50 | 2 | 25/75 | 3.0 | 11.34 | 24.24 |
| 100/50 | 2 |  | initial | 12.92 | 26.31 |
| 100/50 | 2 | 25/75 | 2.0 | 11.80 | 24.88 |
| 100/50 | 2 | 25/75 | 3.0 | 10.84 | 23.04 |
| 100/50 | 3 |  | initial | 10.27 | 22.69 |
| 100/50 | 3 | 25/75 | 0.5 | 11.65 | 24.27 |
| 100/50 | 3 | 25/75 | 1.0 | 10.84 | 24.92 |
| 100/50 | 3 | 25/75 | 1.5 | 10.59 | 22.21 |
| 100/50 | 3 | 25/75 | 3.0 | 10.23 | 21.86 |
| 100/50 | 3 |  | initial | 10.43 | 21.32 |
| 100/50 | 3 | 25/75 | 0.5 | 9.06 | 19.21 |
| 100/50 | 3 | 25/75 | 1.0 | 10.05 | 21.11 |
| 100/50 | 3 | 25/75 | 1.5 | 8.61 | 18.38 |
| 100/50 | 3 | 25/75 | 3.0 | 8.21 | 17.45 |

EXAMPLES 6-8

Stability Studies

Examples 6-8 set forth various pharmaceutical formulations for which the stability was evaluated. Batches 01, 02 and 03 were processed in accordance with the present invention by employing a pre-classification stage prior to proceeding by conventional manufacturing used for making Advair® made commercially available by GlaxoSmithkline of Brenfford, United Kingdom. Batch 04 was made using an Advair® manufacturing process. In Tables 24-28, the symbol "T" indicates that the particle size distribution of salmeterol xinafoate and fluticasone propionate were evaluated by Cascade Impaction according to Method STM-195.

Tables 29-31 illustrate the average change of drug recovered in stages 1 to 5 as a percentage, normalising the results to take into account the total drug recovery for each device. The change is determined between the initial and final time points as defined in the protocol and is calculated according to the following equation:

$$\frac{\text{Stage 1 to 5 recovery at initial}}{\text{Total recovery at initial point}} \times 100 - \frac{\text{Stage 1 to 5 recovery at final time point}}{\text{Total recovery at final time}} \times 100$$

Tables 32-34 provide summaries of the stability studies that are set forth in Tables 35 to 130. These tables illustrate Cascade Impaction results.

Referring to the tables that follow:

"500/50 µg" refers to a formulation containing 50 µg salmeterol base and 500 µg fluticasone propionate in lactose.

"250/50 µg" refers to a formulation containing 50 µg salmeterol base and 250 µg fluticasone propionate in lactose.

"100/50 µg" refers to a formulation containing 50 µg salmeterol base and 100 µg fluticasone propionate in lactose.

"MDPI" refers to a multidose dry powder inhaler.

A* refers to in-use testing. Devices to be removed from 25° C./60% RH storage and overwrappers to be removed. Samples to be returned to storage at 25° C./75% RH. See Tables 25 and 27.

In Tables 32-34, Batches A, E and I correspond to batch 01. Batches B, F and J correspond to batch 02. Batches C, G and K correspond to batch 03. Batches D, H and L correspond to batch 04.

Tables 24-25: Testing Protocols for 100/50 µg

TABLE 24

| Storage condition | Storage time (months) | | | | | | | | |
|---|---|---|---|---|---|---|---|---|---|
| ° C./% RH | Initial | 0.5 | 1 | 1.5 | 3 | 6 | 9 | 12 | 14 | 15 |
| 25/60 Wrapped | T | | | T | | T | T | T | T | A* | T |
| 25/75 Naked | | T | T | T | T | | | | | |

TABLE 25

| Storage condition | Storage time (months) | | | |
|---|---|---|---|---|
| ° C./% RH | 0 | 0.5 | 1 | 1.5 |
| [Total time on test] | [14] | [14.5] | [15] | [15.5] |
| 25/75 Naked | T | T | T | T |

TABLE 26

Testing Protocol for 250/50 µg

| Storage condition | Storage time (months) | | | | | | | | |
|---|---|---|---|---|---|---|---|---|---|
| ° C./% RH | Initial | 0.5 | 1 | 1.5 | 3 | 6 | 9 | 12 | 17 | 18 |
| 25/60 Wrapped | T | | | T | | T | T | T | T | A* | T |
| 25/75 Naked | | T | T | T | T | | | | | |

Tables 27-28 Testing Protocol for 500/50 µg

TABLE 27

| Storage condition | Storage time (months) | | | |
|---|---|---|---|---|
| ° C./% RH | 0 | 0.5 | 1 | 1.5 |
| [Total time on test] | [17] | [17.5] | [18] | [18.5] |
| 25/75 Naked | T | T | T | T |

| Storage condition | Storage time (months) | | | | | | | | |
|---|---|---|---|---|---|---|---|---|---|
| ° C./% RH | Initial | 0.5 | 1 | 1.5 | 3 | 6 | 9 | 12 | 17 | 18 |
| 25/60 Wrapped | T | | | T | | T | T | T | T | A* | T |
| 25/75 Naked | | T | T | T | T | | | | | |

TABLE 28

| Storage condition | Storage time (months) | | | |
|---|---|---|---|---|
| ° C./% RH | 0 | 0.5 | 1 | 1.5 |
| [Total time on test] | [17] | [17.5] | [18] | [18.5] |
| 25/75 Naked | T | T | T | T |

TABLE 29

Average Change of Drug Recovered in Stages 1-5 (100/50 µg)

| | Batch | | | |
|---|---|---|---|---|
| Storage Condition/Drug | 01 | 02 | 03 | 04 |
| 25° C./60% RH Wrapped SX | −5 | −5 | −5 | −5 |
| 25° C./60% RH Wrapped FP | −5 | −5 | −6 | −6 |
| 25° C./75% RH Naked SX | −7 | −3 | −4 | −4 |
| 25° C./75% RH Naked FP | −7 | −4 | −6 | −5 |
| 25° C./75% RH Naked Aged In Use SX | 0 | +1 | −2 | −1 |
| 25° C./75% RH Naked Aged In Use FP | 0 | 0 | −2 | −1 |

TABLE 30

Average Change of Drug Recovered in Stages 1-5 (250/50 µg)

| | Batch | | | |
|---|---|---|---|---|
| Storage Condition/Drug | 01 | 02 | 03 | 04 |
| 25° C./60% RH Wrapped SX | −5 | −4 | −6 | −3 |
| 25° C./60% RH Wrapped FP | −6 | −5 | −7 | −4 |
| 25° C./75% RH Naked SX | −5 | −5 | −4 | −4 |
| 25° C./75% RH Naked FP | −5 | −5 | −4 | −3 |
| 25° C./75% RH Naked Aged In Use SX | +1 | 0 | −2 | 0 |
| 25° C./75% RH Naked Aged In Use FP | 0 | 0 | −2 | −1 |

TABLE 31

Average Change of Drug Recovered in Stages 1-5 (500/50 µg)

| | Batch | | | |
|---|---|---|---|---|
| Storage Condition/Drug | 01 | 02 | 03 | 04 |
| 25° C./60% RH Wrapped SX | −5 | −3 | −4 | −3 |
| 25° C./60% RH Wrapped FP | −5 | −3 | −4 | −3 |
| 25° C./75% RH Naked SX | −3 | −3 | 0 | −4 |
| 25° C./75% RH Naked FP | −3 | −3 | −1 | −4 |
| 25° C./75% RH Naked Aged In Use SX | +1 | +1 | 0 | +2 |
| 25° C./75% RH Naked Aged In Use FP | +1 | 0 | 0 | +1 |

TABLE 32

Summary of Stability Studies for 100/50 µg MDPI (Example 6)

| | Stability data table number (s) | | | |
|---|---|---|---|---|
| | 35 to 43 | 44 to 50 | 51 to 58 | 59 to 66 |
| Batch designation (methodology) | A | B | C | D |
| Lactose batch designation | DD | DD | EE | FF |
| % of lactose fines | 6.7 | 6.7 | 7.0 | 5.6 |
| Data presented 25/60W | 15M | 15M | 15M | 15M |
| 25/75N | 3M | 3M | 3M | 3M |
| 25/75N Aged In Use | 1.5M | 1.5M | 1.5M | 1.5M |
| Specification failures 25/60W | 1* | 1* | 1* | 0 |
| Specification failures 25/75N | 3* | 5* | 3* | 0 |
| Specification failures 25/75N Aged In Use | 1* | 0 | 1* | 0 |

TABLE 33

Summary of Stability Studies for 250/50 µg MDPI (Example 7)

| | Stability data table number (s) | | | |
|---|---|---|---|---|
| | 67 to 74 | 75 to 82 | 83 to 90 | 91 to 98 |
| Batch designation (methodology) | E | F | G | H |
| Lactose batch designation | AA | AA | BB | CC |
| % of lactose fines | 5.2 | 5.2 | 6.4 | 4.7 |
| Data presented 25/60W | 18M | 18M | 18M | 18M |
| 25/75N | 3M | 3M | 3M | 3M |
| 25/75N Aged In Use | 1.5M | 1.5M | 1.5M | 1.5M |
| Specification failures 25/60W | 0 | 1* | 3* | 0 |
| Specification failures 25/75N | 2* | 0 | 4* | 0 |
| Specification failures 25/75N Aged In Use | 0 | 0 | 0 | 0 |

TABLE 34

Summary of Stability Studies for 500/50 µg MDPI (Example 8)

| | Stability data table number (s) | | | |
|---|---|---|---|---|
| | 99 to 106 | 107 to 114 | 115 to 122 | 123 to 130 |
| Batch designation (methodology) | I | J | K | L |
| Lactose batch designation | GG | GG | GG | HH |
| % of lactose fines | 4.5 | 4.5 | 4.5 | 4.2 |
| Data presented 25/60W | 18M | 18M | 18M | 18M |
| 25/75N | 3M | 3M | 3M | 3M |
| 25/75N Aged In Use | 1.5M | 1.5M | 1.5M | 1.5M |
| Specification failures 25/60W | 2 | 0 | 1 | 5 |
| Specification failures 25/75N | 0 | 0 | 0 | 2 |
| Specification failures 25/75N Aged In Use | 0 | 0 | 0 | 4 |

TABLE 35

Stability data for DISKUS ® 100/50 µg 60 Dose Product with overwrap

Packed Batch Number: A

Storage condition 25° C./60% RH

Testing Complete

| | End of life Specification | Storage Time | | | |
|---|---|---|---|---|---|
| | | Initial | 1 Month | 3 Months | 6 Months |
| Particle Size Distribution by Cascade Impaction Salmeterol Sum of stages 1-5 (µg per blister) Individual | 7 to 13 | 15, 15<br>14, 14 | 12, 12<br>13, 13 | 10, 12<br>11, 12 | 12, 11<br>11, 11 |
| Particle Size Distribution by Cascade Impaction Salmeterol Sum of stages 3-4 (µg per blister) Individual | 3 to 8 | 8, 8<br>8, 8 | 7, 7<br>7, 7 | 5, 6<br>6, 6 | 6, 6<br>6, 5 |
| Particle Size Distribution by Cascade Impaction Salmeterol Sum of stages TP0 (µg per blister) Individual | 28 to 42 | 33, 33<br>33, 33 | 32, 32<br>34, 34 | 30, 34<br>32, 34 | 32, 33<br>31, 34 |
| Particle Size Distribution by Cascade Impaction Salmeterol Sum of stages 6, 7 & F (µg per blister) Individual | NGT 0.5 | 0.1, 0.1<br>0.1, 0.2 | 0.1, 0.1<br>0.0, 0.1 | 0.0, 0.0<br>0.0, 0.0 | 0.0, 0.0<br>0.0, 0.0 |

TABLE 36

Stability data for DISKUS ® 100/50 μg 60 Dose Product with overwrap

Packed Batch Number: A

Storage condition 25° C./60% RH Testing Complete

|  | End of life Specification | Initial | Storage Time 9 months | 12 months | 15 months |
|---|---|---|---|---|---|
| Particle Size Distribution by Cascade Impaction Salmeterol Sum of stages 1-5 (μg per blister) Individual | 7 to 13 | 15, 15 14, 14 | 11, 12 12, 12 | 12, 11 11, 12 | 12, 11 11, 12 |
| Particle Size Distribution by Cascade Impaction Salmeterol Sum of stages 3-4 (μg per blister) Individual | 3 to 8 | 8, 8 8, 8 | 5, 6 6, 6 | 6, 5 5, 6 | 6, 6 6, 6 |
| Particle Size Distribution by Cascade Impaction Salmeterol Sum of stages TP0 (μg per blister) Individual | 28 to 42 | 33, 33 33, 33 | 34, 35 34, 33 | 35, 33 35, 34 | 35, 33 34, 34 |
| Particle Size Distribution by Cascade Impaction Salmeterol Sum of stages 6, 7 & F (μg per blister) Individual | NGT 0.5 | 0.1, 0.1 0.1, 0.2 | 0.0, 0.0 0.0, 0.0 | 0.1, 0.1 0.1, 0.1 | 0.1, 0.1 0.1, 0.1 |

TABLE 37

Stability data for DISKUS ® 100/50 μg 60 Dose Product with overwrap

Packed Batch Number: A

Storage condition 25° C./60% RH Testing Complete

| Test | End of life Specification | Initial | Storage Time 1 Month | 3 Months | 6 Months |
|---|---|---|---|---|---|
| Particle Size Distribution by Cascade Impaction Fluticasone Propionate Sum of stages 1-5 (μg per blister) Individual | 15 to 30 | 35, 34 33, 33 | 29, 29 30, 30 | 25, 28 26, 28 | 28, 26 25, 25 |
| Particle Size Distribution by Cascade Impaction Fluticasone Propionate Sum of stages 3-4 (μg per blister) Individual | 6 to 18 | 20, 20 18, 19 | 16, 16 17, 17 | 12, 14 13, 14 | 15, 14 14, 12 |
| Particle Size Distribution by Cascade Impaction Fluticasone Propionate Sum of stages TP0 (μg per blister) Individual | 55 to 80 | 64, 63 63, 63 | 61, 62 65, 66 | 58, 65 62, 65 | 62, 64 61, 66 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 |

TABLE 38

Stability data for DISKUS ® 100/50 μg 60 Dose Product with overwrap

Packed Batch Number: A

Storage condition 25° C./60% RH Testing Complete

| Test | End of life Specification | Initial | Storage Time 9 months | 12 months | 15 months |
|---|---|---|---|---|---|
| Particle Size Distribution by Cascade Impaction Fluticasone Propionate Sum of stages 1-5 (μg per blister) Individual | 15 to 30 | 35, 34 33, 33 | 26, 29 28, 28 | 28, 27 27, 28 | 29, 27 27, 29 |
| Particle Size Distribution by Cascade Impaction Fluticasone Propionate Sum of stages 3-4 (μg per blister) Individual | 6 to 18 | 20, 20 18, 19 | 13, 14 15, 14 | 13, 13 12, 13 | 15, 14 13, 14 |
| Particle Size Distribution by Cascade | 55 to 80 | 64, 63 | 66, 67 | 66, 64 | 68, 64 |

TABLE 38-continued

Stability data for DISKUS ® 100/50 μg 60 Dose Product with overwrap

Packed Batch Number: A

Storage condition 25° C./60% RH
Testing Complete

| Test | End of life Specification | Initial | 9 months | 12 months | 15 months |
|---|---|---|---|---|---|
| Impaction Fluticasone Propionate Sum of stages TP0 (μg per blister) Individual | | 63, 63 | 65, 64 | 68, 66 | 66, 67 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 |

TABLE 39

Stability data for DISKUS ® 100/50 μg 60 Dose Product without overwrap

Packed Batch Number: A

Storage condition 25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (μg per blister) Individual | 7 to 13 | 15, 15 14, 14 | 13, 12 14, 13 | 11, 11 12, 11 | 14, 12 12, 14 | 11, 11 10, 11 |
| Particle Size Distribution by Cascade Impaction Salmeterol Sum of stages 3-4 (μg per blister) Individual | 4 to 8 | 8, 8 8, 8 | 7, 6 8, 8 | 6, 6 7, 6 | 7, 7 6, 7 | 6, 6 5, 6 |
| Particle Size Distribution by Cascade Impaction Salmeterol Sum of stages TP0 (μg per blister) Individual | 28 to 42 | 33, 33 33, 33 | 34, 33 34, 34 | 32, 33 33, 33 | 34, 33 34, 35 | 36, 35 33, 35 |
| Particle Size Distribution by Cascade Impaction Salmeterol Sum of stages 6, 7 & F (μg per blister) Individual | NGT 0.5 | 0.1, 0.1 0.1, 0.2 | 0.2, 0.1 0.1, 0.1 | 0.1, 0.1 0.1, 0.1 | 0.0, 0.0 0.0, 0.0 | 0.0, 0.0 0.0, 0.0 |

Note:
NGT = Not Greater Than

TABLE 40

Stability data for DISKUS ® 100/50 μg 60 Dose Product without overwrap

Packed Batch Number: A

Storage condition 25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Fluticasone Propionate Sum of stages 1-5 (μg per blister) Individual | 17 to 30 | 35, 34 33, 33 | 31, 27 33, 31 | 29, 27 30, 26 | 32, 29 29, 32 | 28, 26 25, 27 |
| Particle Size Distribution by Cascade Impaction Fluticasone Propionate Sum of stages 3-4 (μg per blister) Individual | 9 to 19 | 20, 20 18, 19 | 18, 14 18, 18 | 15, 14 17, 13 | 17, 16 15, 17 | 15, 14 12, 14 |
| Particle Size Distribution by Cascade Impaction Fluticasone Propionate Sum of stages TP0 (μg per blister) Individual | 55 to 80 | 64, 63 63, 63 | 65, 62 65, 64 | 63, 64 65, 66 | 65, 63 65, 67 | 69, 68 65, 69 |
| Particle Size Distribution by Cascade | NGT 1 | 0, 0 | 0, 0 | 0, 0 | 0, 0 | 0, 0 |

TABLE 40-continued

Stability data for DISKUS ® 100/50 µg 60 Dose Product without overwrap

Packed Batch Number: A

Storage condition 25° C./75% RH
Testing Complete

| Test | End of life Specification | Initial | 2 Weeks | 1 Month | 1.5 Months | 3 Months |
|---|---|---|---|---|---|---|
| Impaction Fluticasone Propionate Sum of stages 6, 7 & F (µg per blister) Individual | | 0, 0 | 0, 0 | 0, 0 | 0, 0 | 0, 0 |

TABLE 41

Stability data for DISKUS ® 100/50 µg 60 Dose Product without overwrap
Samples previously stored at 25° C./60% RH with overwrap for 14 months Packed Batch Number: A Storage condition 25° C./75% RH
Testing Complete

| | End of life Specification | Initial | 2 weeks | 1 month | 1.5 months |
|---|---|---|---|---|---|
| Particle Size Distribution by Cascade Impaction Salmeterol Sum of stages 1-5 (µg per blister) Individual | 7 to 13 | 12, 12 13, 12 | 12, 12 11, 12 | 12, 11 11, 11 | 12, 11 11, 12 |
| Particle Size Distribution by Cascade Impaction Salmeterol Sum of stages 3-4 (µg per blister) Individual | 3 to 8 | 6, 6 6, 6 | 6, 7 6, 6 | 5, 5 5, 5 | 6, 6 5, 6 |
| Particle Size Distribution by Cascade Impaction Salmeterol Sum of stages TP0 (µg per blister) Individual | 28 to 42 | 35, 36 36, 36 | 33, 34 33, 34 | 33, 33 32, 34 | 35, 34 33, 34 |
| Particle Size Distribution by Cascade Impaction Salmeterol Sum of stages 6, 7 & F (µg per blister) Individual | NGT 0.5 | 0.1, 0.1 0.1, 0.1 | 0.1, 0.1 0.1, 0.1 | 0.1, 0.1 0.1, 0.1 | 0.1, 0.1 0.1, 0.1 |

TABLE 42

Stability data for DISKUS ® 100/50 µg 60 Dose Product without overwrap
Samples previously stored at 25° C./60% RH with overwrap for 14 months (cont'd)

Packed Batch Number: A

Storage condition 25° C./75% RH
Testing Complete

| Test | End of life Specification | Initial | 2 weeks | 1 month | 1.5 months |
|---|---|---|---|---|---|
| Particle Size Distribution by Cascade Impaction Fluticasone Propionate Sum of stages 1-5 (µg per blister) Individual | 15 to 30 | 28, 29 31, 28 | 30, 28 27, 28 | 28, 27 25, 26 | 28, 28 27, 29 |
| Particle Size Distribution by Cascade Impaction Fluticasone Propionate Sum of stages 3-4 (µg per blister) Individual | 6 to 18 | 14, 15 15, 14 | 15, 16 14, 14 | 13, 13 12, 12 | 14, 14 13, 14 |
| Particle Size Distribution by Cascade Impaction Fluticasone Propionate Sum of stages TP0 (µg per blister) Individual | 55 to 80 | 67, 67 68, 69 | 65, 66 65, 65 | 65, 64 62, 66 | 68, 65 64, 67 |
| Particle Size Distribution by Cascade Impaction Fluticasone Propionate Sum of stages 6, 7 & F (µg per blister) Individual | NGT 1 | 0, 0 0, 0 | 0, 0 0, 0 | 0, 0 0, 0 | 0, 0 0, 0 |

TABLE 43

Stability data for DISKUS ® 100/50 μg 60 Dose Product with overwrap

Packed Batch Number: A

Storage condition 25° C./60% RH
Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (μg per blister) Individual | 7 to 13 | 14, 13 15, 14 | 12, 13 12, 12 | 12, 11 12, 12 | 10, 10 11, 12 |
| Particle Size Distribution by Cascade Impaction Salmeterol Sum of stages 3-4 (μg per blister) Individual | 3 to 8 | 8, 7 8, 8 | 6, 6 7, 6 | 6, 6 6, 6 | 5, 5 6, 6 |
| Particle Size Distribution by Cascade Impaction Salmeterol Sum of stages TP0 (μg per blister) Individual | 28 to 42 | 33, 34 36, 33 | 35, 36 34, 35 | 34, 34 35, 35 | 33, 33 33, 35 |
| Particle Size Distribution by Cascade Impaction Salmeterol Sum of stages 6, 7 & F (μg per blister) Individual | NGT 0.5 | 0.2, 0.1 0.1, 0.2 | 0.1, 0.1 0.1, 0.1 | 0.0, 0.0 0.0, 0.0 | 0.0, 0.0 0.0, 0.0 |

TABLE 44

Stability data for DISKUS ® 100/50 μg 60 Dose Product with overwrap

Packed Batch Number: B

Storage condition 25° C./60% RH
Testing Complete

| Test | End of life Specification | Initial | 9 months | 12 months | 15 months |
|---|---|---|---|---|---|
| Particle Size Distribution by Cascade Impaction Salmeterol Sum of stages 1-5 (μg per blister) Individual | 7 to 13 | 14, 13 15, 14 | 12, 13 13, 12 | 12, 12 12, 11 | 11, 12 11, 10 |
| Particle Size Distribution by Cascade Impaction Salmeterol Sum of stages 3-4 (μg per blister) Individual | 3 to 8 | 8, 7 8, 8 | 6, 6 6, 6 | 6, 6 6, 6 | 5, 6 5, 5 |
| Particle Size Distribution by Cascade Impaction Salmeterol Sum of stages TP0 (μg per blister) Individual | 28 to 42 | 33, 34 36, 33 | 32, 34 32, 33 | 32, 33 34, 31 | 35, 34 33, 35 |
| Particle Size Distribution by Cascade Impaction Salmeterol Sum of stages 6, 7 & F (μg per blister) Individual | NGT 0.5 | 0.2, 0.1 0.1, 0.2 | 0.0, 0.0 0.1, 0.1 | 0.1, 0.1 0.1, 0.1 | 0.1, 0.1 0.1, 0.1 |

TABLE 45

Stability data for DISKUS ® 100/50 μg 60 Dose Product with overwrap

Packed Batch Number: B

Storage condition 25° C./60% RH
Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (μg per blister) Individual | 15 to 30 | 34, 30 35, 33 | 29, 30 29, 29 | 28, 27 28, 28 | 23, 25 27, 28 |
| Particle Size Distribution by Cascade | 6 to 18 | 18, 15 | 14, 15 | 15, 13 | 11, 12 |

TABLE 45-continued

Stability data for DISKUS ® 100/50 μg 60 Dose Product with overwrap

Packed Batch Number: B

Storage condition
25° C./60% RH
Testing Complete

| Test | End of life Specification | Initial | 1 Month | 3 Months | 6 Months |
|---|---|---|---|---|---|
| Impaction Fluticasone Propionate Sum of stages 3-4 (μg per blister) Individual | | 18, 18 | 15, 15 | 13, 14 | 14, 14 |
| Particle Size Distribution by Cascade Impaction Fluticasone Propionate Sum of stages TP0 (μg per blister) Individual | 55 to 80 | 63, 66 68, 62 | 66, 69 65, 66 | 66, 65 67, 66 | 64, 63 64, 67 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 |

TABLE 46

Stability data for DISKUS ® 100/50 μg 60 Dose Product with overwrap

Packed Batch Number: B

Storage condition
25° C./60% RH
Testing Complete

| Test | End of life Specification | Initial | 9 months | 12 months | 15 months |
|---|---|---|---|---|---|
| Particle Size Distribution by Cascade Impaction Fluticasone Propionate Sum of stages 1-5 (μg per blister) Individual | 15 to 30 | 34, 30 35, 33 | 29, 30 30, 29 | 26, 28 29, 26 | 28, 28 27, 24 |
| Particle Size Distribution by Cascade Impaction Fluticasone Propionate Sum of stages 3-4 (μg per blister) Individual | 6 to 18 | 18, 15 18, 18 | 15, 15 14, 15 | 14, 14 14, 14 | 13, 14 13, 12 |
| Particle Size Distribution by Cascade Impaction Fluticasone Propionate Sum of stages TP0 (μg per blister) Individual | 55 to 80 | 63, 66 68, 62 | 62, 66 62, 64 | 61, 64 67, 62 | 68, 65 65, 68 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 |

Note:
NGT = Not Greater Than

TABLE 47

Stability data for DISKUS ® 100/50 μg 60 Dose Product without overwrap

Packed Batch Number: B

Storage condition
25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (μg per blister) Individual | 7 to 13 | 14, 13 15, 14 | 13, 13 13, 13 | 13, 12 12, 11 | 13, 11 13, 12 | 12, 12 14, 12 |
| Particle Size Distribution by Cascade Impaction Salmeterol Sum of stages 3-4 (μg per blister) Individual | 4 to 8 | 8, 7 8, 8 | 7, 7 7, 7 | 7, 7 6, 6 | 7, 6 7, 6 | 6, 6 7, 6 |
| Particle Size Distribution by Cascade | 28 to 42 | 33, 34 | 33, 32 | 34, 35 | 35, 30 | 35, 35 |

TABLE 47-continued

Stability data for DISKUS ® 100/50 µg 60 Dose Product without overwrap

Packed Batch Number: B

Storage condition
25° C./75% RH
Testing Complete

| Test | End of life Specification | Initial | 2 Weeks | 1 Month | 1.5 Months | 3 Months |
|---|---|---|---|---|---|---|
| Impaction Salmeterol Sum of stages TP0 (µg per blister) Individual | | 36, 33 | 34, 33 | 34, 34 | 34, 30 | 36, 35 |
| Particle Size Distribution by Cascade Impaction Salmeterol Sum of stages 6, 7 & F (µg per blister) Individual | NGT 0.5 | 0.2, 0.1 0.1, 0.2 | 0.1, 0.1 0.1, 0.1 | 0.1, 0.1 0.1, 0.1 | 0.0, 0.0 0.0, 0.0 | 0.0, 0.0 0.0, 0.0 |

TABLE 48

Stability data for DISKUS ® 100/50 µg 60 Dose Product without overwrap

Packed Batch Number: B

Storage condition
25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Fluticasone Propionate Sum of stages 1-5 (µg per blister) Individual | 17 to 30 | 34, 30 35, 33 | 31, 31 31, 30 | 31, 29 28, 28 | 31, 27 31, 29 | 28, 28 32, 28 |
| Particle Size Distribution by Cascade Impaction Fluticasone Propionate Sum of stages 3-4 (µg per blister) Individual | 9 to 19 | 18, 15 18, 18 | 16, 17 17, 16 | 17, 16 16, 15 | 16, 14 16, 15 | 13, 14 16, 13 |
| Particle Size Distribution by Cascade Impaction Fluticasone Propionate Sum of stages TP0 (µg per blister) Individual | 55 to 80 | 63, 66 68, 62 | 63, 61 63, 62 | 65, 67 66, 66 | 67, 57 66, 58 | 67, 68 70, 66 |
| Particle Size Distribution by Cascade Impaction Fluticasone Propionate Sum of stages 6, 7 & F (µg per blister) Individual | NGT 1 | 0, 0 0, 0 | 0, 0 0, 0 | 0, 0 0, 0 | 0, 0 0, 0 | 0, 0 0, 0 |

TABLE 49

Stability data for DISKUS ® 100/50 µg 60 Dose Product without overwrap
Samples previously stored at 25° C./60% RH with overwrap for 14 months Packed Batch Number: B Storage condition
25° C./75% RH
Testing Complete

| Test | End of life Specification | Initial | 2 Weeks | 1 Month | 1.5 Months |
|---|---|---|---|---|---|
| Particle Size Distribution by Cascade Impaction Salmeterol Sum of stages 1-5 (µg per blister) Individual | 7 to 13 | 12, 11 11, 11 | 12, 12 11, 11 | 11, 12 11, 12 | 11, 12 11, 12 |
| Particle Size Distribution by Cascade Impaction Salmeterol Sum of stages 3-4 (µg per blister) Individual | 3 to 8 | 6, 5 6, 5 | 6, 6 5, 5 | 5, 6 6, 6 | 5, 6 5, 6 |
| Particle Size Distribution by Cascade Impaction Salmeterol Sum of stages TP0 (µg per blister) Individual | 28 to 42 | 36, 36 31, 35 | 35, 34 33, 34 | 34, 35 29, 33 | 32, 34 34, 36 |
| Particle Size Distribution by Cascade Impaction Salmeterol Sum of stages 6, 7 & F (µg per blister) Individual | NGT 0.5 | 0.1, 0.1 0.1, 0.1 | 0.0, 0.1 0.1, 0.1 | 0.1, 0.1 0.1, 0.1 | 0.1, 0.1 0.1, 0.1 |

TABLE 50

Stability data for DISKUS ® 100/50 µg 60 Dose Product without overwrap
Samples previously stored at 25° C./60% RH with overwrap for 14 months Packed Batch Number: B Storage condition
25° C./75% RH
Testing Complete

| Test | End of life Specification | Initial | 2 Weeks | 1 Month | 1.5 Months |
|---|---|---|---|---|---|
| Particle Size Distribution by Cascade Impaction Fluticasone Propionate Sum of stages 1-5 (µg per blister) Individual | 15 to 30 | 27, 27 27, 26 | 28, 29 26, 27 | 26, 29 28, 28 | 25, 28 26, 29 |
| Particle Size Distribution by Cascade Impaction Fluticasone Propionate Sum of stages 3-4 (µg per blister) Individual | 6 to 18 | 14, 13 14, 13 | 13, 14 13, 13 | 13, 14 13, 14 | 12, 13 12, 14 |
| Particle Size Distribution by Cascade Impaction Fluticasone Propionate Sum of stages TP0 (µg per blister) Individual | 55 to 80 | 68, 69 59, 68 | 68, 66 64, 66 | 64, 68 56, 65 | 62, 67 67, 70 |
| Particle Size Distribution by Cascade Impaction Fluticasone Propionate Sum of stages 6, 7 & F (µg per blister) Individual | NGT 1 | 0, 0 0, 0 | 0, 0 0, 0 | 0, 0 0, 0 | 0, 0 0, 0 |

TABLE 51

Stability data for DISKUS ® 100/50 µg 60 Dose Product with overwrap

Packed Batch Number: C

Storage condition
25° C./60% RH
Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (µg per blister) Individual | 7 to 13 | 16, 14 14, 15 | 13, 12 12, 12 | 12, 12 12, 12 | 12, 12 13, 12 |
| Particle Size Distribution by Cascade Impaction Salmeterol Sum of stages 3-4 (µg per blister) Individual | 4 to 8 | 9, 8 8, 8 | 7, 6 6, 6 | 6, 6 6, 6 | 6, 7 6, 7 |
| Particle Size Distribution by Cascade Impaction Salmeterol Sum of stages TP0 (µg per blister) Individual | 28 to 42 | 33, 33 32, 34 | 33, 34 34, 34 | 34, 35 34, 35 | 34, 32 34, 34 |
| Particle Size Distribution by Cascade Impaction Salmeterol Sum of stages 6, 7 & F (µg per blister) Individual | NGT 0.5 | 0.2, 0.1 0.1, 0.2 | 0.1, 0.1 0.1, 0.1 | 0.0, 0.0 0.0, 0.0 | 0.0, 0.0 0.0, 0.0 |

TABLE 52

Stability data for DISKUS ® 100/50 µg 60 Dose Product with overwrap

Packed Batch Number: C

Storage condition
25° C./60% RH
Testing Complete

| Test | End of life Specification | Initial | 9 months | 12 months | 15 months |
|---|---|---|---|---|---|
| Particle Size Distribution by Cascade Impaction Salmeterol Sum of stages 1-5 (µg per blister) Individual | 7 to 13 | 16, 14 14, 15 | 12, 11 11, 11 | 12, 12 13, 12 | 12, 12 12, 11 |
| Particle Size Distribution by Cascade Impaction Salmeterol Sum of stages 3-4 (µg per blister) Individual | 4 to 8 | 9, 8 8, 8 | 6, 6 5, 6 | 6, 6 6, 6 | 6, 6 6, 6 |
| Particle Size Distribution by Cascade | 28 to 42 | 33, 33 | 32, 33 | 36, 37 | 34, 33 |

TABLE 52-continued

Stability data for DISKUS ® 100/50 μg 60 Dose Product with overwrap

Packed Batch Number: C

Storage condition
25° C./60% RH
Testing Complete

| Test | End of life Specification | Initial | 9 months | 12 months | 15 months |
|---|---|---|---|---|---|
| Impaction Salmeterol Sum of stages TP0 (μg per blister) Individual | | 32, 34 33, 35 | 32, 33 29, 28 | 34, 30 28, 28 | 33, 33 30, 30 |
| Particle Size Distribution by Cascade Impaction Salmeterol Sum of stages 6, 7 & F (μg per blister) Individual | NGT 0.5 | 0.2, 0.1 0.1, 0.2 | 0.0, 0.0 0.0, 0.1 | 0.1, 0.1 0.1, 0.1 | 0.1, 0.1 0.1, 0.1 |

TABLE 53

Stability data for DISKUS ® 100/50 μg 60 Dose Product with overwrap

Packed Batch Number: C

Storage condition
25° C./60% RH
Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (μg per blister) Individual | 17 to 30 | 36, 32 33, 35 | 29, 28 29, 28 | 28, 28 28, 28 | 29, 29 30, 30 |
| Particle Size Distribution by Cascade Impaction Fluticasone Propionate Sum of stages 3-4 (μg per blister) Individual | 9 to 19 | 20, 18 17, 20 | 15, 14 14, 14 | 14, 14 14, 14 | 14, 16 15, 15 |
| Particle Size Distribution by Cascade Impaction Fluticasone Propionate Sum of stages TP0 (μg per blister) Individual | 55 to 80 | 59, 61 59, 62 | 64, 63 63, 64 | 64, 66 65, 66 | 65, 63 67, 65 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 |

TABLE 54

Stability data for DISKUS ® 100/50 μg 60 Dose Product with overwrap

Packed Batch Number: C

Storage condition
25° C./60% RH
Testing Complete

| Test | End of life Specification | Initial | 9 months | 12 months | 15 months |
|---|---|---|---|---|---|
| Particle Size Distribution by Cascade Impaction Fluticasone Propionate Sum of stages 1-5 (μg per blister) Individual | 17 to 30 | 36, 32 33, 35 | 28, 26 25, 27 | 28, 28 29, 29 | 28, 28 27, 27 |
| Particle Size Distribution by Cascade Impaction Fluticasone Propionate Sum of stages 3-4 (μg per blister) Individual | 9 to 19 | 20, 18 17, 20 | 14, 13 12, 13 | 14, 15 15, 15 | 13, 14 13, 13 |
| Particle Size Distribution by Cascade Impaction Fluticasone Propionate Sum of stages TP0 (μg per blister) Individual | 55 to 80 | 59, 61 59, 62 | 61, 62 64, 64 | 67, 71 65, 59 | 65, 64 63, 64 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 |

TABLE 55

Stability data for DISKUS ® 100/50 μg 60 Dose Product without overwrap

Packed Batch Number: C

Storage condition
25° C./75% RH
Testing Complete

| Test | End of life Specification | Initial | 2 Weeks | 1 Month | 1.5 Months | 3 Months |
|---|---|---|---|---|---|---|
| | | | | Storage Time | | |
| Particle Size Distribution by Cascade Impaction Salmeterol Sum of stages 1-5 (μg per blister) Individual | 7 to 13 | 16, 14 14, 15 | 14, 13 13, 13 | 12, 12 12, 13 | 13, 13 13, 14 | 12, 12 12, 13 |
| Particle Size Distribution by Cascade Impaction Salmeterol Sum of stages 3-4 (μg per blister) Individual | 4 to 8 | 9, 8 8, 8 | 8, 7 7, 7 | 7, 7 7, 7 | 7, 7 7, 7 | 6, 6 6, 6 |
| Particle Size Distribution by Cascade Impaction Salmeterol Sum of stages TP0 (μg per blister) Individual | 28 to 42 | 33, 33 32, 34 | 34, 35 34, 34 | 34, 34 35, 35 | 33, 32 35, 34 | 35, 34 34, 34 |
| Particle Size Distribution by Cascade Impaction Salmeterol Sum of stages 6, 7 & F (μg per blister) Individual | NGT 0.5 | 0.2, 0.1 0.1, 0.2 | 0.1, 0.1 0.1, 0.2 | 0.1, 0.1 0.1, 0.1 | 0.0, 0.0 0.0, 0.0 | 0.0, 0.0 0.0, 0.0 |

TABLE 56

Stability data for DISKUS ® 100/50 μg 60 Dose Product without overwrap

Packed Batch Number: C

Storage condition
25° C./75% RH
Testing Complete

| Test | End of life Specification | Initial | 2 Weeks | 1 Month | 1.5 Months | 3 Months |
|---|---|---|---|---|---|---|
| | | | | Storage Time | | |
| Particle Size Distribution by Cascade Impaction Fluticasone Propionate Sum of stages 1-5 (μg per blister) Individual | 17 to 30 | 36, 32 33, 35 | 33, 31 31, 30 | 29, 29 28, 30 | 31, 29 31, 32 | 28, 27 28, 29 |
| Particle Size Distribution by Cascade Impaction Fluticasone Propionate Sum of stages 3-4 (μg per blister) Individual | 9 to 19 | 20, 18 17, 20 | 17, 16 16, 16 | 15, 16 15, 16 | 16, 15 16, 17 | 13, 13 14, 15 |
| Particle Size Distribution by Cascade Impaction Fluticasone Propionate Sum of stages TP0 (μg per blister) Individual | 55 to 80 | 59, 61 59, 62 | 64, 65 63, 63 | 65, 64 67, 66 | 62, 60 65, 68 | 65, 70 64, 66 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 | 0, 0 0, 0 |

TABLE 57

Stability data for DISKUS ® 100/50 μg 60 Dose Product without overwrap
Samples previously stored at 25° C./60% RH with overwrap for 14 months Packed Batch Number: C Storage condition
25° C./75% RH
Testing Complete

| Test | End of life Specification | Initial | 2 Weeks | 1 Month | 1.5 Months |
|---|---|---|---|---|---|
| | | | | Storage Time | |
| Particle Size Distribution by Cascade Impaction Salmeterol Sum of stages 1-5 (μg per blister) Individual | 7 to 13 | 12, 12 11, 16 | 12, 12 12, 12 | 11, 12 12, 12 | 12, 11 11, 12 |
| Particle Size Distribution by Cascade | 3 to 8 | 6, 6 | 6, 6 | 5, 6 | 6, 5 |

TABLE 57-continued

Stability data for DISKUS ® 100/50 μg 60 Dose Product without overwrap
Samples previously stored at 25° C./60% RH with overwrap for 14 months Packed Batch Number: C Storage condition
25° C./75% RH
Testing Complete

| Test | End of life Specification | Initial | 2 Weeks | 1 Month | 1.5 Months |
|---|---|---|---|---|---|
| Impaction Salmeterol Sum of stages 3-4 (μg per blister) Individual | | 5, 7 | 6, 6 | 6, 6 | 5, 6 |
| Particle Size Distribution by Cascade Impaction Salmeterol Sum of stages TP0 (μg per blister) Individual | 28 to 42 | 34, 35 32, 34 | 34, 35 32, 34 | 33, 33 33, 33 | 34, 35 35, 35 |
| Particle Size Distribution by Cascade Impaction Salmeterol Sum of stages 6, 7 & F (μg per blister) Individual | NGT 0.5 | 0.1, 0.1 0.1, 0.1 | 0.1, 0.1 0.1, 0.1 | 0.1, 0.0 0.1, 0.0 | 0.1, 0.1 0.1, 0.1 |

TABLE 58

Stability data for DISKUS ® 100/50 μg 60 Dose Product without overwrap
Samples previously stored at 25° C./60% RH with overwrap for 14 months Packed Batch Number: C Storage condition
25° C./75% RH
Testing Complete

| Test | End of life Specification | Initial | 2 Weeks | 1 Month | 1.5 Months |
|---|---|---|---|---|---|
| Particle Size Distribution by Cascade Impaction Fluticasone Propionate Sum of stages 1-5 (μg per blister) Individual | 15 to 30 | 29, 28 27, 30 | 27, 29 28, 27 | 26, 27 28, 28 | 28, 27 25, 27 |
| Particle Size Distribution by Cascade Impaction Fluticasone Propionate Sum of stages 3-4 (μg per blister) Individual | 6 to 18 | 15, 14 13, 15 | 13, 14 15, 14 | 13, 13 14, 13 | 14, 13 12, 13 |
| Particle Size Distribution by Cascade Impaction Fluticasone Propionate Sum of stages TP0 (μg per blister) Individual | 55 to 80 | 68, 66 63, 66 | 67, 67 65, 64 | 61, 64 64, 64 | 66, 66 68, 66 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 |

TABLE 59

Stability data for DISKUS ® 100/50 μg 60 Dose Product with overwrap

Packed Batch Number: D

Storage condition
25° C./60% RH
Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (μg per blister) Individual | 7 to 13 | 12, 11 12, 11 | 11, 10 10, 11 | 10, 10 10, 9 | 9, 10 9, 10 |
| Particle Size Distribution by Cascade Impaction Salmeterol Sum of stages 3-4 (μg per blister) Individual | 3 to 8 | 6, 6 6, 6 | 5, 5 5, 6 | 5, 5 5, 5 | 5, 5 4, 5 |
| Particle Size Distribution by Cascade | 28 to 42 | 36, 36 | 36, 38 | 38, 38 | 37, 37 |

TABLE 59-continued

Stability data for DISKUS ® 100/50 µg 60 Dose Product with overwrap

Packed Batch Number: D

Storage condition 25° C./60% RH
Testing Complete

| Test | End of life Specification | Initial | 1 Month | 3 Months | 6 Months |
|---|---|---|---|---|---|
| Impaction Salmeterol Sum of stages TP0 (µg per blister) Individual | | 36, 36 | 36, 35 | 38, 37 | 35, 38 |
| Particle Size Distribution by Cascade Impaction Salmeterol Sum of stages 6, 7 & F (µg per blister) Individual | NGT 0.5 | 0.1, 0.1 0.1, 0.1 | 0.1, 0.1 0.1, 0.1 | 0.0, 0.0 0.0, 0.0 | 0.0, 0.0 0.0, 0.0 |

Note:
NGT = Not Greater Than

TABLE 60

Stability data for DISKUS ® 100/50 µg 60 Dose Product with overwrap

Packed Batch Number: D

Storage condition 25° C./60% RH
Testing Complete

| Test | End of life Specification | Initial | 9 months | 12 months | 15 months |
|---|---|---|---|---|---|
| Particle Size Distribution by Cascade Impaction Salmeterol Sum of stages 1-5 (µg per blister) Individual | 7 to 13 | 12, 11 12, 11 | 10, 9 10, 10 | 9, 9 10, 9 | 9, 9 9, 8 |
| Particle Size Distribution by Cascade Impaction Salmeterol Sum of stages 3-4 (µg per blister) Individual | 3 to 8 | 6, 6 6, 6 | 5, 4 5, 5 | 4, 4 4, 3 | 4, 4 4, 3 |
| Particle Size Distribution by Cascade Impaction Salmeterol Sum of stages TP0 (µg per blister) Individual | 28 to 42 | 36, 36 36, 36 | 36, 37 37, 37 | 39, 38 39, 39 | 37, 35 37, 36 |
| Particle Size Distribution by Cascade Impaction Salmeterol Sum of stages 6, 7 & F (µg per blister) Individual | NGT 0.5 | 0.1, 0.1 0.1, 0.1 | 0.0, 0.0 0.0, 0.0 | 0.0, 0.0 0.1, 0.0 | 0.0, 0.0 0.0, 0.0 |

TABLE 61

Stability data for DISKUS ® 100/50 µg 60 Dose Product with overwrap

Packed Batch Number: D

Storage condition 25° C./60% RH
Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (µg per blister) Individual | 15 to 30 | 28, 26 28, 26 | 26, 25 23, 25 | 24, 24 24, 23 | 22, 24 21, 23 |
| Particle Size Distribution by Cascade Impaction Fluticasone Propionate Sum of stages 3-4 (µg per blister) Individual | 6 to 18 | 15, 14 15, 14 | 13, 12 12, 13 | 12, 12 12, 11 | 11, 11 9, 11 |
| Particle Size Distribution by Cascade Impaction Fluticasone Propionate Sum of stages TP0 (µg per blister) Individual | 55 to 80 | 68, 68 68, 69 | 70, 72 70, 66 | 73, 74 73, 71 | 71, 72 68, 74 |
| Particle Size Distribution by Cascade | NGT 1 | 0, 0 | 0, 0 | 0, 0 | 0, 0 |

TABLE 61-continued

Stability data for DISKUS ® 100/50 µg 60 Dose Product with overwrap

Packed Batch Number: D

Storage condition 25° C./60% RH
Testing Complete

| Test | End of life Specification | Initial | 1 Month | 3 Months | 6 Months |
|---|---|---|---|---|---|
| Impaction Fluticasone Propionate Sum of stages 6, 7 & F (µg per blister) Individual | | 0, 0 | 0, 0 | 0, 0 | 0, 0 |

TABLE 62

Stability data for DISKUS ® 100/50 µg 60 Dose Product with overwrap

Packed Batch Number: D

Storage condition 25° C./60% RH
Testing Complete

| Test | End of life Specification | Initial | 9 months | 12 months | 15 months |
|---|---|---|---|---|---|
| Particle Size Distribution by Cascade Impaction Fluticasone Propionate Sum of stages 1-5 (µg per blister) Individual | 15 to 30 | 28, 26<br>28, 26 | 24, 22<br>23, 23 | 20, 20<br>23, 20 | 21, 21<br>21, 19 |
| Particle Size Distribution by Cascade Impaction Fluticasone Propionate Sum of stages 3-4 (µg per blister) Individual | 6 to 18 | 15, 14<br>15, 14 | 11, 10<br>12, 11 | 8, 9<br>10, 8 | 10, 9<br>9, 8 |
| Particle Size Distribution by Cascade Impaction Fluticasone Propionate Sum of stages TP0 (µg per blister) Individual | 55 to 80 | 68, 68<br>68, 69 | 71, 71<br>73, 71 | 74, 73<br>76, 76 | 72, 69<br>73, 71 |
| Particle Size Distribution by Cascade Impaction Fluticasone Propionate Sum of stages 6, 7 & F (µg per blister) Individual | NGT 1 | 0, 0<br>0, 0 | 0, 0<br>0, 0 | 0, 0<br>0, 0 | 0, 0<br>0, 0 |

TABLE 63

Stability data for DISKUS ® 100/50 µg 60 Dose Product without overwrap

Packed Batch Number: D

Storage condition 25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (µg per blister) Individual | 7 to 13 | 12, 11<br>12, 11 | 10, 11<br>11, 11 | 11, 11<br>11, 11 | 11, 10<br>11, 11 | 10, 9<br>9, 9 |
| Particle Size Distribution by Cascade Impaction Salmeterol Sum of stages 3-4 (µg per blister) Individual | 4 to 8 | 6, 6<br>6, 6 | 5, 6<br>5, 5 | 6, 6<br>6, 5 | 6, 5<br>6, 6 | 5, 5<br>5, 5 |
| Particle Size Distribution by Cascade Impaction Salmeterol Sum of stages TP0 (µg per blister) Individual | 28 to 42 | 36, 36<br>36, 36 | 36, 36<br>37, 38 | 37, 36<br>37, 35 | 35, 32<br>33, 36 | 39, 38<br>37, 37 |
| Particle Size Distribution by Cascade Impaction Salmeterol Sum of stages 6, 7 & F (µg per blister) Individual | NGT 0.5 | 0.1, 0.1<br>0.1, 0.1 | 0.1, 0.1<br>0.1, 0.1 | 0.1, 0.1<br>0.1, 0.1 | 0.0, 0.0<br>0.0, 0.0 | 0.0, 0.0<br>0.0, 0.0 |

TABLE 64

Stability data for DISKUS ® 100/50 μg 60 Dose Product without overwrap

Packed Batch Number: D

Storage condition
25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Fluticasone Propionate Sum of stages 1-5 (μg per blister) Individual | 17 to 30 | 28, 26 28, 26 | 24, 26 25, 25 | 26, 26 27, 25 | 25, 25 25, 26 | 23, 22 22, 23 |
| Particle Size Distribution by Cascade Impaction Fluticasone Propionate Sum of stages 3-4 (μg per blister) Individual | 9 to 19 | 15, 14 15, 14 | 12, 14 13, 13 | 14, 14 14, 13 | 13, 13 14, 14 | 12, 11 11, 11 |
| Particle Size Distribution by Cascade Impaction Fluticasone Propionate Sum of stages TP0 (μg per blister) Individual | 55 to 80 | 68, 68 68, 69 | 69, 69 71, 71 | 71, 69 71, 67 | 68, 62 67, 69 | 75, 74 72, 71 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 | 0, 0 0, 0 |

TABLE 65

Stability data for DISKUS ® 100/50 μg 60 Dose Product without overwrap
Samples previously stored at 25° C./60% RH with overwrap for 14 months Packed Batch Number: D Storage condition
25° C./75% RH
Testing Complete

| Test | End of life Specification | Initial | 0.5 Months | 1 Month | 1.5 Months |
|---|---|---|---|---|---|
| Particle Size Distribution by Cascade Impaction Salmeterol Sum of stages 1-5 (μg per blister) Individual | 7 to 13 | 9, 10 10, 9 | 9, 10 10, 9 | 9, 10 9, 8 | 8, 9 9, 9 |
| Particle Size Distribution by Cascade Impaction Salmeterol Sum of stages 3-4 (μg per blister) Individual | 3 to 8 | 4, 5 5, 5 | 4, 5 4, 4 | 4, 5 4, 3 | 4, 4 4, 4 |
| Particle Size Distribution by Cascade Impaction Salmeterol Sum of stages TP0 (μg per blister) Individual | 28 to 42 | 35, 37 37, 36 | 39, 38 38, 38 | 37, 38 36, 36 | 32, 38 34, 37 |
| Particle Size Distribution by Cascade Impaction Salmeterol Sum of stages 6, 7 & F (μg per blister) Individual | NGT 0.5 | 0.1, 0.1 0.1, 0.1 | 0.1, 0.1 0.1, 0.1 | 0.0, 0.1 0.1, 0.0 | 0.1, 0.1 0.1, 0.1 |

TABLE 66

Stability data for DISKUS ® 100/50 μg 60 Dose Product without overwrap (Cont'd)
Samples previously stored at 25° C./60% RH with overwrap for 14 months Packed Batch Number: D Storage condition
25° C./75% RH
Testing Complete

| Test | End of life Specification | Initial | 0.5 Months | 1 Month | 1.5 Months |
|---|---|---|---|---|---|
| Particle Size Distribution by Cascade Impaction Fluticasone Propionate Sum of stages 1-5 (μg per blister) Individual | 15 to 30 | 22, 23 23, 22 | 22, 24 23, 23 | 21, 23 22, 20 | 21, 22 21, 21 |

TABLE 66-continued

Stability data for DISKUS ® 100/50 μg 60 Dose Product without overwrap (Cont'd)
Samples previously stored at 25° C./60% RH with overwrap for 14 months Packed Batch Number: D Storage condition
25° C./75% RH
Testing Complete

| Test | End of life Specification | Initial | 0.5 Months | 1 Month | 1.5 Months |
|---|---|---|---|---|---|
| Particle Size Distribution by Cascade Impaction Fluticasone Propionate Sum of stages 3-4 (μg per blister) Individual | 6 to 18 | 10, 11 11, 11 | 10, 11 11, 10 | 9, 11 10, 8 | 9, 10 10, 9 |
| Particle Size Distribution by Cascade Impaction Fluticasone Propionate Sum of stages TP0 (μg per blister) Individual | 55 to 80 | 68, 72 72, 71 | 76, 76 75, 74 | 72, 73 70, 70 | 65, 74 66, 73 |
| Particle Size Distribution by Cascade Impaction Fluticasone Propionate Sum of stages 6, 7 & F (μg per blister) Individual | NGT 1 | 0, 0 0, 0 | 0, 0 0, 0 | 0, 0 0, 0 | 0, 0 0, 0 |

TABLE 67

Stability data for DISKUS ® 250/50 μg 60 Dose Product with overwrap

Packed Batch Number: E

Storage condition
25° C./60% RH
Testing Complete

| Test | End of life Specification | Initial | 1 month | 3 months | 6 months |
|---|---|---|---|---|---|
| Particle Size Distribution by Cascade Impaction Salmeterol Sum of stages 1-5 (μg per blister) Individual | 7 to 13 | 12, 11 12, 12 | 11, 11 10, 11 | 10, 10 11, 11 | 10, 8 9, 9 |
| Particle Size Distribution by Cascade Impaction Salmeterol Sum of stages 3-4 (μg per blister) Individual | 3 to 8 | 7, 6 7, 7 | 6, 5 5, 6 | 5, 6 6, 6 | 5, 4 5, 4 |
| Particle Size Distribution by Cascade Impaction Salmeterol Sum of stages TP0 (μg per blister) Individual | 28 to 42 | 33, 32 34, 34 | 36, 37 36, 36 | 35, 34 35, 36 | 37, 35 33, 35 |
| Particle Size Distribution by Cascade Impaction Salmeterol Sum of stages 6, 7 & F (μg per blister) Individual | NGT 0.5 | 0.1, 0.1 0.1, 0.1 | 0.1, 0.1 0.1, 0.1 | 0.0, 0.0 0.0, 0.0 | 0.0, 0.0 0.0, 0.0 |

TABLE 68

Stability data for DISKUS ® 250/50 μg 60 Dose Product with overwrap

Packed Batch Number: E

Storage condition
25° C./60% RH
Testing Complete

| Test | End of life Specification | Initial | 9 months | 12 months | 18 months |
|---|---|---|---|---|---|
| Particle Size Distribution by Cascade Impaction Salmeterol Sum of stages 1-5 (μg per blister) Individual | 7 to 13 | 12, 11 12, 12 | 10, 10 9, 11 | 11, 10 10, 11 | 10, 9 9, 9 |
| Particle Size Distribution by Cascade Impaction Salmeterol Sum of stages 3-4 (μg per blister) Individual | 3 to 8 | 7, 6 7, 7 | 5, 5 5, 6 | 5, 5 5, 5 | 5, 4 4, 4 |
| Particle Size Distribution by Cascade | 28 to 42 | 33, 32 | 36, 35 | 37, 35 | 36, 34 |

TABLE 68-continued

Stability data for DISKUS ® 250/50 µg 60 Dose Product with overwrap

Packed Batch Number: E

Storage condition 25° C./60% RH
Testing Complete

| Test | End of life Specification | Initial | 9 months | 12 months | 18 months |
|---|---|---|---|---|---|
| Impaction Salmeterol Sum of stages TP0 (µg per blister) Individual | | 34, 34 | 33, 36 | 34, 37 | 34, 36 |
| Particle Size Distribution by Cascade Impaction Salmeterol Sum of stages 6, 7 & F (µg per blister) Individual | NGT 0.5 | 0.1, 0.1 0.1, 0.1 | 0.0, 0.0 0.0, 0.0 | 0.1, 0.1 0.1, 0.1 | 0.1, 0.0 0.0, 0.0 |

TABLE 69

Stability data for DISKUS ® 250/50 µg 60 Dose Product with overwrap

Packed Batch Number: E

Storage condition 25° C./60% RH
Testing Complete

| Test | End of life Specification | Initial | 1 month | 3 months | 6 months |
|---|---|---|---|---|---|
| Particle Size Distribution by Cascade Impaction Fluticasone Propionate Sum of stages 1-5 (µg per blister) Individual | 42 to 73 | 66, 61 67, 69 | 62, 61 59, 62 | 55, 59 63, 63 | 58, 48 54, 51 |
| Particle Size Distribution by Cascade Impaction Fluticasone Propionate Sum of stages 3-4 (µg per blister) Individual | 19 to 45 | 39, 34 39, 41 | 32, 31 30, 32 | 29, 32 34, 34 | 29, 22 27, 26 |
| Particle Size Distribution by Cascade Impaction Fluticasone Propionate Sum of stages TP0 (µg per blister) Individual | 140 to 200 | 159, 154 161, 161 | 173, 177 170, 174 | 169, 165 169, 173 | 181, 171 163, 168 |
| Particle Size Distribution by Cascade Impaction Fluticasone Propionate Sum of stages 6, 7 & F (µg per blister) Individual | <2 | 0, 0 0, 0 | 0, 0 0, 0 | 0, 0 0, 0 | 0, 0 0, 0 |

TABLE 70

Stability data for DISKUS ® 250/50 µg 60 Dose Product with overwrap

Packed Batch Number: E

Storage condition 25° C./60% RH
Testing Complete

| Test | End of life Specification | Initial | 9 months | 12 months | 18 months |
|---|---|---|---|---|---|
| Particle Size Distribution by Cascade Impaction Fluticasone Propionate Sum of stages 1-5 (µg per blister) Individual | 42 to 73 | 66, 61 67, 69 | 60, 55 54, 62 | 64, 57 55, 61 | 56, 50 54, 54 |
| Particle Size Distribution by Cascade Impaction Fluticasone Propionate Sum of stages 3-4 (µg per blister) Individual | 19 to 45 | 39, 34 39, 41 | 30, 27 28, 32 | 31, 28 27, 29 | 26, 23 25, 24 |
| Particle Size Distribution by Cascade Impaction Fluticasone Propionate Sum of stages TP0 (µg per blister) Individual | 140 to 200 | 159, 154 161, 161 | 177, 169 162, 173 | 176, 179 167, 180 | 174, 165 178, 177 |
| Particle Size Distribution by Cascade Impaction Fluticasone Propionate Sum of stages 6, 7 & F (µg per blister) Individual | <2 | 0, 0 0, 0 | 0, 0 0, 0 | 0, 0 0, 0 | 0, 0 0, 0 |

TABLE 71

Stability data for DISKUS ® 250/50 μg 60 Dose Product without overwrap

Packed Batch Number: E

Storage condition
25° C./75% RH
Testing Complete

| Test | End of life Specification | Initial | 2 Weeks | 1 month | 1.5 months | 3 months |
|---|---|---|---|---|---|---|
| Particle Size Distribution by Cascade Impaction Salmeterol Sum of stages 1-5 (μg per blister) Individual | 7 to 13 | 12, 11 12, 12 | 12, 14 11, 12 | 11, 11 10, 11 | 12, 11 11, 11 | 10, 10 10, 10 |
| Particle Size Distribution by Cascade Impaction Salmeterol Sum of stages 3-4 (μg per blister) Individual | 3 to 8 | 7, 6 7, 7 | 6, 8 6, 6 | 5, 6 5, 6 | 7, 6 6, 6 | 5, 5 5, 5 |
| Particle Size Distribution by Cascade Impaction Salmeterol Sum of stages TP0 (μg per blister) Individual | 28 to 42 | 33, 32 34, 34 | 35, 44 34, 36 | 35, 36 35, 36 | 36, 34 36, 35 | 37, 36 36, 37 |
| Particle Size Distribution by Cascade Impaction Salmeterol Sum of stages 6, 7 & F (μg per blister) Individual | NGT 0.5 | 0.1, 0.1 0.1, 0.1 | 0.0, 0.0 0.0, 0.0 | 0.0, 0.0 0.0, 0.0 | 0.0, 0.0 0.0, 0.0 | 0.0, 0.0 0.0, 0.0 |

TABLE 72

Stability data for DISKUS ® 250/50 μg 60 Dose Product without overwrap

Packed Batch Number: E

Storage condition
25° C./75% RH
Testing Complete

| Test | End of life Specification | Initial | 2 Weeks | 1 month | 1.5 months | 3 months |
|---|---|---|---|---|---|---|
| Particle Size Distribution by Cascade Impaction Fluticasone Propionate Sum of stages 1-5 (μg per blister) Individual | 42 to 73 | 66, 61 67, 69 | 64, 77 61, 65 | 61, 63 58, 64 | 68, 65 63, 64 | 59, 57 58, 55 |
| Particle Size Distribution by Cascade Impaction Fluticasone Propionate Sum of stages 3-4 (μg per blister) Individual | 19 to 45 | 39, 34 39, 41 | 35, 44 34, 36 | 31, 33 30, 33 | 38, 36 35, 35 | 31, 30 29, 28 |
| Particle Size Distribution by Cascade Impaction Fluticasone Propionate Sum of stages TP0 (μg per blister) Individual | 140 to 200 | 159, 154 161, 161 | 159, 188 162, 165 | 166, 172 170, 175 | 172, 162 170, 168 | 177, 174 176, 177 |
| Particle Size Distribution by Cascade Impaction Fluticasone Propionate Sum of stages 6, 7 & F (μg per blister) Individual | <2 | 0, 0 0, 0 | 0, 1 0, 0 | 0, 0 0, 0 | 0, 0 0, 0 | 0, 0 0, 0 |

TABLE 73

Stability data for DISKUS ® 250/50 μg 60 Dose Product without overwrap
Samples previously stored at 25° C./60% RH for 17 months with overwrap Packed Batch Number: E Storage condition
25° C./75% RH
Testing Complete

| Test | End of life Specification | Initial | 2 Weeks | 1 month | 1.5 months |
|---|---|---|---|---|---|
| Particle Size Distribution by Cascade Impaction Salmeterol Sum of stages 1-5 (μg per blister) Individual | 7 to 13 | 10, 10 9, 9 | 10, 10 10, 10 | (a) 10 | 10, 10 9, 10 |
| Particle Size Distribution by Cascade | 3 to 8 | 5, 5 | 5, 5 | (a) | 5, 5 |

TABLE 73-continued

Stability data for DISKUS ® 250/50 µg 60 Dose Product without overwrap
Samples previously stored at 25° C./60% RH for 17 months with overwrap Packed Batch Number: E Storage condition
25° C./75% RH
Testing Complete

| Test | End of life Specification | Initial | 2 Weeks | 1 month | 1.5 months |
|---|---|---|---|---|---|
| Impaction Salmeterol Sum of stages 3-4 (µg per blister) Individual | | 4, 4 | 5, 5 | 4 | 4, 5 |
| Particle Size Distribution by Cascade Impaction Salmeterol Sum of stages TP0 (µg per blister) Individual | 28 to 42 | 35, 37 36, 36 | 35, 37 37, 35 | (a) 36 | 35, 36 35, 37 |
| Particle Size Distribution by Cascade Impaction Salmeterol Sum of stages 6, 7 & F (µg per blister) Individual | NGT 0.5 | 0.1, 0.1 0.1, 0.1 | 0.0, 0.1 0.1, 0.1 | (a) 0.0 | 0.1, 0.1 0.1, 0.1 |

TABLE 74

Stability data for DISKUS ® 250/50 µg 60 Dose Product without overwrap
Samples previously stored at 25° C./60% RH for 17 months with overwrap (cont'd)

Packed Batch Number: E

Storage condition
25° C./75% RH
Testing Complete

| Test | End of life Specification | Initial | 2 Weeks | 1 month | 1.5 months |
|---|---|---|---|---|---|
| Particle Size Distribution by Cascade Impaction Fluticasone Propionate Sum of stages 1-5 (µg per blister) Individual | 42 to 73 | 57, 56 54, 54 | 58, 56 57, 55 | (a) 57 | 55, 57 52, 55 |
| Particle Size Distribution by Cascade Impaction Fluticasone Propionate Sum of stages 3-4 (µg per blister) Individual | 19 to 45 | 29, 26 25, 25 | 27, 26 27, 26 | (a) 25 | 28, 30 25, 27 |
| Particle Size Distribution by Cascade Impaction Fluticasone Propionate Sum of stages TP0 (µg per blister) Individual | 140 to 200 | 170, 182 176, 175 | 171, 178 178, 168 | (a) 182 | 171, 178 174, 184 |
| Particle Size Distribution by Cascade Impaction Fluticasone Propionate Sum of stages 6, 7 & F (µg per blister) Individual | <2 | 0, 0 0, 0 | 0, 0 0, 0 | (a) 0 | 0, 0 0, 0 |

TABLE 75

Stability data for DISKUS ® 250/50 µg 60 Dose Product with overwrap

Packed Batch Number: F

Storage condition
25° C./60% RH
Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (µg per blister) Individual | 7 to 13 | 13, 12 13, 12 12, 12 | 12, 11 11, 11 | 11, 11 11, 11 | 11, 9 10, 10 |
| Particle Size Distribution by Cascade Impaction Salmeterol Sum of stages 3-4 (µg per blister) Individual | 3 to 8 | 8, 7 7, 7 7, 7 | 7, 7 6, 6 | 6, 6 6, 6 | 5, 4 5, 5 |
| Particle Size Distribution by Cascade | 28 to 42 | 36, 35 | 36, 35 | 35, 35 | 36, 34 |

TABLE 75-continued

Stability data for DISKUS ® 250/50 µg 60 Dose Product with overwrap

Packed Batch Number: F

Storage condition
25° C./60% RH
Testing Complete

| Test | End of life Specification | Initial | 1 Month | 3 Months | 6 Months |
|---|---|---|---|---|---|
| Impaction Salmeterol Sum of stages TP0 (µg per blister) Individual | | 36, 35 36, 33 | 36, 35 | 33, 31 | 36, 37 |
| Particle Size Distribution by Cascade Impaction Salmeterol Sum of stages 6, 7 & F (µg per blister) Individual | NGT 0.5 | 0.1, 0.1 0.1, 0.1 0.1, 0.1 | 0.1, 0.1 0.1, 0.1 | 0.0, 0.1 0.1, 0.0 | 0.0, 0.0 0.0, 0.0 |

TABLE 76

Stability data for DISKUS ® 250/50 µg 60 Dose Product with overwrap

Packed Batch Number: F

Storage condition
25° C./60% RH
Testing Complete

| Test | End of life Specification | Initial | 9 Months | 12 Months | 18 Months |
|---|---|---|---|---|---|
| Particle Size Distribution by Cascade Impaction Salmeterol Sum of stages 1-5 (µg per blister) Individual | 7 to 13 | 13, 12 13, 12 12, 12 | 11, 11 11, 12 | 9, 10 9, 10 | 9, 10 10, 10 |
| Particle Size Distribution by Cascade Impaction Salmeterol Sum of stages 3-4 (µg per blister) Individual | 3 to 8 | 8, 7 7, 7 7, 7 | 6, 6 5, 6 | 4, 4 4, 5 | 4, 5 5, 5 |
| Particle Size Distribution by Cascade Impaction Salmeterol Sum of stages TP0 (µg per blister) Individual | 28 to 42 | 36, 35 36, 35 36, 33 | 34, 36 36, 36 | 35, 37 36, 38 | 37, 35 35, 34 |
| Particle Size Distribution by Cascade Impaction Salmeterol Sum of stages 6, 7 & F (µg per blister) Individual | NGT 0.5 | 0.1, 0.1 0.1, 0.1 0.1, 0.1 | 0.0, 0.0 0.0, 0.0 | 0.0, 0.0 0.0, 0.0 | 0.1, 0.1 0.1, 0.1 |

TABLE 77

Stability data for DISKUS ® 250/50 µg 60 Dose Product with overwrap

Packed Batch Number: F

Storage condition
25° C./60% RH
Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (µg per blister) Individual | 42 to 73 | 76, 70 73, 70 68, 72 | 67, 65 62, 61 | 63, 61 64, 63 | 62, 53 61, 58 |
| Particle Size Distribution by Cascade Impaction Fluticasone Propionate Sum of stages 3-4 (µg per blister) Individual | 19 to 45 | 46, 40 43, 42 39, 41 | 39, 39 36, 35 | 34, 33 36, 34 | 32, 26 31, 28 |
| Particle Size Distribution by Cascade Impaction Fluticasone Propionate Sum of stages TP0 (µg per blister) Individual | 140 to 200 | 173, 170 170, 168 174, 159 | 176, 169 172, 172 | 170, 171 163, 154 | 175, 166 177, 180 |
| Particle Size Distribution by Cascade Impaction Fluticasone Propionate Sum of stages 6, 7 & F (µg per blister) Individual | <2 | 1, 0 1, 0 0, 0 | 0, 0 0, 0 | 0, 0 0, 0 | 0, 0 0, 0 |

TABLE 78

Stability data for DISKUS ® 250/50 µg 60 Dose Product with overwrap

Packed Batch Number: F

Storage condition 25° C./60% RH
Testing Complete

| Test | End of life Specification | Initial | 9 Months | 12 Months | 18 Months |
|---|---|---|---|---|---|
| Particle Size Distribution by Cascade Impaction Fluticasone Propionate Sum of stages 1-5 (µg per blister) Individual | 42 to 73 | 76, 70 73, 70 68, 72 | 65, 65 63, 68 | 50, 55 51, 59 | 54, 55 55, 57 |
| Particle Size Distribution by Cascade Impaction Fluticasone Propionate Sum of stages 3-4 (µg per blister) Individual | 19 to 45 | 46, 40 43, 42 39, 41 | 33, 33 31, 35 | 22, 26 24, 27 | 25, 27 27, 28 |
| Particle Size Distribution by Cascade Impaction Fluticasone Propionate Sum of stages TP0 (µg per blister) Individual | 140 to 200 | 173, 170 170, 168 174, 159 | 166, 178 175, 175 | 172, 180 180, 187 | 180, 170 172, 167 |
| Particle Size Distribution by Cascade Impaction Fluticasone Propionate Sum of stages 6, 7 & F (µg per blister) Individual | <2 | 1, 0 1, 0 0, 0 | 0, 0 0, 0 | 0, 0 0, 0 | 0, 0 0, 0 |

TABLE 79

Stability data for DISKUS ® 250/50 µg 60 Dose Product without overwrap

Packed Batch Number: F

Storage condition 25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (µg per blister) Individual | 7 to 13 | 13, 12 13, 12 12, 12 | 11, 12 11, 11 | 11, 11 12, 11 | 10, 12 11, 12 | 9, 10 10, 11 |
| Particle Size Distribution by Cascade Impaction Salmeterol Sum of stages 3-4 (µg per blister) Individual | 3 to 8 | 8, 7 7, 7 7, 7 | 7, 7 7, 7 | 6, 6 7, 6 | 5, 6 6, 6 | 5, 5 5, 6 |
| Particle Size Distribution by Cascade Impaction Salmeterol Sum of stages TP0 (µg per blister) Individual | 28 to 42 | 36, 35 36, 35 36, 33 | 36, 36 36, 36 | 36, 36 35, 39 | 32, 36 37, 36 | 37, 37 36, 37 |
| Particle Size Distribution by Cascade Impaction Salmeterol Sum of stages 6, 7 & F (µg per blister) Individual | NGT 0.5 | 0.1, 0.1 0.1, 0.1 0.1, 0.1 | 0.1, 0.1 0.1, 0.1 | 0.1, 0.1 0.1, 0.1 | 0.0, 0.0 0.0, 0.0 | 0.0, 0.0 0.0, 0.0 |

TABLE 80

Stability data for DISKUS ® 250/50 µg 60 Dose Product without overwrap

Packed Batch Number: F

Storage condition 25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Fluticasone Propionate Sum of stages 1-5 (µg per blister) Individual | 42 to 73 | 76, 70 73, 70 68, 72 | 65, 67 65, 65 | 65, 64 66, 65 | 59, 68 65, 67 | 53, 60 59, 62 |
| Particle Size Distribution by Cascade Impaction Fluticasone Propionate Sum of stages 3-4 (µg per blister) Individual | 19 to 45 | 46, 40 43, 42 39, 41 | 38, 39 37, 39 | 37, 37 40, 35 | 31, 37 35, 37 | 26, 31 30, 33 |
| Particle Size Distribution by Cascade Impaction Fluticasone Propionate | 140 to 200 | 173, 170 170, 168 | 174, 173 172, 171 | 175, 174 168, 188 | 152, 175 178, 173 | 178, 180 176, 179 |

TABLE 80-continued

Stability data for DISKUS ® 250/50 µg 60 Dose Product without overwrap

Packed Batch Number: F

Storage condition
25° C./75% RH
Testing Complete

| Test | End of life Specification | Initial | 2 Weeks | 1 Month | 1.5 Months | 3 Months |
|---|---|---|---|---|---|---|
| Sum of stages TP0 (µg per blister) Individual | | 174, 159 | | | | |
| Particle Size Distribution by Cascade Impaction Fluticasone Propionate Sum of stages 6, 7 & F (µg per blister) Individual | <2 | 1, 0 1, 0 0, 0 | 0, 0 0, 0 | 1, 0 1, 0 | 0, 0 0, 0 | 0, 0 0, 0 |

TABLE 81

Stability data for DISKUS ® 250/50 µg 60 Dose Product without overwrap
Samples previously stored at 25° C./60% RH for 17 months with overwrap Packed Batch Number: F Storage condition
25° C./75% RH
Testing Complete

| Test | End of life Specification | Initial | 2 Weeks | 1 Month | 1.5 Months |
|---|---|---|---|---|---|
| Particle Size Distribution by Cascade Impaction Salmeterol Sum of stages 1-5 (µg per blister) Individual | 7 to 13 | 10, 10 9, 10 | 10, 10 10, 10 | 10, 10 10, 10 | 10, 10 10, 10 |
| Particle Size Distribution by Cascade Impaction Salmeterol Sum of stages 3-4 (µg per blister) Individual | 3 to 8 | 5, 5 5, 5 | 5, 5 5, 5 | 5, 5 5, 5 | 5, 5 5, 5 |
| Particle Size Distribution by Cascade Impaction Salmeterol Sum of stages TP0 (µg per blister) Individual | 28 to 42 | 36, 36 34, 36 | 38, 37 36, 37 | 37, 38 35, 38 | 37, 37 34, 36 |
| Particle Size Distribution by Cascade Impaction Salmeterol Sum of stages 6, 7 & F (µg per blister) Individual | NGT 0.5 | 0.1, 0.0 0.1, 0.1 | 0.1, 0.1 0.1, 0.1 | 0.0, 0.0 0.1, 0.0 | 0.1, 0.1 0.1, 0.1 |

TABLE 82

Stability data for DISKUS ® 250/50 µg 60 Dose Product without overwrap
Samples previously stored at 25° C./60% RH for 17 months with overwrap (cont'd)

Packed Batch Number: F

Storage condition
25° C./75% RH
Testing Complete

| Test | End of life Specification | Initial | 2 Weeks | 1 Month | 1.5 Months |
|---|---|---|---|---|---|
| Particle Size Distribution by Cascade Impaction Fluticasone Propionate Sum of stages 1-5 (µg per blister) Individual | 42 to 73 | 59, 57 53, 59 | 55, 56 55, 57 | 59, 58 58, 59 | 55, 60 57, 61 |
| Particle Size Distribution by Cascade Impaction Fluticasone Propionate Sum of stages 3-4 (µg per blister) Individual | 19 to 45 | 30, 29 27, 31 | 26, 28 27, 28 | 28, 27 29, 29 | 28, 30 28, 30 |
| Particle Size Distribution by Cascade Impaction Fluticasone Propionate Sum of stages TP0 (µg per blister) Individual | 140 to 200 | 177, 180 169, 180 | 185, 183 179, 186 | 183, 187 174, 184 | 180, 182 170, 181 |
| Particle Size Distribution by Cascade Impaction Fluticasone Propionate Sum of stages 6, 7 & F (µg per blister) Individual | <2 | 0, 0 0, 0 | 0, 0 0, 0 | 0, 0 0, 0 | 0, 0 0, 0 |

TABLE 83

Stability data for DISKUS ® 250/50 μg 60 Dose Product with overwrap

Packed Batch Number: G

Storage condition 25° C./60% RH Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (μg per blister) Individual | 7 to 13 | 15, 15 15, 16 | 13, 12 12, 13 | 13, 13 12, 14 | 10, 12 11, 12 |
| Particle Size Distribution by Cascade Impaction Salmeterol Sum of stages 3-4 (μg per blister) Individual | 3 to 8 | 9, 9 9, 9 | 7, 7 7, 8 | 7, 7 6, 7 | 5, 6 6, 6 |
| Particle Size Distribution by Cascade Impaction Salmeterol Sum of stages TP0 (μg per blister) Individual | 28 to 42 | 32, 33 34, 35 | 32, 33 32, 32 | 33, 36 33, 35 | 30, 34 31, 33 |
| Particle Size Distribution by Cascade Impaction Salmeterol Sum of stages 6, 7 & F (μg per blister) Individual | NGT 0.5 | 0.1, 0.1 0.1, 0.2 | 0.1, 0.1 0.1, 0.1 | 0.0, 0.0 0.0, 0.0 | 0.0, 0.0 0.0, 0.0 |

TABLE 84

Stability data for DISKUS ® 250/50 μg 60 Dose Product with overwrap

Packed Batch Number: G

Storage condition 25° C./60% RH Testing Complete

| Test | End of life Specification | Initial | 9 months | 12 months | 18 months |
|---|---|---|---|---|---|
| Particle Size Distribution by Cascade Impaction Salmeterol Sum of stages 1-5 (μg per blister) Individual | 7 to 13 | 15, 15 15, 16 | 12, 12 11, 11 | 13, 14 13, 14 | 11, 11 11, 11 |
| Particle Size Distribution by Cascade Impaction Salmeterol Sum of stages 3-4 (μg per blister) Individual | 3 to 8 | 9, 9 9, 9 | 6, 7 6, 6 | 7, 7 7, 7 | 6, 6 6, 6 |
| Particle Size Distribution by Cascade Impaction Salmeterol Sum of stages TP0 (μg per blister) Individual | 28 to 42 | 32, 33 34, 35 | 33, 32 32, 33 | 33, 34 34, 33 | 33, 33 32, 34 |
| Particle Size Distribution by Cascade Impaction Salmeterol Sum of stages 6, 7 & F (μg per blister) Individual | NGT 0.5 | 0.1, 0.1 0.1, 0.2 | 0.0, 0.0 0.0, 0.0 | 0.1, 0.1 0.1, 0.1 | 0.1, 0.1 0.1, 0.1 |

TABLE 85

Stability data for DISKUS ® 250/50 μg 60 Dose Product with overwrap

Packed Batch Number: G

Storage condition 25° C./60% RH Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (μg per blister) Individual | 42 to 73 | 87, 86 88, 92 | 72, 68 70, 74 | 77, 74 70, 78 | 57, 69 66, 72 |
| Particle Size Distribution by Cascade | 19 to 45 | 52, 48 | 42, 38 | 43, 40 | 29, 35 |

TABLE 85-continued

Stability data for DISKUS ® 250/50 μg 60 Dose Product with overwrap

Packed Batch Number: G

Storage condition 25° C./60% RH
Testing Complete

| Test | End of life Specification | Initial | 1 Month | 3 Months | 6 Months |
|---|---|---|---|---|---|
| Impaction Fluticasone Propionate Sum of stages 3-4 (μg per blister) Individual | | 53, 54 | 41, 44 | 37, 42 | 36, 37 |
| Particle Size Distribution by Cascade Impaction Fluticasone Propionate Sum of stages TP0 (μg per blister) Individual | 140 to 200 | 152, 157 159, 165 | 153, 158 150, 150 | 160, 174 157, 168 | 150, 166 150, 161 |
| Particle Size Distribution by Cascade Impaction Fluticasone Propionate Sum of stages 6, 7 & F (μg per blister) Individual | <2 | 1, 1 1, 1 | 0, 0 0, 0 | 0, 0 0, 0 | 0, 0 0, 0 |

TABLE 86

Stability data for DISKUS ® 250/50 μg 60 Dose Product with overwrap

Packed Batch Number: G

Storage condition 25° C./60% RH
Testing Complete

| Test | End of life Specification | Initial | 9 months | 12 months | 18 months |
|---|---|---|---|---|---|
| Particle Size Distribution by Cascade Impaction Fluticasone Propionate Sum of stages 1-5 (μg per blister) Individual | 42 to 73 | 87, 86 88, 92 | 70, 70 63, 65 | 75, 77 73, 75 | 66, 66 65, 66 |
| Particle Size Distribution by Cascade Impaction Fluticasone Propionate Sum of stages 3-4 (μg per blister) Individual | 19 to 45 | 52, 48 53, 54 | 37, 38 32, 33 | 39, 42 38, 40 | 33, 34 33, 33 |
| Particle Size Distribution by Cascade Impaction Fluticasone Propionate Sum of stages TP0 (μg per blister) Individual | 140 to 200 | 152, 157 159, 165 | 157, 152 155, 159 | 160, 163 165, 162 | 161, 164 158, 168 |
| Particle Size Distribution by Cascade Impaction Fluticasone Propionate Sum of stages 6, 7 & F (μg per blister) Individual | <2 | 1, 1 1, 1 | 0, 0 0, 0 | 0, 0 0, 0 | 0, 0 0, 0 |

TABLE 87

Stability data for DISKUS ® 250/50 μg 60 Dose Product without overwrap

Packed Batch Number: G

Storage condition 25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (μg per blister) Individual | 7 to 13 | 15, 15 15, 16 | 13, 14 14, 13 | 12, 13 12, 12 | 14, 12 12, 12 | 13, 11 11, 13 |
| Particle Size Distribution by Cascade Impaction Salmeterol Sum of stages 3-4 (μg per blister) Individual | 3 to 8 | 9, 9 9, 9 | 6, 8 8, 7 | 7, 7 7, 6 | 8, 7 6, 7 | 7, 6 6, 7 |
| Particle Size Distribution by Cascade Impaction Salmeterol Sum of stages TP0 (μg per blister) Individual | 28 to 42 | 32, 33 34, 35 | 32, 33 35, 34 | 32, 33 32, 33 | 34, 32 32, 33 | 32, 31 31, 33 |
| Particle Size Distribution by Cascade | NGT 0.5 | 0.1, 0.1 | 0.1, 0.1 | 0.1, 0.1 | 0.0, 0.0 | 0.0, 0.0 |

TABLE 87-continued

Stability data for DISKUS ® 250/50 µg 60 Dose Product without overwrap

Packed Batch Number: G

Storage condition 25° C./75% RH
Testing Complete

| Test | End of life Specification | Initial | 2 Weeks | 1 Month | 1.5 Months | 3 Months |
|---|---|---|---|---|---|---|
| Impaction Salmeterol Sum of stages 6, 7 & F (µg per blister) Individual | | 0.1, 0.2 | 0.1, 0.1 | 0.1, 0.1 | 0.0, 0.0 | 0.0, 0.0 |

TABLE 88

Stability data for DISKUS ® 250/50 µg 60 Dose Product without overwrap

Packed Batch Number: G

Storage condition 25° C./75% RH
Testing Complete

| Test | End of life Specification | Initial | 2 weeks | 1 Month | 1.5 Months | 3 Months |
|---|---|---|---|---|---|---|
| Particle Size Distribution by Cascade Impaction Fluticasone Propionate Sum of stages 1-5 (µg per blister) Individual | 42 to 73 | 87, 86 88, 92 | 72, 82 81, 76 | 67, 72 70, 68 | 78, 70 68, 72 | 76, 66 66, 73 |
| Particle Size Distribution by Cascade Impaction Fluticasone Propionate Sum of stages 3-4 (µg per blister) Individual | 19 to 45 | 52, 48 53, 54 | 37, 46 45, 41 | 38, 41 40, 37 | 44, 40 35, 38 | 42, 36 33, 40 |
| Particle Size Distribution by Cascade Impaction Fluticasone Propionate Sum of stages TP0 (µg per blister) Individual | 140 to 200 | 152, 157 159, 165 | 155, 156 165, 160 | 155, 157 155, 161 | 163, 152 156, 160 | 156, 149 149, 160 |
| Particle Size Distribution by Cascade Impaction Fluticasone Propionate Sum of stages 6, 7 & F (µg per blister) Individual | <2 | 1, 1 1, 1 | 0, 1 1, 1 | 1, 0 0, 0 | 0, 0 0, 0 | 0, 0 0, 0 |

TABLE 89

Stability data for DISKUS ® 250/50 µg 60 Dose Product without overwrap
Samples previously stored at 25° C./60% RH for 17 months with overwrap Packed Batch Number: G Storage condition 25° C./75% RH
Testing Complete

| Test | End of life Specification | Initial | 2 Weeks | 1 Month | 1.5 Months |
|---|---|---|---|---|---|
| Particle Size Distribution by Cascade Impaction Salmeterol Sum of stages 1-5 (µg per blister) Individual | 7 to 13 | 12, 12 11, 11 | 11, 11 12, 10 | 13, 12 12, 11 | 11, 11 10, 10 |
| Particle Size Distribution by Cascade Impaction Salmeterol Sum of stages 3-4 (µg per blister) Individual | 3 to 8 | 6, 6 5, 5 | 6, 5 6, 5 | 7, 6 6, 6 | 6, 6 4, 5 |
| Particle Size Distribution by Cascade Impaction Salmeterol Sum of stages TP0 (µg per blister) Individual | 28 to 42 | 33, 34 33, 32 | 33, 33 34, 32 | 34, 33 34, 32 | 33, 32 33, 34 |
| Particle Size Distribution by Cascade Impaction Salmeterol Sum of stages 6, 7 & F (µg per blister) Individual | NGT 0.5 | 0.1, 0.1 0.1, 0.1 | 0.1, 0.1 0.1, 0.1 | 0.1, 0.1 0.1, 0.1 | 0.1, 0.1 0.1, 0.1 |

TABLE 90

Stability data for DISKUS ® 250/50 μg 60 Dose Product without overwrap
Samples previously stored at 25° C./60% RH for 17 months with overwrap (cont'd)

Packed Batch Number: G

Storage condition
25° C./75% RH
Testing Complete

| Test | End of life Specification | Initial | 2 weeks | 1 Month | 1.5 Months |
|---|---|---|---|---|---|
| Particle Size Distribution by Cascade Impaction Fluticasone Propionate Sum of stages 1-5 (μg per blister) Individual | 42 to 73 | 71, 69 62, 62 | 65, 63 67, 61 | 73, 71 68, 65 | 66, 62 58, 61 |
| Particle Size Distribution by Cascade Impaction Fluticasone Propionate Sum of stages 3-4 (μg per blister) Individual | 19 to 45 | 35, 33 28, 29 | 33, 30 32, 30 | 39, 37 36, 33 | 36, 32 26, 31 |
| Particle Size Distribution by Cascade Impaction Fluticasone Propionate Sum of stages TP0 (μg per blister) Individual | 140 to 200 | 160, 166 161, 154 | 156, 158 165, 155 | 167, 161 165, 157 | 162, 158 163, 166 |
| Particle Size Distribution by Cascade Impaction Fluticasone Propionate Sum of stages 6, 7 & F (μg per blister) Individual | <2 | 0, 0 0, 0 | 0, 0 0, 0 | 0, 0 0, 0 | 0, 0 0, 0 |

TABLE 91

Stability data for DISKUS ® 250/50 μg 60 Dose Product with overwrap

Packed Batch Number: H

Storage condition
25° C./60% RH
Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (μg per blister) Individual | 7 to 13 | 11, 10 12, 11 | 10, 10 11, 10 | 10, 9 10, 10 | 9, 9 9, 9 |
| Particle Size Distribution by Cascade Impaction Salmeterol Sum of stages 3-4 (μg per blister) Individual | 3 to 8 | 6, 6 7, 6 | 6, 6 6, 6 | 5, 5 5, 5 | 5, 5 5, 5 |
| Particle Size Distribution by Cascade Impaction Salmeterol Sum of stages TP0 (μg per blister) Individual | 28 to 42 | 38, 36 37, 36 | 38, 37 39, 38 | 39, 38 38, 38 | 38, 37 39, 37 |
| Particle Size Distribution by Cascade Impaction Salmeterol Sum of stages 6, 7 & F (μg per blister) Individual | NGT 0.5 | 0.0, 0.1 0.1, 0.1 | 0.1, 0.1 0.1, 0.1 | 0.0, 0.0 0.0, 0.0 | 0.0, 0.0 0.0, 0.0 |

TABLE 92

Stability data for DISKUS ® 250/50 μg 60 Dose Product with overwrap

Packed Batch Number: H

Storage condition
25° C./60% RH
Testing Complete

| Test | End of life Specification | Initial | 9 months | 12 months | 18 months |
|---|---|---|---|---|---|
| Particle Size Distribution by Cascade Impaction Salmeterol Sum of stages 1-5 (μg per blister) Individual | 7 to 13 | 11, 10 12, 11 | 9, 10 10, 10 | 10, 10 10, 10 | 10, 9 9, 9 |
| Particle Size Distribution by Cascade | 3 to 8 | 6, 6 | 5, 5 | 5, 5 | 5, 4 |

TABLE 92-continued

Stability data for DISKUS ® 250/50 μg 60 Dose Product with overwrap

Packed Batch Number: H

Storage condition 25° C./60% RH
Testing Complete

| Test | End of life Specification | Initial | 9 months | 12 months | 18 months |
|---|---|---|---|---|---|
| Impaction Salmeterol Sum of stages 3-4 (μg per blister) Individual | | 7, 6<br>7, 6 | 5, 5<br>5, 5 | 5, 5<br>5, 5 | 4, 5<br>4, 5 |
| Particle Size Distribution by Cascade Impaction Salmeterol Sum of stages TP0 (μg per blister) Individual | 28 to 42 | 38, 36<br>37, 36 | 38, 36<br>35, 35 | 38, 37<br>38, 38 | 39, 37<br>39, 33 |
| Particle Size Distribution by Cascade Impaction Salmeterol Sum of stages 6, 7 & F (μg per blister) Individual | NGT 0.5 | 0.0, 0.1<br>0.1, 0.1 | 0.0, 0.0<br>0.0, 0.0 | 0.1, 0.1<br>0.1, 0.1 | 0.1, 0.0<br>0.1, 0.1 |

TABLE 93

Stability data for DISKUS ® 250/50 μg 60 Dose Product with overwrap

Packed Batch Number: H

Storage condition 25° C./60% RH
Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (μg per blister) Individual | 42 to 73 | 61, 59<br>66, 62 | 57, 56<br>61, 58 | 57, 55<br>59, 57 | 53, 53<br>55, 54 |
| Particle Size Distribution by Cascade Impaction Fluticasone Propionate Sum of stages 3-4 (μg per blister) Individual | 19 to 45 | 35, 34<br>39, 34 | 32, 32<br>34, 32 | 30, 28<br>31, 29 | 29, 28<br>28, 27 |
| Particle Size Distribution by Cascade Impaction Fluticasone Propionate Sum of stages TP0 (μg per blister) Individual | 140 to 200 | 181, 170<br>175, 172 | 182, 180<br>188, 185 | 185, 181<br>181, 181 | 181, 179<br>189, 181 |
| Particle Size Distribution by Cascade Impaction Fluticasone Propionate Sum of stages 6, 7 & F (μg per blister) Individual | <2 | 0, 0<br>1, 0 | 0, 0<br>0, 0 | 0, 0<br>0, 0 | 0, 0<br>0, 0 |

TABLE 94

Stability data for DISKUS ® 250/50 μg 60 Dose Product with overwrap

Packed Batch Number: H

Storage condition 25° C./60% RH
Testing Complete

| Test | End of life Specification | Initial | 9 months | 12 months | 18 months |
|---|---|---|---|---|---|
| Particle Size Distribution by Cascade Impaction Fluticasone Propionate Sum of stages 1-5 (μg per blister) Individual | 42 to 73 | 61, 59<br>66, 62 | 55, 56<br>56, 58 | 60, 61<br>60, 59 | 55, 51<br>50, 51 |
| Particle Size Distribution by Cascade Impaction Fluticasone Propionate Sum of stages 3-4 (μg per blister) Individual | 19 to 45 | 35, 34<br>39, 34 | 27, 28<br>29, 30 | 31, 32<br>31, 31 | 27, 26<br>24, 27 |
| Particle Size Distribution by Cascade Impaction Fluticasone Propionate Sum of stages TP0 (μg per blister) Individual | 140 to 200 | 181, 170<br>175, 172 | 182, 177<br>172, 171 | 188, 182<br>183, 183 | 188, 183<br>193, 163 |
| Particle Size Distribution by Cascade | <2 | 0, 0 | 0, 0 | 0, 0 | 0, 0 |

TABLE 94-continued

Stability data for DISKUS ® 250/50 μg 60 Dose Product with overwrap

Packed Batch Number: H

Storage condition 25° C./60% RH
Testing Complete

| Test | End of life Specification | Initial | 9 months | 12 months | 18 months |
|---|---|---|---|---|---|
| Impaction Fluticasone Propionate Sum of stages 6, 7 & F (μg per blister) Individual | | 1, 0 | 0, 0 | 0, 0 | 0, 0 |

TABLE 95

Stability data for DISKUS ® 250/50 μg 60 Dose Product without overwrap

Packed Batch Number: H

Storage condition 25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (μg per blister) Individual | 7 to 13 | 11, 10 12, 11 | 10, 10 10, 10 | 10, 11 11, 10 | 9, 9 10, 10 | 9, 9 10, 9 |
| Particle Size Distribution by Cascade Impaction Salmeterol Sum of stages 3-4 (μg per blister) Individual | 3 to 8 | 6, 6 7, 6 | 6, 6 6, 6 | 5, 6 6, 5 | 5, 5 5, 5 | 4, 5 5, 4 |
| Particle Size Distribution by Cascade Impaction Salmeterol Sum of stages TP0 (μg per blister) Individual | 28 to 42 | 38, 36 37, 36 | 37, 35 36, 37 | 36, 37 38, 37 | 36, 37 38, 38 | 39, 38 39, 37 |
| Particle Size Distribution by Cascade Impaction Salmeterol Sum of stages 6, 7 & F (μg per blister) Individual | NGT 0.5 | 0.0, 0.1 0.1, 0.1 | 0.1, 0.1 0.1, 0.1 | 0.0, 0.0 0.0, 0.0 | 0.0, 0.0 0.0, 0.0 | 0.0, 0.0 0.0, 0.0 |

TABLE 96

Stability data for DISKUS ® 250/50 μg 60 Dose Product without overwrap

Packed Batch Number: H

Storage condition 25° C./75% RH
Testing Complete

| Test | End of life Specification | Initial | 2 weeks | 1 Month | 1.5 Months | 3 Months |
|---|---|---|---|---|---|---|
| Particle Size Distribution by Cascade Impaction Fluticasone Propionate Sum of stages 1-5 (μg per blister) Individual | 42 to 73 | 61, 59 66, 62 | 59, 58 59, 58 | 61, 61 61, 59 | 54, 54 57, 55 | 54, 54 59, 53 |
| Particle Size Distribution by Cascade Impaction Fluticasone Propionate Sum of stages 3-4 (μg per blister) Individual | 19 to 45 | 35, 34 39, 34 | 33, 34 36, 34 | 32, 33 32, 32 | 28, 28 30, 29 | 26, 27 31, 26 |
| Particle Size Distribution by Cascade Impaction Fluticasone Propionate Sum of stages TP0 (μg per blister) Individual | 140 to 200 | 181, 170 175, 172 | 180, 170 172, 177 | 169, 175 180, 175 | 175, 179 183, 182 | 189, 185 189, 181 |
| Particle Size Distribution by Cascade Impaction Fluticasone Propionate Sum of stages 6, 7 & F (μg per blister) Individual | <2 | 0, 0 1, 0 | 0, 1 1, 0 | 0, 0 0, 0 | 0, 0 0, 0 | 0, 0 0, 0 |

TABLE 97

Stability data for DISKUS ® 250/50 μg 60 Dose Product without overwrap
Samples previously stored at 25° C./60% RH for 17 months with overwrap Packed Batch Number: H Storage condition 25° C./75% RH Testing Complete

| Test | End of life Specification | Initial | 2 Weeks | 1 Month | 1.5 Months |
|---|---|---|---|---|---|
| Particle Size Distribution by Cascade Impaction Salmeterol Sum of stages 1-5 (μg per blister) Individual | 7 to 13 | 9, 9 10, 9 | 9, 9 9, 9 | 10, 10 9, 10 | 9, 10 9, 9 |
| Particle Size Distribution by Cascade Impaction Salmeterol Sum of stages 3-4 (μg per blister) Individual | 3 to 8 | 5, 5 5, 4 | 5, 4 4, 5 | 5, 5 5, 5 | 4, 5 4, 5 |
| Particle Size Distribution by Cascade Impaction Salmeterol Sum of stages TP0 (μg per blister) Individual | 28 to 42 | 37, 37 36, 37 | 38, 38 38, 37 | 36, 36 37, 36 | 37, 38 35, 36 |
| Particle Size Distribution by Cascade Impaction Salmeterol Sum of stages 6, 7 & F (μg per blister) Individual | NGT 0.5 | 0.1, 0.1 0.1, 0.1 | 0.1, 0.1 0.1, 0.1 | 0.1, 0.1 0.0, 0.1 | 0.1, 0.0 0.2, 0.0 |

TABLE 98

Stability data for DISKUS ® 250/50 μg 60 Dose Product without overwrap
Samples previously stored at 25° C./60% RH for 17 months with overwrap (cont'd)

Packed Batch Number: H

Storage condition 25° C./75% RH Testing Complete

| Test | End of life Specification | Initial | 2 weeks | 1 Month | 1.5 Months |
|---|---|---|---|---|---|
| Particle Size Distribution by Cascade Impaction Fluticasone Propionate Sum of stages 1-5 (μg per blister) Individual | 42 to 73 | 55, 54 57, 55 | 54, 53 51, 53 | 56, 55 55, 57 | 51, 56 51, 55 |
| Particle Size Distribution by Cascade Impaction Fluticasone Propionate Sum of stages 3-4 (μg per blister) Individual | 19 to 45 | 27, 27 28, 26 | 27, 26 24, 27 | 29, 28 27, 28 | 26, 28 23, 27 |
| Particle Size Distribution by Cascade Impaction Fluticasone Propionate Sum of stages TP0 (μg per blister) Individual | 140 to 200 | 179, 184 178, 183 | 184, 184 188, 183 | 177, 179 183, 178 | 178, 184 175, 191 |
| Particle Size Distribution by Cascade Impaction Fluticasone Propionate Sum of stages 6, 7 & F (μg per blister) Individual | <2 | 0, 0 0, 0 | 0, 0 0, 0 | 0, 0 0, 0 | 0, 0 1, 0 |

TABLE 99

Stability data for DISKUS ® 500/50 μg 60 Dose Product with overwrap

Packed Batch Number: I

Storage condition 25° C./60% RH Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (μg per blister) Individual | 7 to 13 | 11, 12 12, 11 | 11, 11 11, 10 | 10, 10 10, 10 | 10, 10 9, 10 |
| Particle Size Distribution by Cascade Impaction Salmeterol Sum of stages 3-4 (μg per blister) Individual | 4 to 8 | 7, 7 7, 7 | 6, 6 6, 6 | 5, 5 6, 6 | 5, 5 5, 6 |

TABLE 99-continued

Stability data for DISKUS ® 500/50 µg 60 Dose Product with overwrap

Packed Batch Number: I

Storage condition 25° C./60% RH
Testing Complete

| Test | End of life Specification | Initial | 1 Month | 3 Months | 6 Months |
| --- | --- | --- | --- | --- | --- |
| Particle Size Distribution by Cascade Impaction Salmeterol Sum of stages TP0 (µg per blister) Individual | 28 to 42 | 34, 35 35, 33 | 31, 36 33, 34 | 36, 35 36, 36 | 33, 36 33, 33 |
| Particle Size Distribution by Cascade Impaction Salmeterol Sum of stages 6, 7 & F (µg per blister) Individual | NGT 0.5 | 0.1, 0.1 0.1, 0.1 | 0.0, 0.0 0.0, 0.0 | 0.0, 0.0 0.0, 0.0 | 0.0, 0.0 0.0, 0.0 |

TABLE 100

Stability data for DISKUS ® 500/50 µg 60 Dose Product with overwrap

Packed Batch Number: I

Storage condition 25° C./60% RH
Testing Complete

| Test | End of life Specification | Initial | 9 Months | 12 Months | 18 Months |
| --- | --- | --- | --- | --- | --- |
| Particle Size Distribution by Cascade Impaction Salmeterol Sum of stages 1-5 (µg per blister) Individual | 7 to 13 | 11, 12 12, 11 | 10, 10 10, 10 | 10, 9 8, 9 | 9, 9 9, 9 |
| Particle Size Distribution by Cascade Impaction Salmeterol Sum of stages 3-4 (µg per blister) Individual | 4 to 8 | 7, 7 7, 7 | 5, 5 5, 6 | 5, 4 4, 4 | 5, 4 5, 5 |
| Particle Size Distribution by Cascade Impaction Salmeterol Sum of stages TP0 (µg per blister) Individual | 28 to 42 | 34, 35 35, 33 | 35, 34 37, 37 | 37, 34 32, 36 | 36, 34 34, 35 |
| Particle Size Distribution by Cascade Impaction Salmeterol Sum of stages 6, 7 & F (µg per blister) Individual | NGT 0.5 | 0.1, 0.1 0.1, 0.1 | 0.1, 0.0 0.0, 0.0 | 0.0, 0.0 0.0, 0.0 | 0.0, 0.1 0.0, 0.0 |

TABLE 101

Stability data for DISKUS ® 500/50 µg 60 Dose Product with overwrap

Packed Batch Number: I

Storage condition 25° C./60% RH
Testing Complete

| Test | End of life Specification | Initial | 1 Month | 3 Months | 6 Months |
| --- | --- | --- | --- | --- | --- |
| Particle Size Distribution by Cascade Impaction Fluticasone Propionate Sum of stages 1-5 (µg per blister) Individual | 96 to 150 | 127, 130 129, 125 | 119, 122 121, 112 | 112, 111 117, 116 | 110, 114 105, 116 |
| Particle Size Distribution by Cascade Impaction Fluticasone Propionate Sum of stages 3-4 (µg per blister) Individual | 43 to 92 | 75, 76 77, 75 | 70, 71 71, 62 | 60, 59 64, 64 | 60, 61 55, 63 |
| Particle Size Distribution by Cascade Impaction Fluticasone Propionate Sum of stages TP0 (µg per blister) Individual | 290 to 400 | 325, 339 337, 322 | 301, 354 326, 333 | 349, 346 350, 349 | 326, 346 325, 319 |
| Particle Size Distribution by Cascade Impaction Fluticasone Propionate Sum of stages 6, 7 & F (µg per blister) Individual | NGT 2 | 1, 1 1, 1 | 1, 1 1, 1 | 1, 0 1, 1 | 1, 1 1, 1 |

TABLE 102

Stability data for DISKUS ® 500/50 µg 60 Dose Product with overwrap

Packed Batch Number: I

Storage condition
25° C./60% RH
Testing Complete

| Test | End of life Specification | Initial | 9 Months | 12 Months | 18 Months |
|---|---|---|---|---|---|
| Particle Size Distribution by Cascade Impaction Fluticasone Propionate Sum of stages 1-5 (µg per blister) Individual | 96 to 150 | 127, 130 129, 125 | 110, 110 109, 114 | 110, 96 91, 99 | 100, 95 106, 104 |
| Particle Size Distribution by Cascade Impaction Fluticasone Propionate Sum of stages 3-4 (µg per blister) Individual | 43 to 92 | 75, 76 77, 75 | 59, 60 59, 62 | 60, 50 48, 48 | 51, 50 57, 56 |
| Particle Size Distribution by Cascade Impaction Fluticasone Propionate Sum of stages TP0 (µg per blister) Individual | 290 to 400 | 325, 339 337, 322 | 342, 332 364, 364 | 360, 337 313, 348 | 351, 335 342, 349 |
| Particle Size Distribution by Cascade Impaction Fluticasone Propionate Sum of stages 6, 7 & F (µg per blister) Individual | NGT 2 | 1, 1 1, 1 | 1, 1 1, 1 | 0, 0 0, 0 | 1, 1 1, 1 |

TABLE 103

Stability data for DISKUS ® 500/50 µg 60 Dose Product without overwrap

Packed Batch Number: I

Storage condition
25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (µg per blister) Individual | 7 to 13 | 11, 12 12, 11 | 11, 11 12, 11 | 10, 11 11, 11 | 10, 11 11, 11 | 10, 10 10, 9 |
| Particle Size Distribution by Cascade Impaction Salmeterol Sum of stages 3-4 (µg per blister) Individual | 4 to 8 | 7, 7 7, 7 | 6, 6 7, 6 | 6, 7 6, 6 | 6, 6 6, 6 | 6, 6 5, 5 |
| Particle Size Distribution by Cascade Impaction Salmeterol Sum of stages TP0 (µg per blister) Individual | 28 to 42 | 34, 35 35, 33 | 37, 37 37, 35 | 35, 36 36, 36 | 34, 34 35, 35 | 36, 34 35, 33 |
| Particle Size Distribution by Cascade Impaction Salmeterol Sum of stages 6, 7 & F (µg per blister) Individual | NGT 0.5 | 0.1, 0.1 0.1, 0.1 | 0.1, 0.1 0.1, 0.1 | 0.0, 0.0 0.0, 0.0 | 0.0, 0.0 0.0, 0.0 | 0.0, 0.0 0.0, 0.0 |

TABLE 104

Stability data for DISKUS ® 500/50 µg 60 Dose Product without overwrap

Packed Batch Number: I

Storage condition
25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Fluticasone Propionate Sum of stages 1-5 (µg per blister) Individual | 96 to 150 | 127, 130 129, 125 | 127, 125 131, 117 | 116, 128 119, 127 | 114, 124 125, 118 | 118, 113 113, 105 |
| Particle Size Distribution by Cascade Impaction Fluticasone Propionate Sum of stages 3-4 (µg per blister) Individual | 43 to 92 | 75, 76 77, 75 | 70, 68 73, 66 | 66, 73 69, 72 | 67, 72 71, 67 | 65, 64 62, 56 |
| Particle Size Distribution by Cascade | 290 to 400 | 325, 339 | 355, 362 | 336, 352 | 326, 324 | 345, 332 |

TABLE 104-continued

Stability data for DISKUS ® 500/50 μg 60 Dose Product without overwrap

Packed Batch Number: I

Storage condition 25° C./75% RH
Testing Complete

| Test | End of life Specification | Initial | 2 Weeks | 1 Month | 1.5 Months | 3 Months |
|---|---|---|---|---|---|---|
| Impaction Fluticasone Propionate Sum of stages TP0 (μg per blister) Individual | | 337, 322 | 358, 341 | 346, 348 | 337, 345 | 344, 322 |
| Particle Size Distribution by Cascade Impaction Fluticasone Propionate Sum of stages 6, 7 & F (μg per blister) Individual | NGT 2 | 1, 1 1, 1 | 1, 1 1, 1 | 1, 1 1, 1 | 1, 1 1, 1 | 1, 1 1, 0 |

TABLE 105

Stability data for DISKUS ® 500/50 μg 60 Dose Product without overwrap
Samples previously stored at 25° C./60% RH with overwrap for 17 months Packed Batch Number: I Storage condition 25° C./75% RH
Testing Complete

| Test | End of life Specification | Initial | 2 Weeks | 1 Month | 1.5 Months |
|---|---|---|---|---|---|
| Particle Size Distribution by Cascade Impaction Salmeterol Sum of stages 1-5 (μg per blister) Individual | 7 to 13 | 10, 9 9, 9 | 9, 9 10, 10 | 10, 10 10, 9 | 9, 9 9, 10 |
| Particle Size Distribution by Cascade Impaction Salmeterol Sum of stages 3-4 (μg per blister) Individual | 4 to 8 | 6, 4 5, 5 | 5, 5 5, 5 | 5, 5 5, 5 | 4, 5 5, 5 |
| Particle Size Distribution by Cascade Impaction Salmeterol Sum of stages TP0 (μg per blister) Individual | 28 to 42 | 35, 38 36, 36 | 37, 36 37, 38 | 36, 36 35, 34 | 35, 34 35, 36 |
| Particle Size Distribution by Cascade Impaction Salmeterol Sum of stages 6, 7 & F (μg per blister) Individual | NGT 0.5 | 0.0, 0.0 0.0, 0.0 | 0.1, 0.0 0.1, 0.1 | 0.1, 0.0 0.0, 0.0 | 0.0, 0.0 0.0, 0.0 |

TABLE 106

Stability data for DISKUS ® 500/50 μg 60 Dose Product without overwrap
Samples previously stored at 25° C./60% RH with overwrap for 17 months (cont'd)

Packed Batch Number: I

Storage condition 25° C./75% RH
Testing Complete

| Test | End of life Specification | Initial | 2 Weeks | 1 Month | 1.5 Months |
|---|---|---|---|---|---|
| Particle Size Distribution by Cascade Impaction Fluticasone Propionate Sum of stages 1-5 (μg per blister) Individual | 96 to 150 | 107, 101 103, 105 | 101, 101 107, 112 | 115, 108 108, 104 | 105, 102 101, 108 |
| Particle Size Distribution by Cascade Impaction Fluticasone Propionate Sum of stages 3-4 (μg per blister) Individual | 43 to 92 | 70, 50 51, 53 | 54, 51 55, 59 | 62, 56 56, 55 | 50, 55 52, 57 |
| Particle Size Distribution by Cascade Impaction Fluticasone Propionate Sum of stages TP0 (μg per blister) Individual | 290 to 400 | 344, 375 351, 359 | 361, 355 369, 375 | 359, 353 347, 341 | 344, 334 344, 353 |
| Particle Size Distribution by Cascade | NGT 2 | 1, 0 | 1, 1 | 1, 1 | 1, 1 |

TABLE 106-continued

Stability data for DISKUS ® 500/50 µg 60 Dose Product without overwrap
Samples previously stored at 25° C./60% RH with overwrap for 17 months (cont'd)

| Packed Batch Number: I | | | | Storage condition 25° C./75% RH Testing Complete | |
|---|---|---|---|---|---|
| | End of life | | Storage Time | | |
| Test | Specification | Initial | 2 Weeks | 1 Month | 1.5 Months |
| Impaction Fluticasone Propionate Sum of stages 6, 7 & F (µg per blister) Individual | | 1, 1 | 1, 1 | 1, 1 | 1, 1 |

TABLE 107

Stability data for DISKUS ® 500/50 µg 60 Dose Product with overwrap

| Packed Batch Number: J | | | | Storage condition 25° C./60% RH Testing Complete | |
|---|---|---|---|---|---|
| | End of life | | Storage Time | | |
| Test | Specification | Initial | 1 Month | 3 Months | 6 Months |
| Particle Size Distribution by Cascade Impaction Salmeterol Sum of stages 1-5 (µg per blister) Individual | 7 to 13 | 11, 11 12, 11 | 10, 11 10, 10 | 10, 11 11, 10 | 9, 10 10, 10 |
| Particle Size Distribution by Cascade Impaction Salmeterol Sum of stages 3-4 (µg per blister) Individual | 4 to 8 | 7, 7 7, 6 | 6, 6 6, 6 | 5, 6 6, 5 | 5, 5 5, 5 |
| Particle Size Distribution by Cascade Impaction Salmeterol Sum of stages TP0 (µg per blister) Individual | 28 to 42 | 35, 36 35, 32 | 35, 34 35, 34 | 36, 36 36, 36 | 36, 37 36, 35 |
| Particle Size Distribution by Cascade Impaction Salmeterol Sum of stages 6, 7 & F (µg per blister) Individual | NGT 0.5 | 0.1, 0.1 0.1, 0.0 | 0.0, 0.0 0.0, 0.0 | 0.0, 0.0 0.0, 0.0 | 0.0, 0.0 0.0, 0.0 |

TABLE 108

Stability data for DISKUS ® 500/50 µg 60 Dose Product with overwrap

| Packed Batch Number: J | | | | Storage condition 25° C./60% RH Testing Complete | |
|---|---|---|---|---|---|
| | End of life | | Storage Time | | |
| Test | Specification | Initial | 9 Months | 12 Months | 18 Months |
| Particle Size Distribution by Cascade Impaction Salmeterol Sum of stages 1-5 (µg per blister) Individual | 7 to 13 | 11, 11 12, 11 | 10, 10 9, 9 | 10, 10 10, 10 | 10, 10 11, 9 |
| Particle Size Distribution by Cascade Impaction Salmeterol Sum of stages 3-4 (µg per blister) Individual | 4 to 8 | 7, 7 7, 6 | 5, 5 5, 5 | 6, 5 6, 5 | 6, 5 6, 5 |
| Particle Size Distribution by Cascade Impaction Salmeterol Sum of stages TP0 (µg per blister) Individual | 28 to 42 | 35, 36 35, 32 | 35, 33 36, 35 | 38, 37 37, 37 | 35, 35 36, 34 |
| Particle Size Distribution by Cascade Impaction Salmeterol Sum of stages 6, 7 & F (µg per blister) Individual | NGT 0.5 | 0.1, 0.1 0.1, 0.0 | 0.0, 0.0 0.0, 0.0 | 0.0, 0.0 0.0, 0.0 | 0.1, 0.1 0.1, 0.0 |

TABLE 109

Stability data for DISKUS ® 500/50 µg 60 Dose Product with overwrap

Packed Batch Number: J

Storage condition
25° C./60% RH
Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (µg per blister) Individual | 96 to 150 | 125, 124 127, 116 | 114, 118 114, 113 | 113, 124 119, 115 | 105, 108 110, 109 |
| Particle Size Distribution by Cascade Impaction Fluticasone Propionate Sum of stages 3-4 (µg per blister) Individual | 43 to 92 | 75, 77 77, 70 | 65, 70 65, 67 | 61, 70 65, 60 | 54, 56 58, 58 |
| Particle Size Distribution by Cascade Impaction Fluticasone Propionate Sum of stages TP0 (µg per blister) Individual | 290 to 400 | 336, 344 344, 309 | 338, 329 340, 325 | 354, 350 359, 358 | 363, 369 352, 341 |
| Particle Size Distribution by Cascade Impaction Fluticasone Propionate Sum of stages 6, 7 & F (µg per blister) Individual | NGT 2 | 1, 1 1, 1 | 1, 1 1, 1 | 1, 1 1, 1 | 1, 0 0, 1 |

TABLE 110

Stability data for DISKUS ® 500/50 µg 60 Dose Product with overwrap

Packed Batch Number: J

Storage condition
25° C./60% RH
Testing Complete

| Test | End of life Specification | Initial | 9 months | 12 months | 18 months |
|---|---|---|---|---|---|
| Particle Size Distribution by Cascade Impaction Fluticasone Propionate Sum of stages 1-5 (µg per blister) Individual | 96 to 150 | 125, 124 127, 116 | 111, 108 103, 106 | 113, 113 115, 114 | 113, 108 117, 105 |
| Particle Size Distribution by Cascade Impaction Fluticasone Propionate Sum of stages 3-4 (µg per blister) Individual | 43 to 92 | 75, 77 77, 70 | 59, 60 55, 57 | 61, 61 62, 59 | 64, 58 64, 56 |
| Particle Size Distribution by Cascade Impaction Fluticasone Propionate Sum of stages TP0 (µg per blister) Individual | 290 to 400 | 336, 344 344, 309 | 343, 330 353, 342 | 363, 358 361, 367 | 350, 349 355, 344 |
| Particle Size Distribution by Cascade Impaction Fluticasone Propionate Sum of stages 6, 7 & F (µg per blister) Individual | NGT 2 | 1, 1 1, 1 | 1, 1 1, 1 | 1, 1 1, 1 | 1, 1 1, 1 |

TABLE 111

Stability data for DISKUS ® 500/50 µg 60 Dose Product without overwrap

Packed Batch Number: J

Storage condition
25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (µg per blister) Individual | 7 to 13 | 11, 11 12, 11 | 11, 11 11, 11 | 11, 11 11, 11 | 11, 11 11, 10 | 9, 10 10, 11 |
| Particle Size Distribution by Cascade Impaction Salmeterol Sum of stages 3-4 (µg per blister) Individual | 4 to 8 | 7, 7 7, 6 | 6, 6 6, 6 | 6, 7 6, 6 | 7, 7 7, 6 | 5, 6 5, 6 |
| Particle Size Distribution by Cascade | 28 to 42 | 35, 36 | 35, 36 | 34, 36 | 34, 34 | 35, 36 |

TABLE 111-continued

Stability data for DISKUS ® 500/50 µg 60 Dose Product without overwrap

Packed Batch Number: J

Storage condition
25° C./75% RH
Testing Complete

| Test | End of life Specification | Initial | 2 Weeks | 1 Month | 1.5 Months | 3 Months |
|---|---|---|---|---|---|---|
| Impaction Salmeterol Sum of stages TP0 (µg per blister) Individual | | 35, 32 | 35, 35 | 36, 34 | 32, 34 | 35, 37 |
| Particle Size Distribution by Cascade Impaction Salmeterol Sum of stages 6, 7 & F (µg per blister) Individual | NGT 0.5 | 0.1, 0.1 0.1, 0.0 | 0.1, 0.1 0.1, 0.1 | 0.0, 0.0 0.0, 0.0 | 0.0, 0.0 0.0, 0.0 | 0.0, 0.0 0.0, 0.0 |

TABLE 112

Stability data for DISKUS ® 500/50 µg 60 Dose Product without overwrap

Packed Batch Number: J

Storage condition
25° C./75% RH
Testing Complete

| Test | End of life Specification | Initial | 2 Weeks | 1 Month | 1.5 Months | 3 Months |
|---|---|---|---|---|---|---|
| Particle Size Distribution by Cascade Impaction Fluticasone Propionate Sum of stages 1-5 (µg per blister) Individual | 96 to 150 | 125, 124 127, 116 | 121, 121 120, 120 | 118, 123 122, 118 | 124, 127 123, 115 | 103, 116 108, 117 |
| Particle Size Distribution by Cascade Impaction Fluticasone Propionate Sum of stages 3-4 (µg per blister) Individual | 43 to 92 | 75, 77 77, 70 | 68, 67 69, 66 | 71, 73 71, 70 | 72, 75 73, 64 | 54, 66 60, 66 |
| Particle Size Distribution by Cascade Impaction Fluticasone Propionate Sum of stages TP0 (µg per blister) Individual | 290 to 400 | 336, 344 344, 309 | 339, 348 337, 343 | 325, 345 346, 331 | 334, 331 314, 332 | 341, 353 341, 361 |
| Particle Size Distribution by Cascade Impaction Fluticasone Propionate Sum of stages 6, 7 & F (µg per blister) Individual | NGT 2 | 1, 1 1, 1 | 1, 1 1, 1 | 1, 1 1, 1 | 1, 1 1, 1 | 1, 1 1, 1 |

TABLE 113

Stability data for DISKUS ® 500/50 µg 60 Dose Product without overwrap
Samples previously stored at 25° C./60% RH with overwrap for 17 months Packed Batch Number: J Storage condition
25° C./75% RH
Testing Complete

| Test | End of life Specification | Initial | 2 Weeks | 1 Month | 1.5 Months |
|---|---|---|---|---|---|
| Particle Size Distribution by Cascade Impaction Salmeterol Sum of stages 1-5 (µg per blister) Individual | 7 to 13 | 9, 10 10, 10 | 10, 10 10, 10 | 10, 10 9, 10 | 10, 11 10, 10 |
| Particle Size Distribution by Cascade Impaction Salmeterol Sum of stages 3-4 (µg per blister) Individual | 4 to 8 | 4, 6 5, 5 | 5, 5 5, 5 | 5, 6 5, 5 | 6, 6 5, 6 |
| Particle Size Distribution by Cascade Impaction Salmeterol Sum of stages TP0 (µg per blister) Individual | 28 to 42 | 36, 36 35, 36 | 36, 35 37, 35 | 35, 35 34, 36 | 38, 37 34, 35 |
| Particle Size Distribution by Cascade Impaction Salmeterol Sum of stages 6, 7 & F (µg per blister) Individual | NGT 0.5 | 0.0, 0.1 0.1, 0.1 | 0.1, 0.1 0.0, 0.1 | 0.0, 0.1 0.0, 0.1 | 0.1, 0.1 0.0, 0.1 |

TABLE 114

Stability data for DISKUS ® 500/50 μg 60 Dose Product without overwrap
Samples previously stored at 25° C./60% RH with overwrap for 17 months (cont'd)

Packed Batch Number: J

Storage condition 25° C./75% RH
Testing Complete

| Test | End of life Specification | Initial | 2 Weeks | 1 Month | 1.5 Months |
|---|---|---|---|---|---|
| Particle Size Distribution by Cascade Impaction Fluticasone Propionate Sum of stages 1-5 (μg per blister) Individual | 96 to 150 | 100, 115 108, 115 | 114, 105 115, 107 | 107, 114 99, 112 | 108, 117 116, 114 |
| Particle Size Distribution by Cascade Impaction Fluticasone Propionate Sum of stages 3-4 (μg per blister) Individual | 43 to 92 | 49, 61 57, 59 | 58, 53 60, 56 | 57, 63 52, 61 | 61, 63 60, 64 |
| Particle Size Distribution by Cascade Impaction Fluticasone Propionate Sum of stages TP0 (μg per blister) Individual | 290 to 400 | 346, 359 341, 360 | 355, 341 366, 348 | 344, 348 338, 357 | 367, 365 340, 353 |
| Particle Size Distribution by Cascade Impaction Fluticasone Propionate Sum of stages 6, 7 & F (μg per blister) Individual | NGT 2 | 0, 1 1, 1 | 1, 1 1, 1 | 1, 1 1, 1 | 1, 1 1, 1 |

TABLE 115

Stability data for DISKUS ® 500/50 μg 60 Dose Product with overwrap

Packed Batch Number: K

Storage condition 25° C./60% RH
Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (μg per blister) Individual | 7 to 13 | 11, 12 12, 12 | 11, 11 11, 11 | 9, 11 10, 10 | 10 11 11, 9 |
| Particle Size Distribution by Cascade Impaction Salmeterol Sum of stages 3-4 (μg per blister) Individual | 4 to 8 | 7, 7 8, 7 | 6, 6 6, 6 | 5, 6 5, 6 | 6, 6 6, 5 |
| Particle Size Distribution by Cascade Impaction Salmeterol Sum of stages TP0 (μg per blister) Individual | 28 to 42 | 36, 37 37, 39 | 35, 37 36, 36 | 34, 36 35, 38 | 36, 37 37, 34 |
| Particle Size Distribution by Cascade Impaction Salmeterol Sum of stages 6, 7 & F (μg per blister) Individual | NGT 0.5 | 0.1, 0.1 0.1, 0.1 | 0.0, 0.0 0.0, 0.0 | 0.0, 0.0 0.0, 0.0 | 0.0, 0.0 0.0, 0.0 |

TABLE 116

Stability data for DISKUS ® 500/50 μg 60 Dose Product with overwrap

Packed Batch Number: K

Storage condition 25° C./60% RH
Testing Complete

| Test | End of life Specification | Initial | 9 Months | 12 Months | 18 Months |
|---|---|---|---|---|---|
| Particle Size Distribution by Cascade Impaction Salmeterol Sum of stages 1-5 (μg per blister) Individual | 7 to 13 | 11, 12 12, 12 | 10, 10 10, 9 | 10, 8 10, 9 | 9, 9 10, 9 |
| Particle Size Distribution by Cascade | 4 to 8 | 7, 7 | 6, 5 | 5, 4 | 5, 5 |

TABLE 116-continued

Stability data for DISKUS ® 500/50 μg 60 Dose Product with overwrap

Packed Batch Number: K

Storage condition 25° C./60% RH
Testing Complete

| Test | End of life Specification | Initial | 9 Months | 12 Months | 18 Months |
|---|---|---|---|---|---|
| Impaction Salmeterol Sum of stages 3-4 (μg per blister) Individual | | 8, 7 | 6, 5 | 5, 4 | 5, 5 |
| Particle Size Distribution by Cascade Impaction Salmeterol Sum of stages TP0 (μg per blister) Individual | 28 to 42 | 36, 37 37, 39 | 36, 38 35, 36 | 36, 34 38, 36 | 36, 36 36, 37 |
| Particle Size Distribution by Cascade Impaction Salmeterol Sum of stages 6, 7 & F (μg per blister) Individual | NGT 0.5 | 0.1, 0.1 0.1, 0.1 | 0.0, 0.0 0.0, 0.0 | 0.0, 0.0 0.0, 0.0 | 0.1, 0.0 0.1, 0.0 |

TABLE 117

Stability data for DISKUS ® 500/50 μg 60 Dose Product with overwrap

Packed Batch Number: K

Storage condition 25° C./60% RH
Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (μg per blister) Individual | 96 to 150 | 124, 132 138, 136 | 118, 124 120, 119 | 104, 120 113, 117 | 113, 118 118, 104 |
| Particle Size Distribution by Cascade Impaction Fluticasone Propionate Sum of stages 3-4 (μg per blister) Individual | 43 to 92 | 76, 80 83, 81 | 69, 71 70, 68 | 54, 67 61, 63 | 64, 65 66, 57 |
| Particle Size Distribution by Cascade Impaction Fluticasone Propionate Sum of stages TP0 (μg per blister) Individual | 290 to 400 | 344, 353 352, 371 | 356, 363 353, 349 | 334, 350 340, 365 | 353, 361 367, 337 |
| Particle Size Distribution by Cascade Impaction Fluticasone Propionate Sum of stages 6, 7 & F (μg per blister) Individual | NGT 2 | 1, 1 1, 1 | 1, 1 1, 1 | 0, 1 1, 1 | 1, 0 1, 0 |

TABLE 118

Stability data for DISKUS ® 500/50 μg 60 Dose Product with overwrap

Packed Batch Number: K

Storage condition 25° C./60% RH
Testing Complete

| Test | End of life Specification | Initial | 9 Months | 12 Months | 18 Months |
|---|---|---|---|---|---|
| Particle Size Distribution by Cascade Impaction Fluticasone Propionate Sum of stages 1-5 (μg per blister) Individual | 96 to 150 | 124, 132 138, 136 | 115, 113 111, 106 | 107, 85 107, 94 | 103, 103 112, 105 |
| Particle Size Distribution by Cascade Impaction Fluticasone Propionate Sum of stages 3-4 (μg per blister) Individual | 43 to 92 | 76, 80 83, 81 | 67, 60 64, 55 | 55, 41 55, 48 | 57, 52 60, 56 |
| Particle Size Distribution by Cascade Impaction Fluticasone Propionate Sum of stages TP0 (μg per blister) Individual | 290 to 400 | 344, 353 352, 371 | 351, 368 342, 361 | 356, 340 382, 359 | 350, 355 356, 365 |
| Particle Size Distribution by Cascade | NGT 2 | 1, 1 | 1, 1 | 0, 0 | 1, 0 |

TABLE 118-continued

Stability data for DISKUS ® 500/50 µg 60 Dose Product with overwrap

Packed Batch Number: K

Storage condition
25° C./60% RH
Testing Complete

| Test | End of life Specification | Initial | Storage Time 9 Months | 12 Months | 18 Months |
|---|---|---|---|---|---|
| Impaction Fluticasone Propionate Sum of stages 6, 7 & F (µg per blister) Individual | | 1, 1 | 1, 1 | 0, 0 | 1, 1 |

TABLE 119

Stability data for DISKUS ® 500/50 µg 60 Dose Product without overwrap

Packed Batch Number: K

Storage condition
25° C./75% RH
Testing Complete

| Test | End of life Specification | Initial | 2 Weeks | Storage Time 1 Month | 1.5 Months | 3 Months |
|---|---|---|---|---|---|---|
| Particle Size Distribution by Cascade Impaction Salmeterol Sum of stages 1-5 (µg per blister) Individual | 7 to 13 | 11, 12 12, 12 | 10, 10 12, 10 | 11, 11 11, 11 | 11, 10 11, 11 | 10, 11 11, 11 |
| Particle Size Distribution by Cascade Impaction Salmeterol Sum of stages 3-4 (µg per blister) Individual | 4 to 8 | 7, 7 8, 7 | 6, 6 7, 6 | 6, 6 6, 6 | 6, 5 6, 7 | 6, 6 6, 6 |
| Particle Size Distribution by Cascade Impaction Salmeterol Sum of stages TP0 (µg per blister) Individual | 28 to 42 | 36, 37 37, 39 | 34, 35 37, 36 | 35, 36 35, 35 | 35, 34 32, 38 | 32, 35 35, 35 |
| Particle Size Distribution by Cascade Impaction Salmeterol Sum of stages 6, 7 & F (µg per blister) Individual | NGT 0.5 | 0.1, 0.1 0.1, 0.1 | 0.1, 0.1 0.1, 0.0 | 0.0, 0.0 0.0, 0.0 | 0.0, 0.0 0.0, 0.0 | 0.0, 0.0 0.0, 0.0 |

TABLE 120

Stability data for DISKUS ® 500/50 µg 60 Dose Product without overwrap

Packed Batch Number: K

Storage condition
25° C./75% RH
Testing Complete

| Test | End of life Specification | Initial | 2 Weeks | Storage Time 1 Month | 1.5 Months | 3 Months |
|---|---|---|---|---|---|---|
| Particle Size Distribution by Cascade Impaction Fluticasone Propionate Sum of stages 1-5 (µg per blister) Individual | 96 to 150 | 124, 132 138, 136 | 111, 114 129, 111 | 117, 121 120, 120 | 118, 108 125, 126 | 113, 121 118, 122 |
| Particle Size Distribution by Cascade Impaction Fluticasone Propionate Sum of stages 3-4 (µg per blister) Individual | 42 to 93 | 76, 80 83, 81 | 66, 68 77, 63 | 69, 69 70, 71 | 66, 58 72, 72 | 65, 68 65, 70 |
| Particle Size Distribution by Cascade Impaction Fluticasone Propionate Sum of stages TP0 (µg per blister) Individual | 290 to 400 | 344, 353 352, 371 | 330, 340 354, 345 | 339, 353 339, 344 | 340, 329 310, 355 | 315, 343 345, 340 |
| Particle Size Distribution by Cascade Impaction Fluticasone Propionate Sum of stages 6, 7 & F (µg per blister) Individual | NGT 2 | 1, 1 1, 1 | 1, 1 1, 1 | 1, 1 1, 1 | 1, 1 1, 1 | 1, 1 1, 2 |

TABLE 121

Stability data for DISKUS ® 500/50 μg 60 Dose Product without overwrap
Samples previously stored at 25° C./60% RH with overwrap for 17 months Packed Batch Number: K Storage condition
25° C./75% RH
Testing Complete

| Test | End of life Specification | Initial | 2 Weeks | 1 Month | 1.5 Months |
|---|---|---|---|---|---|
| Particle Size Distribution by Cascade Impaction Salmeterol Sum of stages 1-5 (μg per blister) Individual | 7 to 13 | 10, 10 10, 9 | 9, 9 9, 9 | 11, 10 10, 10 | 10, 10 10, 9 |
| Particle Size Distribution by Cascade Impaction Salmeterol Sum of stages 3-4 (μg per blister) Individual | 4 to 8 | 5, 5 5, 5 | 5, 5 5, 5 | 6, 5 5, 5 | 6, 5 5, 5 |
| Particle Size Distribution by Cascade Impaction Salmeterol Sum of stages TP0 (μg per blister) Individual | 28 to 42 | 38, 35 37, 36 | 35, 36 34, 34 | 37, 35 36, 35 | 37, 36 36, 35 |
| Particle Size Distribution by Cascade Impaction Salmeterol Sum of stages 6, 7 & F (μg per blister) Individual | NGT 0.5 | 0.1, 0.0 0.0, 0.0 | 0.0, 0.1 0.0, 0.1 | 0.1, 0.1 0.0, 0.1 | 0.0, 0.0 0.1, 0.1 |

TABLE 122

Stability data for DISKUS ® 500/50 μg 60 Dose Product without overwrap
Samples previously stored at 25° C./60% RH with overwrap for 17 months (cont'd)

Packed Batch Number: K

Storage condition
25° C./75% RH
Testing Complete

| Test | End of life Specification | Initial | 2 Weeks | 1 Month | 1.5 Months |
|---|---|---|---|---|---|
| Particle Size Distribution by Cascade Impaction Fluticasone Propionate Sum of stages 1-5 (μg per blister) Individual | 96 to 150 | 109, 111 109, 105 | 100, 106 103, 102 | 119, 109 110, 109 | 108, 110 111, 103 |
| Particle Size Distribution by Cascade Impaction Fluticasone Propionate Sum of stages 3-4 (μg per blister) Individual | 43 to 92 | 58, 59 58, 54 | 53, 56 55, 55 | 62, 56 61, 61 | 60, 57 58, 56 |
| Particle Size Distribution by Cascade Impaction Fluticasone Propionate Sum of stages TP0 (μg per blister) Individual | 290 to 400 | 373, 349 367, 361 | 351, 361 343, 340 | 369, 348 357, 351 | 365, 352 352, 347 |
| Particle Size Distribution by Cascade Impaction Fluticasone Propionate Sum of stages 6, 7 & F (μg per blister) Individual | NGT 2 | 1, 0 1, 0 | 1, 1 1, 1 | 1, 1 1, 1 | 1, 1 1, 1 |

TABLE 123

Stability data for DISKUS ® 500/50 μg 60 Dose Product with overwrap

Packed Batch Number: L

Storage condition
25° C./60% RH
Testing Complete

| Test | End of life Specification | Initial | 1 Month | 3 Months | 6 Months |
|---|---|---|---|---|---|
| Particle Size Distribution by Cascade Impaction Salmeterol Sum of stages 1-5 (μg per blister) Individual | 7 to 13 | 10, 10 10, 10 | 8, 8 9, 9 | 8, 8 8, 8 | 9, 8 8, 8 |

TABLE 123-continued

Stability data for DISKUS ® 500/50 µg 60 Dose Product with overwrap

Packed Batch Number: L

Storage condition 25° C./60% RH Testing Complete

| Test | End of life Specification | Initial | 1 Month | 3 Months | 6 Months |
|---|---|---|---|---|---|
| Particle Size Distribution by Cascade Impaction Salmeterol Sum of stages 3-4 (µg per blister) Individual | 4 to 8 | 6, 6 5, 6 | 5, 4 5, 5 | 4, 4 4, 4 | 5, 4 4, 4 |
| Particle Size Distribution by Cascade Impaction Salmeterol Sum of stages TP0 (µg per blister) Individual | 28 to 42 | 36, 34 36, 35 | 36, 36 37, 37 | 36, 37 35, 36 | 36, 36 36, 37 |
| Particle Size Distribution by Cascade Impaction Salmeterol Sum of stages 6, 7 & F (µg per blister) Individual | NGT 0.5 | 0.0, 0.0 0.0, 0.0 | 0.0, 0.0 0.0, 0.0 | 0.0, 0.0 0.0, 0.0 | 0.0, 0.0 0.0, 0.0 |

TABLE 124

Stability data for DISKUS ® 500/50 µg 60 Dose Product with overwrap

Packed Batch Number: L

Storage condition 25° C./60% RH Testing Complete

| Test | End of life Specification | Initial | 9 Months | 12 Months | 18 Months |
|---|---|---|---|---|---|
| Particle Size Distribution by Cascade Impaction Salmeterol Sum of stages 1-5 (µg per blister) Individual | 7 to 13 | 10, 10 10, 10 | 10, 9 9, 9 | 8, 6 7, 7 | 9, 9 8, 8 |
| Particle Size Distribution by Cascade Impaction Salmeterol Sum of stages 3-4 (µg per blister) Individual | 4 to 8 | 6, 6 5, 6 | 5, 5 5, 5 | 4, 3 3, 4 | 5, 5 5, 5 |
| Particle Size Distribution by Cascade Impaction Salmeterol Sum of stages TP0 (µg per blister) Individual | 28 to 42 | 36, 34 36, 35 | 36, 37 35, 36 | 36, 35 35, 36 | 36, 38 34, 35 |
| Particle Size Distribution by Cascade Impaction Salmeterol Sum of stages 6, 7 & F (µg per blister) Individual | NGT 0.5 | 0.0, 0.0 0.0, 0.0 | 0.0, 0.0 0.0, 0.0 | 0.0, 0.0 0.0, 0.0 | 0.1, 0.1 0.0, 0.0 |

TABLE 125

Stability data for DISKUS ® 500/50 µg 60 Dose Product with overwrap

Packed Batch Number: L

Storage condition 25° C./60% RH Testing Complete

| Test | End of life Specification | Initial | 1 Month | 3 Months | 6 Months |
|---|---|---|---|---|---|
| Particle Size Distribution by Cascade Impaction Fluticasone Propionate Sum of stages 1-5 (µg per blister) Individual | 96 to 150 | 116, 115 105, 108 | 94, 90 101, 104 | 90, 93 89, 92 | 104, 94 88, 93 |
| Particle Size Distribution by Cascade Impaction Fluticasone Propionate Sum of stages 3-4 (µg per blister) Individual | 43 to 92 | 67, 70 60, 64 | 52, 48 54, 59 | 46, 49 47, 50 | 56, 49 44, 48 |
| Particle Size Distribution by Cascade Impaction Fluticasone Propionate Sum of stages TP0 (µg per blister) Individual | 290 to 400 | 355, 337 348, 343 | 350, 355 358, 360 | 352, 367 342, 358 | 356, 354 357, 358 |
| Particle Size Distribution by Cascade | NGT 2 | 1, 1 | 1, 0 | 0, 0 | 0, 0 |

TABLE 125-continued

Stability data for DISKUS ® 500/50 μg 60 Dose Product with overwrap

Packed Batch Number: L  
Storage condition 25° C./60% RH  
Testing Complete

| Test | End of life Specification | Initial | 1 Month | 3 Months | 6 Months |
|---|---|---|---|---|---|
| Impaction Fluticasone Propionate Sum of stages 6, 7 & F (μg per blister) Individual | | 1, 1 | 0, 1 | 0, 0 | 0, 0 |

TABLE 126

Stability data for DISKUS ® 500/50 μg 60 Dose Product with overwrap

Packed Batch Number: L  
Storage condition 25° C./60% RH  
Testing Complete

| Test | End of life Specification | Initial | 9 Months | 12 Months | 18 Months |
|---|---|---|---|---|---|
| Particle Size Distribution by Cascade Impaction Fluticasone Propionate Sum of stages 1-5 (μg per blister) Individual | 96 to 150 | 116, 115 105, 108 | 109, 96 96, 100 | 92, 71 79, 83 | 97, 97 95, 94 |
| Particle Size Distribution by Cascade Impaction Fluticasone Propionate Sum of stages 3-4 (μg per blister) Individual | 43 to 92 | 67, 70 60, 64 | 57, 51 52, 52 | 47, 32 38, 40 | 53, 54 52, 50 |
| Particle Size Distribution by Cascade Impaction Fluticasone Propionate Sum of stages TP0 (μg per blister) Individual | 290 to 400 | 355, 337 348, 343 | 357, 361 345, 355 | 360, 354 347, 363 | 360, 381 345, 353 |
| Particle Size Distribution by Cascade Impaction Fluticasone Propionate Sum of stages 6, 7 & F (μg per blister) Individual | NGT 2 | 1, 1 1, 1 | 1, 1 0, 1 | 0, 0 0, 0 | 1, 1 1, 1 |

TABLE 127

Stability data for DISKUS ® 500/50 μg 60 Dose Product without overwrap

Packed Batch Number: L  
Storage condition 25° C./75% RH  
Testing Complete

| Test | End of life Specification | Initial | 2 Weeks | 1 Month | 1.5 Months | 3 Months |
|---|---|---|---|---|---|---|
| Particle Size Distribution by Cascade Impaction Salmeterol Sum of stages 1-5 (μg per blister) Individual | 7 to 13 | 10, 10 10, 10 | 10, 9 9, 9 | 9, 9 8, 9 | 10, 9 10, 10 | 8, 7 9, 8 |
| Particle Size Distribution by Cascade Impaction Salmeterol Sum of stages 3-4 (μg per blister) Individual | 4 to 8 | 6, 6 5, 6 | 6, 5 5, 5 | 5, 5 5, 5 | 6, 5 5, 5 | 4, 4 5, 5 |
| Particle Size Distribution by Cascade Impaction Salmeterol Sum of stages TP0 (μg per blister) Individual | 28 to 42 | 36, 34 36, 35 | 38, 36 35, 37 | 37, 36 36, 37 | 36, 34 35, 36 | 36, 36 36, 36 |
| Particle Size Distribution by Cascade Impaction Salmeterol Sum of stages 6, 7 & F (μg per blister) Individual | NGT 0.5 | 0.0, 0.0 0.0, 0.0 | 0.1, 0.1 0.0, 0.0 | 0.0, 0.0 0.0, 0.0 | 0.0, 0.0 0.0, 0.0 | 0.0, 0.0 0.0, 0.0 |

TABLE 128

Stability data for DISKUS ® 500/50 μg 60 Dose Product without overwrap

Packed Batch Number: L

Storage condition
25° C./75% RH
Testing Complete

| Test | End of life Specification | Storage Time | | | | |
|---|---|---|---|---|---|---|
| | | Initial | 2 Weeks | 1 Month | 1.5 Months | 3 Months |
| Particle Size Distribution by Cascade Impaction Fluticasone Propionate Sum of stages 1-5 (μg per blister) Individual | 96 to 150 | 116, 115 105, 108 | 113, 102 101, 97 | 97, 99 94, 104 | 109, 106 109, 107 | 91, 82 97, 94 |
| Particle Size Distribution by Cascade Impaction Fluticasone Propionate Sum of stages 3-4 (μg per blister) Individual | 43 to 92 | 67, 70 60, 64 | 63, 60 58, 56 | 53, 55 53, 59 | 62, 59 61, 61 | 48, 46 52, 51 |
| Particle Size Distribution by Cascade Impaction Fluticasone Propionate Sum of stages TP0 (μg per blister) Individual | 290 to 400 | 355, 337 348, 343 | 371, 346 345, 356 | 359, 350 345, 357 | 349, 333 340, 355 | 354, 351 356, 356 |
| Particle Size Distribution by Cascade Impaction Fluticasone Propionate Sum of stages 6, 7 & F (μg per blister) Individual | NGT 2 | 1, 1 1, 1 | 1, 1 1, 1 | 0, 1 0, 1 | 1, 1 1, 1 | 0, 1 0, 0 |

TABLE 129

Stability data for DISKUS ® 500/50 μg 60 Dose Product without overwrap
Samples previously stored at 25° C./60% RH with overwrap for 17 months Packed Batch Number: L Storage condition
25° C./75% RH
Testing Complete

| Test | End of life Specification | Storage Time | | | |
|---|---|---|---|---|---|
| | | Initial | 2 Weeks | 1 Month | 1.5 Months |
| Particle Size Distribution by Cascade Impaction Salmeterol Sum of stages 1-5 (μg per blister) Individual | 7 to 13 | 8, 7 8, 8 | 8, 9 7, 8 | 9, 7 8, 8 | 9, 9 9, 9 |
| Particle Size Distribution by Cascade Impaction Salmeterol Sum of stages 3-4 (μg per blister) Individual | 4 to 8 | 4, 4 4, 4 | 4, 4 4, 4 | 4, 4 4, 4 | 5, 4 4, 4 |
| Particle Size Distribution by Cascade Impaction Salmeterol Sum of stages TP0 (μg per blister) Individual | 28 to 42 | 36, 35 38, 36 | 35, 36 34, 35 | 34, 35 37, 35 | 36, 37 36, 37 |
| Particle Size Distribution by Cascade Impaction Salmeterol Sum of stages 6, 7 & F (μg per blister) Individual | NGT 0.5 | 0.0, 0.0 0.0, 0.0 | 0.0, 0.0 0.0, 0.0 | 0.0, 0.0 0.0, 0.0 | 0.0, 0.0 0.0, 0.0 |

TABLE 130

Stability data for DISKUS ® 500/50 μg 60 Dose Product without overwrap
Samples previously stored at 25° C./60% RH with overwrap for 17 months (cont'd)

Packed Batch Number: L

Storage condition
25° C./75% RH
Testing Complete

| Test | End of life Specification | Storage Time | | | |
|---|---|---|---|---|---|
| | | Initial | 2 Weeks | 1 Month | 1.5 Months |
| Particle Size Distribution by Cascade Impaction Fluticasone Propionate Sum of stages 1-5 (μg per blister) Individual | 96 to 150 | 86, 83 94, 91 | 86, 96 79, 92 | 96, 83 85, 86 | 95, 98 97, 96 |

TABLE 130-continued

Stability data for DISKUS ® 500/50 μg 60 Dose Product without overwrap
Samples previously stored at 25° C./60% RH with overwrap for 17 months (cont'd)

Packed Batch Number: L

Storage condition 25° C./75% RH
Testing Complete

| Test | End of life Specification | Initial | 2 Weeks | 1 Month | 1.5 Months |
|---|---|---|---|---|---|
| Particle Size Distribution by Cascade Impaction Fluticasone Propionate Sum of stages 3-4 (μg per blister) Individual | 43 to 92 | 44, 43 49, 46 | 46, 49 42, 50 | 49, 43 43, 45 | 51, 47 48, 49 |
| Particle Size Distribution by Cascade Impaction Fluticasone Propionate Sum of stages TP0 (μg per blister) Individual | 290 to 400 | 356, 354 353, 359 | 350, 364 340, 349 | 337, 348 371, 347 | 358, 371 359, 372 |
| Particle Size Distribution by Cascade Impaction Fluticasone Propionate Sum of stages 6, 7 & F (μg per blister) Individual | NGT 2 | 0, 0 0, 0 | 1, 1 0, 0 | 0, 0 0, 0 | 0, 0 0, 1 |

The invention has been described in reference to the embodiments set forth above. It should be appreciated that such embodiments are for illustrative purposes only, and do not limit the scope of the invention as defined by the claims.

That which is claimed is:

1. A process for forming lactose composition suitable for use in a pharmaceutical formulation, said process comprising:
   providing a plurality of lactose particles containing no more than 10% w/w of lactose particles having a volume average particle size of about 70 microns or less, wherein said plurality of lactose particles are present as crystalline lactose;
   milling the plurality of lactose particles to yield a plurality of milled lactose particles with an average particle size, (D50), ranging from about 50 microns to about 100 microns;
   classifying said plurality of milled lactose particles into at least two fractions comprising a fine fraction and a coarse fraction wherein the fine fraction has an average particle size, (D50), ranging from 10 microns to 30 microns, and the coarse fraction has an average particle size, (D50), ranging from about 40 microns to about 250 microns; and
   combining a portion of the coarse fraction with a portion of the fine fraction to form a lactose composition consisting of the fine fraction and the coarse fraction;
   wherein said step of providing a plurality of lactose particles containing no more than 10% w/w of lactose particles having a volume average particle size of about 70 microns or less comprises obtaining said plurality of lactose particles by classifying crystalline lactose into two fractions comprising: (i) a fine fraction and (ii) said plurality of lactose particles containing no more than 10% w/w of lactose particles having a volume average particle size of about 70 microns or less.

2. The process according to claim 1, wherein the lactose is selected from the group consisting of anhydrous lactose, lactose monohydrate, and combinations thereof.

3. The process according to claim 1, further comprising combining at least one medicament with a lactose composition to form a pharmaceutical formulation, the lactose composition comprising from 0 to 100 percent by weight of the coarse fraction and from 0 to 100 percent by weight of the fine fraction.

4. The process according to claim 1, further comprising combining the lactose composition with at least one medicament to form a pharmaceutical formulation.

5. The process according to claim 1, further comprising combining: (i) from 0 to 100 percent by weight of the coarse fraction, (ii) from 0 to 100 percent by weight of the fine fraction, and (iii) at least one medicament to form a pharmaceutical formulation.

6. The process according to claim 3, wherein the pharmaceutical formulation is a dry powder pharmaceutical formulation suitable for inhalation.

7. The process according to claim 3, wherein the at least one medicament comprises at least one beta agonist.

8. The process according to claim 7, wherein the at least one beta agonist comprises salmeterol xinafoate.

9. The process according to claim 7, wherein the at least one beta agonist comprises salbutamol sulphate.

10. The process according to claim 3, wherein the at least one medicament comprises at least one anti-inflammatory steroid.

11. The process according to claim 10, wherein the at least one anti-inflammatory steroid comprises fluticasone propionate.

12. The process according to claim 3, wherein the at least one medicament comprises at least one beta agonist and at least one anti-inflammatory steroid.

13. The process according to claim 12, wherein the at least one beta agonist comprises salmeterol xinafoate and the at least one anti-inflammatory steroid comprises fluticasone propionate.

14. The process according to claim 3, wherein the at least one medicament is selected from the group consisting of albuterol sulphate, salmeterol xinafoate, fluticasone propionate, beclomethasone dipropionate, and combinations thereof.

15. The process according to claim 3, wherein said pharmaceutical formulation further comprises at least one additional excipient.

* * * * *